(12) United States Patent
Bramlet

(10) Patent No.: US 6,475,242 B1
(45) Date of Patent: Nov. 5, 2002

(54) ARTHROPLASTY JOINT ASSEMBLY

(76) Inventor: Dale G. Bramlet, 2044 Brightwaters Blvd., NE., St. Petersburg, FL (US) 33704-3010

(*) Notice: Subject to any disclaimer, the term of this patent is extended or adjusted under 35 U.S.C. 154(b) by 0 days.

(21) Appl. No.: 09/236,627

(22) Filed: Jan. 26, 1999

Related U.S. Application Data

(62) Division of application No. 08/615,022, filed on Mar. 13, 1996, now Pat. No. 5,984,970.

(51) Int. Cl.$^7$ .................................................. A61F 2/42
(52) U.S. Cl. .............................. 623/21.11; 623/21.15; 623/23.44
(58) Field of Search ..................... 623/21, 22, 21.11, 623/21.12, 21.13, 21.14, 21.15–21.19

(56) References Cited

U.S. PATENT DOCUMENTS

| | | |
|---|---|---|
| 2,696,817 A | 12/1954 | Prevo |
| 3,462,765 A | 8/1969 | Swanson |
| 3,593,342 A | 7/1971 | Niebauer |
| 3,798,679 A | 3/1974 | Ewald |
| 3,805,302 A | 4/1974 | Mathys |
| 3,848,276 A | 11/1974 | Martinez |
| 3,875,594 A | 4/1975 | Swanson |
| 3,879,767 A | 4/1975 | Stubstad |
| 3,886,600 A | 6/1975 | Kahn et al. |
| 3,899,796 A | 8/1975 | Bahler et al. |
| 3,946,445 A | 3/1976 | Bentley et al. |
| 3,986,212 A | 10/1976 | Sauer |
| 3,990,116 A | 11/1976 | Fixel et al. |
| 3,991,425 A | 11/1976 | Martin et al. |
| 3,992,726 A | 11/1976 | Freeman et al. |
| 4,011,603 A | 3/1977 | Steffee |
| 4,059,854 A | 11/1977 | Laure |
| 4,150,444 A | 4/1979 | Hagert |
| 4,158,893 A | 6/1979 | Swanson |
| 4,175,555 A | 11/1979 | Herbert |
| 4,193,139 A | 3/1980 | Walker |
| 4,231,121 A | 11/1980 | Lewis |
| 4,242,759 A | 1/1981 | White |
| 4,267,608 A | 5/1981 | Bora, Jr. |
| 4,313,232 A | 2/1982 | Habal et al. |
| 4,352,212 A | 10/1982 | Greene et al. |
| 4,375,703 A | 3/1983 | Evans et al. |
| 4,467,479 A | 8/1984 | Brody |
| 4,470,158 A | 9/1984 | Pappas et al. |
| D291,731 S | 9/1987 | Aikins |

(List continued on next page.)

FOREIGN PATENT DOCUMENTS

| | | |
|---|---|---|
| FR | 2651-119 A | 1/1991 |
| WO | WO88/01854 | 3/1988 |
| WO | WO91/16017 | 10/1991 |

*Primary Examiner*—David H. Willse
*Assistant Examiner*—Hieu Phan
(74) *Attorney, Agent, or Firm*—Kenyon & Kenyon

(57) ABSTRACT

An arthroplasty joint assembly for medically and articulately interconnecting first and second opposed end regions of lengthwise adjacent first and second bones. The artificial joint assembly includes a first assembly including external threading extending lengthwise from a generally pointed end of the first assembly for anchoring the first assembly within a cavity of the first bone such that an opposite end of the first assembly extends toward the second bone. The artificial joint assembly also includes a second assembly having external threading extending lengthwise from a generally pointed end of the second assembly for anchoring the second assembly within a cavity in the second bone and such that an opposite end of the second assembly extends toward the first bone. The artificial joint assembly further includes a connector operably associated with and pivotally interconnecting the first and second assemblies to permit the first and second bones anchored thereto to articulately flex relative to each other while maintaining the first and second bones in relationship to each other.

18 Claims, 42 Drawing Sheets

U.S. PATENT DOCUMENTS

| | | |
|---|---|---|
| 4,725,280 A | 2/1988 | Laure |
| 4,759,768 A | 7/1988 | Hermann et al. |
| 4,787,908 A | 11/1988 | Wyss et al. |
| 4,911,719 A | 3/1990 | Merle |
| 4,944,758 A | 7/1990 | Bekki et al. |
| 4,969,909 A | 11/1990 | Barouk |
| 5,011,497 A * | 4/1991 | Persson et al. ............... 623/21 |
| 5,062,851 A * | 11/1991 | Branemark .................. 623/18 |
| 5,092,896 A | 3/1992 | Meuli et al. |
| 5,108,443 A | 4/1992 | Branemark |
| 5,133,761 A | 7/1992 | Krouskop |
| 5,147,386 A | 9/1992 | Carigan et al. |
| 5,171,284 A | 12/1992 | Branemark |
| 5,207,712 A | 5/1993 | Cohen |
| 5,290,314 A | 3/1994 | Koch et al. |
| 5,314,479 A | 5/1994 | Rockwood, Jr. et al. |
| 5,417,692 A | 5/1995 | Goble et al. |
| 5,507,823 A * | 4/1996 | Walston et al. ............... 623/21 |
| 5,709,683 A * | 1/1998 | Bagby ......................... 606/61 |
| 5,906,616 A * | 5/1999 | Pavlov et al. ................. 606/61 |

* cited by examiner

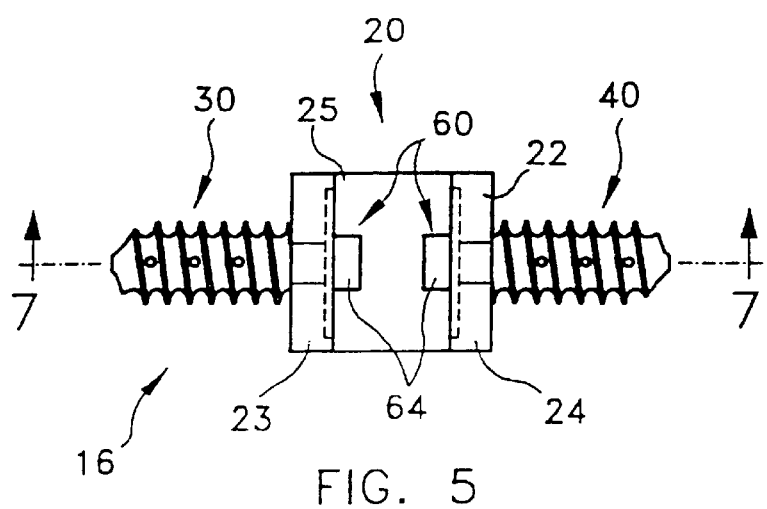
FIG. 5
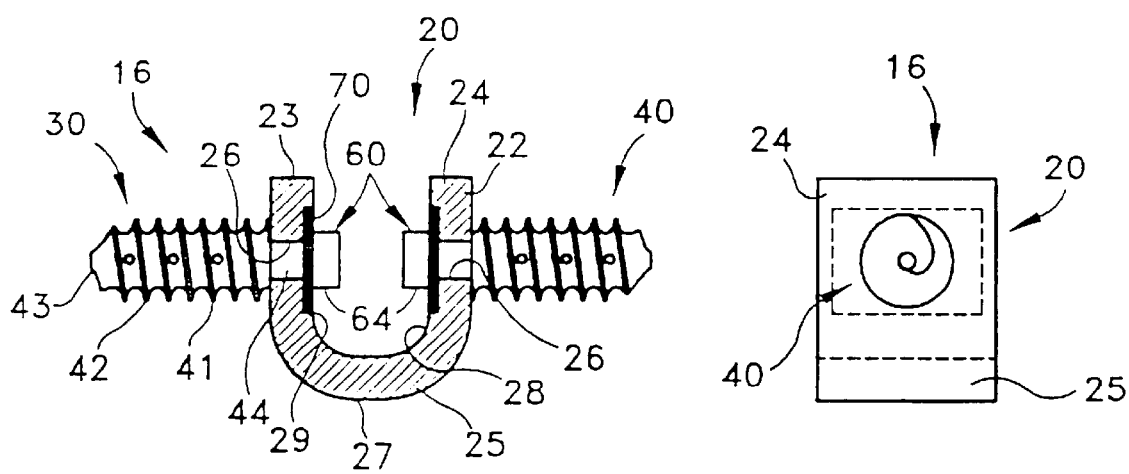
FIG. 7
FIG. 6

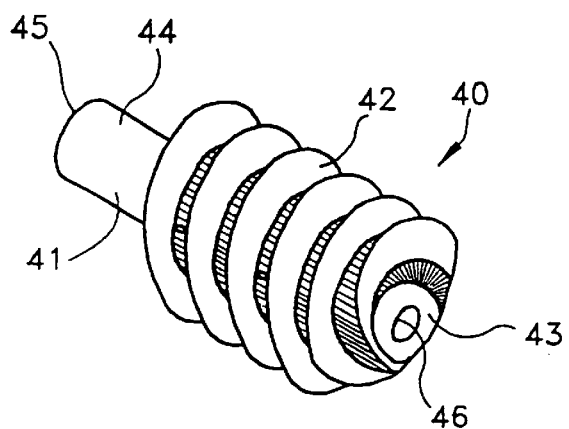
FIG. 14
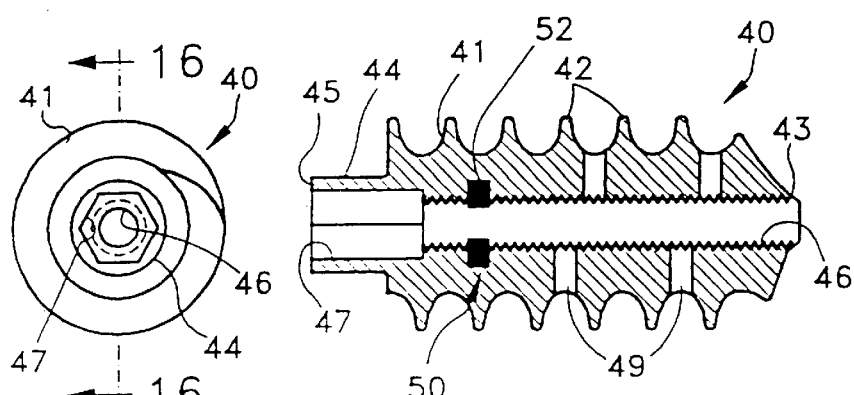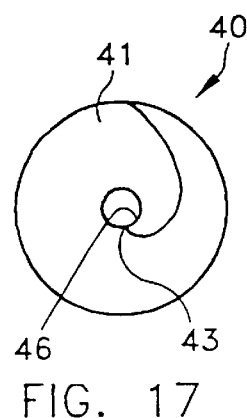
FIG. 15  FIG. 16  FIG. 17
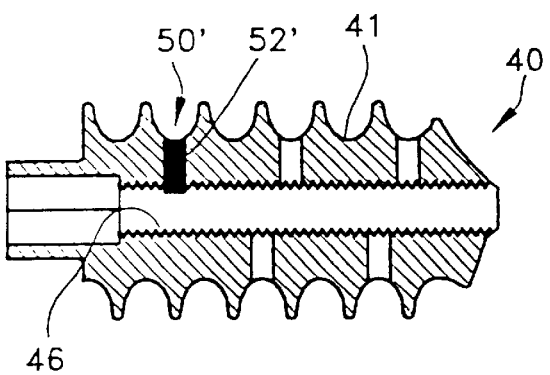
FIG. 18

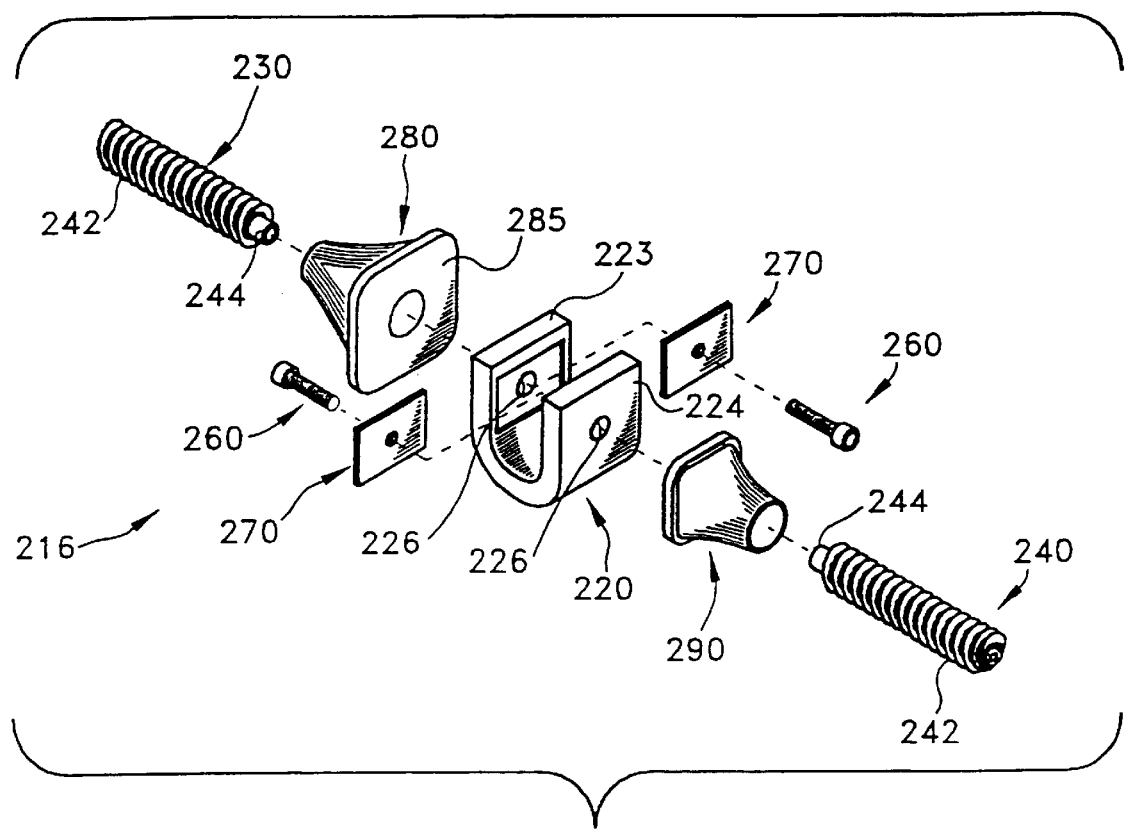
FIG. 48
FIG. 49
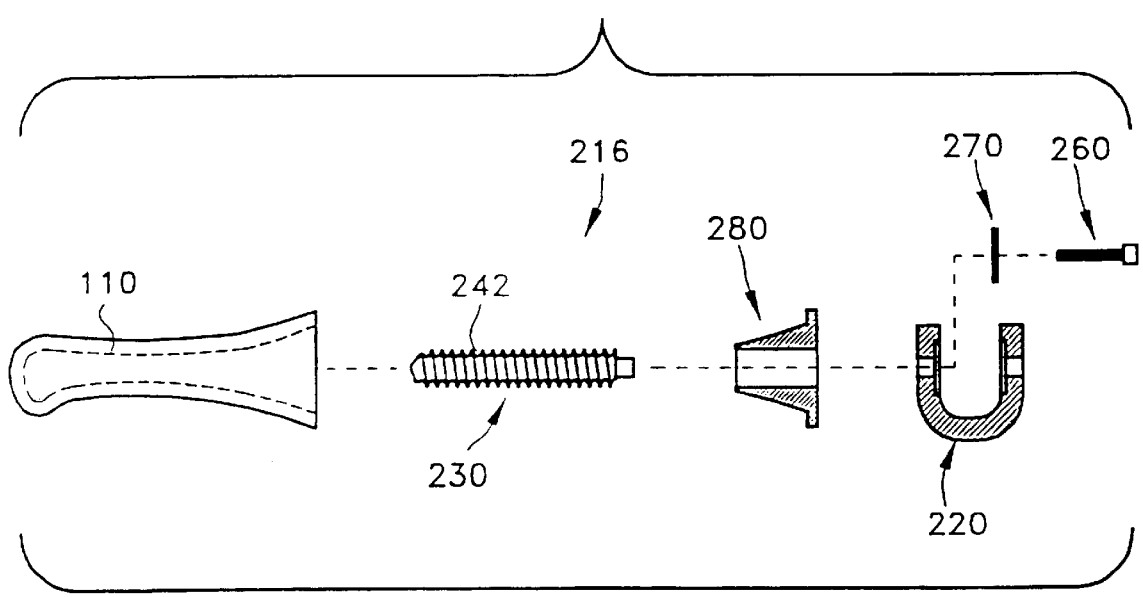

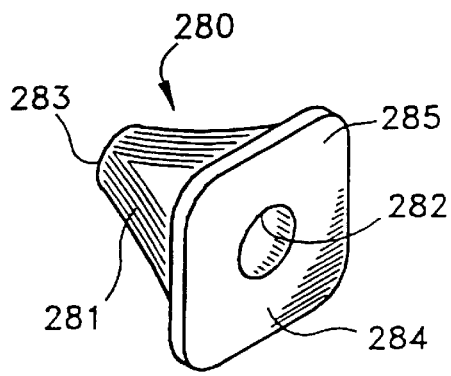
FIG. 50
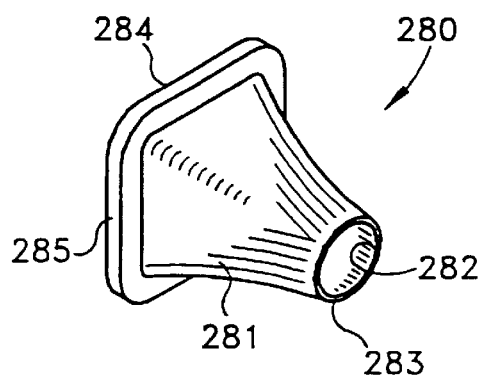
FIG. 51
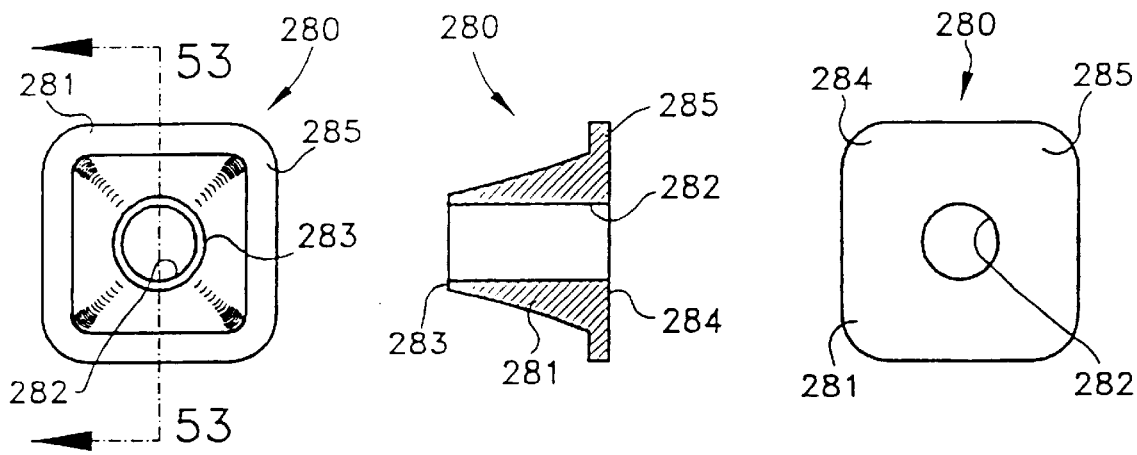
FIG. 52
FIG. 53
FIG. 54

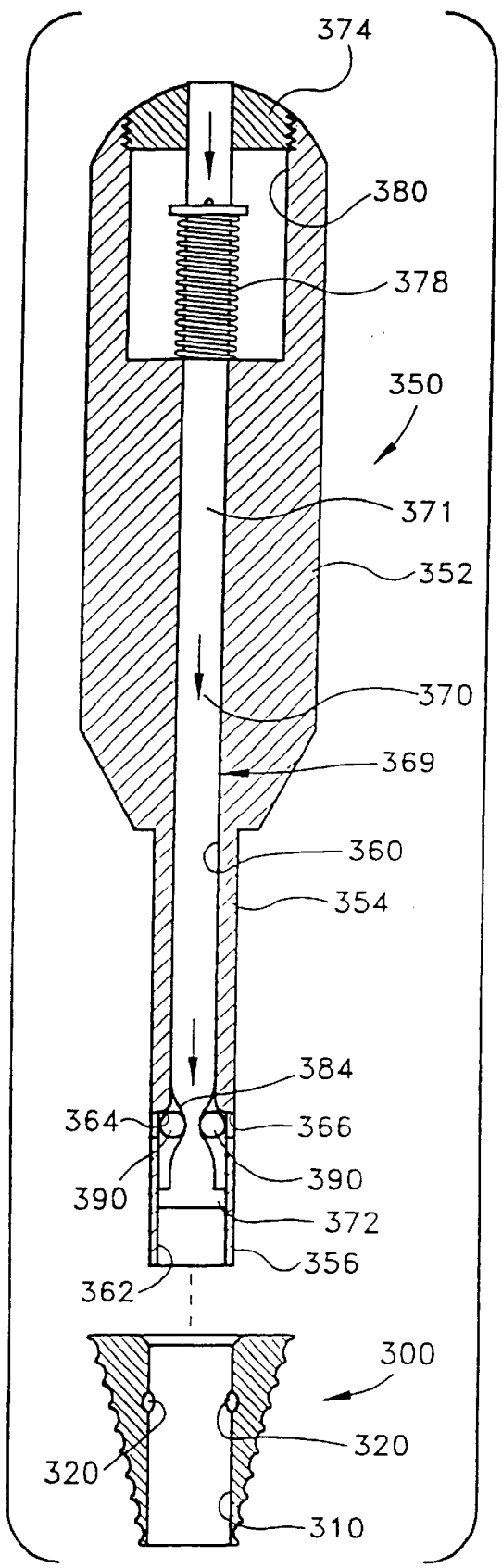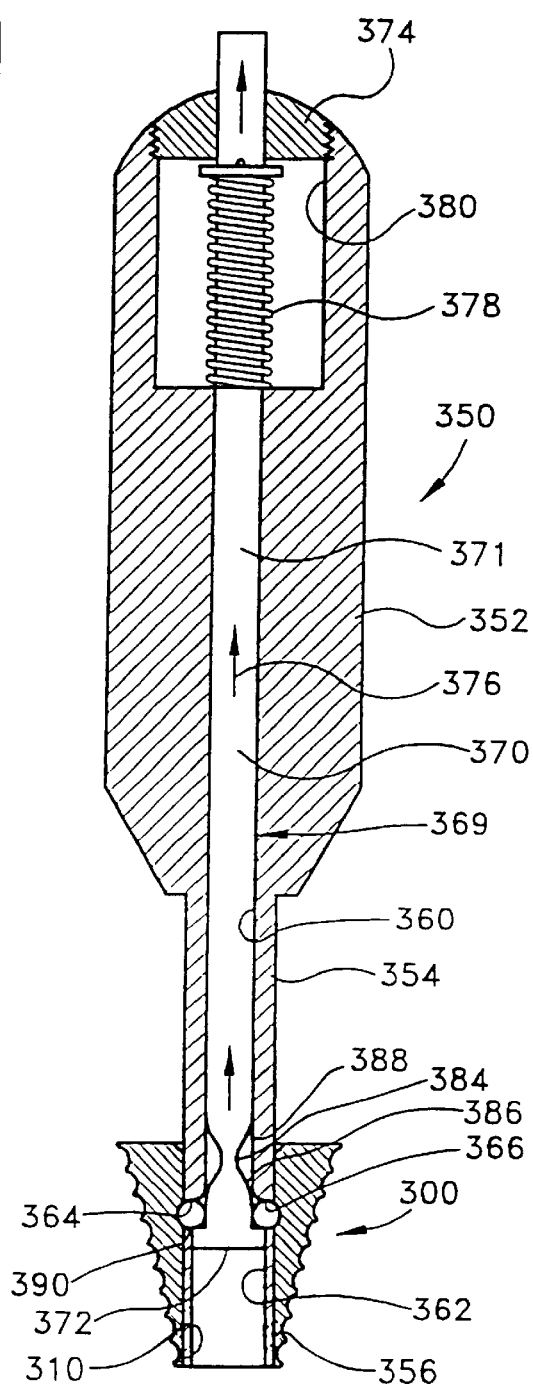
FIG. 66
FIG. 63

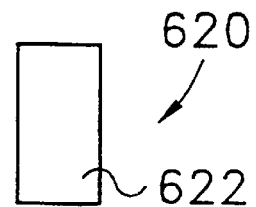
FIG. 89          FIG. 88
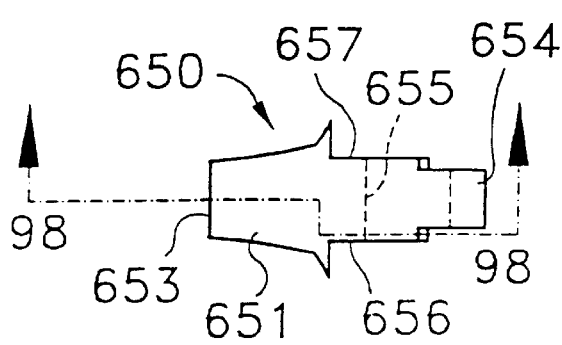
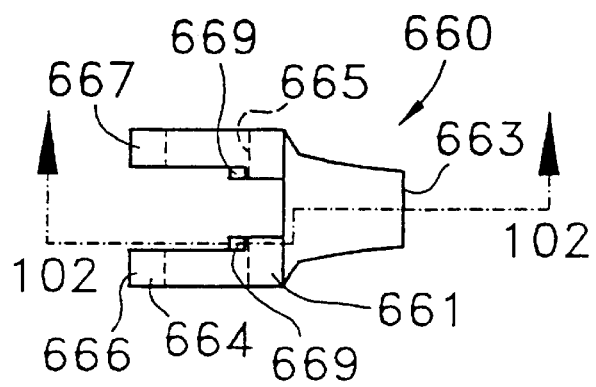
FIG. 96          FIG. 100
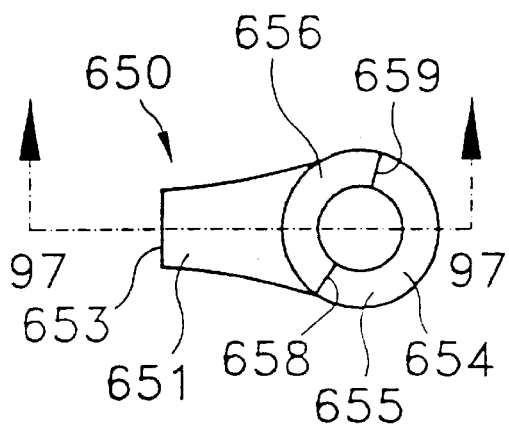
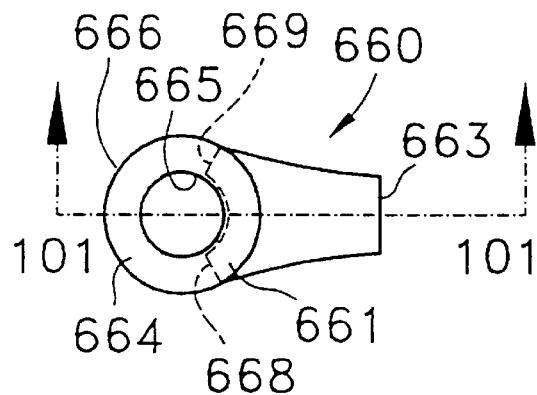
FIG. 95          FIG. 99

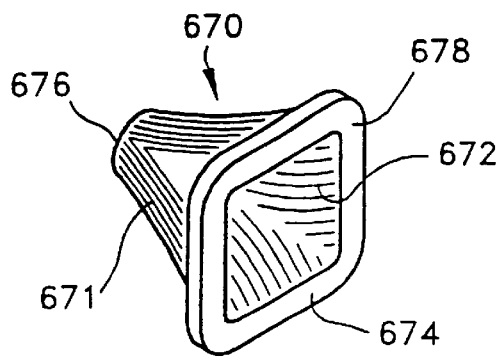
FIG. 105
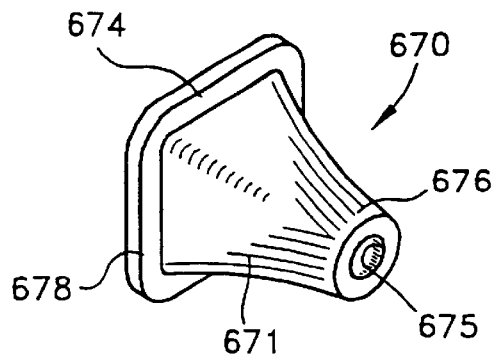
FIG. 106
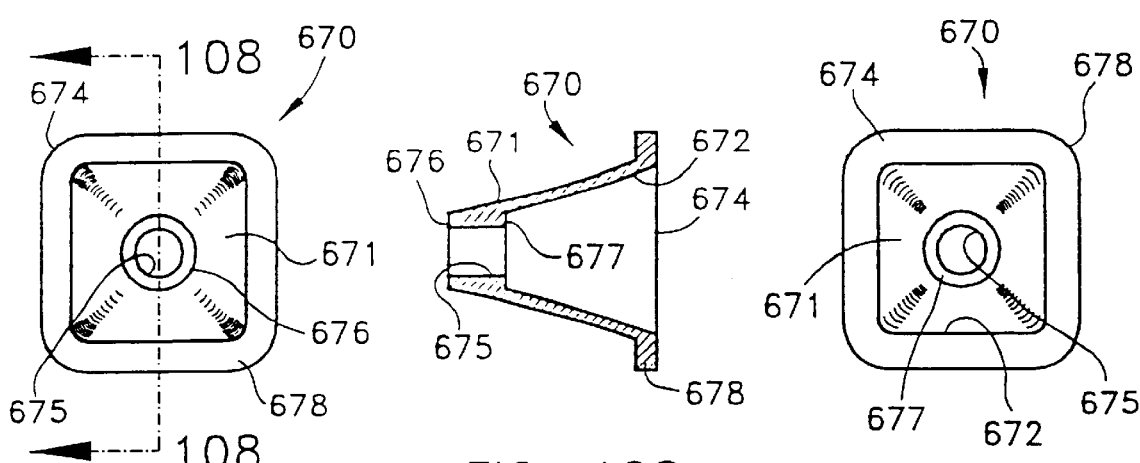
FIG. 107
FIG. 108
FIG. 109

ARTHROPLASTY JOINT ASSEMBLY

This application is a division of application Ser. No. 08/615,022, filed Mar. 13, 1996 now U.S. Pat. No. 5,984,870.

FIELD OF THE INVENTION

The present invention generally relates to biological medical instruments and, more particularly, to an arthroplasty joint assembly for medically and articulately interconnecting opposed end regions of adjacent end-to-end bones of a patient.

BACKGROUND OF THE INVENTION

There have been a number of techniques historically utilized to fuse smaller joints in a living body such as finger joints and toe joints. The use of K wires arranged in a cross or parallel fashion complimented with dental wiring to augment the fixation has also been proposed. Moreover, the use of a cone and cup technique coupled with a K wire fixation technique has also been proposed. The use of small screws and plates to supplement fixation of bony surfaces as well as several novel screw systems such as marketed by Howmedica and described in U.S. Pat. No. 5,417,692 have also been proposed for fixation of bones for fusion.

With the development of arthritic conditions of the metacarpal phalangeal joints, such as commonly seen in patients with rheumatoid arthritis, as well as arthritic conditions of the proximal interphalangeal joint, such as commonly seen in patients with rheumatoid and osteoarthritis, a number of devices have been proposed to alieviate the severe pain, deformity, and disability arising out of the arthritic destruction of these joints. One proposal involves the use of a silicone implant arthroplasty as a spacer coupled with reconstruction and realignment of adjacent ligaments and tendons to effect a satisfactory joint replacement in metacarpal and proximal interphalangeal joints of the hand. Such devices have also been used in the metacarpal phalangeal joint of the foot as well as other interphalangeal joints to a lesser degree. Use of these devices, however, in distal interphalangeal joints is frequently associated with failure due to the excessive forces across these joints.

While these artificial joints act as spacers, they are fraught with a difficulty of long-term failure due to the resorption of adjacent bone and the lack of permanent fusion or fixation. Thus, these joints act merely as spacers, and do not provide a degree of intrinsic stability, nor do they physically bond or become attached to the adjacent bone. Instead, they are surrounded with a membrane representative of a giant cell reaction or foreign body reaction.

U.S. Pat. No. 5,108,443 to P. Branemark and issued Apr. 28, 1992, discloses a technique wherein a screw assembly is placed in a bone that appears to be fairly uniform in cross-section between opposite ends thereof. This technique fails to take into account the proximal widening of bones known in the metaphysis, and the substantial mismatch of size and canal diameters that can occur in both normal and especially arthritic bone. Similarly structured devices also fail to allow a variability of size mismatch wherein the proximal phalanx of a hand may be substantially asymmetrical in size with the standard sizes available that would correspond to a metacarpal phalangeal joint within the enormity of population ranges sized by these systems. This lack of variability can lead to difficulty with stability of a finger joint implant, wherein the metacarpal phalangeal joint side may be quite rigid, but the proximal phalangeal side alternatively may be loose. Attempts to place a large implant to accommodate the loose proximal interphalangeal side may be fraught with excessive resection of bone on the metacarpal phalangeal joint side in order to accommodate the large size implant to obtain stability.

Grommets have also been proposed for use to provide rotational control, but do not take into account the size mismatch that can occur. This lack of variability of implants can be found both for enlargement of either the distal or proximal bone abnormally compared to the corresponding opposable bony surface. This can especially occur in metacarpal phalangeal joints, but alternatively can occur in proximal and distal interphalangeal joints of the hands. This lack of size variability due to the lack of modularity is a substantial problem and can lead to late failure with rotary changes and provide a substantial loss of stability and function as well as a decreased cosmetic result.

Thus, there is a need and a desire for an improved joint assembly that can be used as a distal interphalangeal joint, a proximal interphalangeal joint, or as a metacarpal phalangeal joint as required. There is also a need and a desire for a joint assembly that addresses long-term fixation needs, the rigidity of fixation relative to the bones, and the ease of interchangability in the case of failure with a solidly anchored support.

SUMMARY OF THE INVENTION

In view of the above, and in accordance with the present invention, there is provided an arthroplasty joint assembly for medically and articulately interconnecting first and second opposed end regions of lengthwise adjacent first and second bones. The joint assembly of the present invention includes a first screw having external generally uniformly pitched threading extending lengthwise from a generally pointed end of the screw for permanently anchoring the first screw in the medullary cavity of the first bone such that a joint end of the first screw projects a predetermined endwise distance beyond and away from the end region of the first bone and extends toward the second bone. The joint assembly further includes a second screw having external generally uniformly pitched threading extending lengthwise from a generally pointed end of the second screw for permanently anchoring the second screw in the medullary cavity of the second bone such that a joint end of the second screw projects a predetermined endwise distance beyond and away from the end region of the second bone and extends toward the first bone. The respective joint ends of the first and second screws are fixedly interconnected to each other by a connector. The connector permits the first and second screws and the bones anchored thereto to articulately flex relative to one another while maintaining the first and second bones in fixedly joined relationship relative to each other.

In a preferred form of the invention, each screw of the joint assembly defines a coaxial bore that opens to a trailing end of the screw and to the end region of the bone affixed to the screw. The bore has internal uniformly pitched threading extending along at least the lengthwise portion thereof.

In one form of the invention, the connector comprises a flexible generally U-shaped member, having two generally parallel leg portions that are flexibly joined to each other by a bight portion of the member. Fasteners interconnect the leg portions of the member to the joint ends of the first and second screws. In a most preferred form of the invention, a forced distribution member cooperates with a headed portion of each fastener and the leg portion of the U-shaped connector so as to broadly distribute forces developed by the fastener connecting the connector to the screw. In another form of the invention, the joint end of the first and second screw has an eye portion defining a bore having a closed margin that is defined entirely by the joint end of the respective screw. The connector comprises a generally cylindrical pin that fits through each bore to articulately interconnect the first and second screws to each other. In this form of the invention, the joint end of each screw can be either integrally formed with the screw or as a separate element which is threadably received within the threaded bore of the screw. In this form of the invention, the eye portion of each fastener is preferably configured with stops such that when the joint ends of the first and second screws are interconnected to each other, the respective stops on the joint end portions of the screws cooperate relative to each other to limit the angular articulation of the first and second screws relative to each other.

As mentioned, artificial joints that rely solely on fasteners or screws to secure the implanted artificial joint assembly in place often fail because the screw tends to loosen over time. Another aspect of the present invention relates to the use of grommets in operable association with each bone screw or fastener of the artificial joint assembly. The grommets are designed and configured to promote boney ingrowth of the surrounding bone tissue. As will be appreciated by those skilled in the art, the screws of the joint assembly of the present invention are formed of a material that allows early fixation of bone to the screw. While the bone screw initially fastens the joint assembly in place, the grommets of the joint assembly enable bony ingrowth for long-term stability of the joint assembly. With resorption of bone that frequently occurs around a screw, the grommet can provide for long-term stability if resorption does occur around the screw.

An alternative form of the invention is disclosed for those situations where greater stability is required, such as the index metacarpal phalangeal joint and proximal interphalangeal joint where substantial and oppositely directed forces are applied as seen in pinching type activities. This alternative type of joint assembly implant would be especially helpful in a patient prone to failure secondary to rotational or angular deformities that could occur with a U-shaped joint.

Numerous other features and advantages of the present invention will become readily apparent from the following detailed description, the appended claims, and the accompanying drawings.

DETAILED DESCRIPTION OF THE DRAWINGS

FIG. 5 is a top plan view of the arthroplasty joint assembly of the present invention;

FIG. 6 is a right end view of the joint assembly illustrated in FIG. 5;

FIG. 7 is a sectional view taken along line 7—7 of FIG. 5;

FIG. 14 is a perspective view of another component part of that embodiment of the invention illustrated in FIG. 5;

FIG. 15 is a left end view of that component part illustrated in FIG. 14;

FIG. 16 is a sectional view taken along line 16—16 of FIG. 15;

FIG. 17 is a right end view of that component part of the invention illustrated in FIG. 14;

FIG. 18 is a sectional view similar to FIG. 16, but showing an alternative form of the component illustrated;

FIG. 48 is an exploded perspective view of that embodiment of the present invention, schematically illustrated in FIG. 45;

FIG. 49 is a partial sectional view of the present invention with component parts thereof shown in disassembled relation relative to each other;

FIG. 50 is a perspective view of one component part of the present invention;

FIG. 51 is another perspective view of the component part of the present invention shown in FIG. 50;

FIG. 52 is a left-end view of that component part illustrated in FIG. 50;

FIG. 53 is a sectional view taken along line 53—53 of FIG. 52;

FIG. 54 is a right-end view of that component part illustrated in FIG. 50;

FIG. 63 is an enlarged cross-sectional view similar to FIG. 55 showing the broach releasably attached to a distal end of the tool;

FIG. 66 is an enlarged sectional view similar to FIG. 63 showing the broach released from the tool;

FIG. 88 is a top plan view of a connector for that embodiment of the invention illustrated in FIG. 86;

FIG. 89 is an elevational view of the connector illustrated in FIG. 88;

FIG. 95 is an elevational view of another component part of that embodiment of the invention illustrated in FIGS. 86 and 87;

FIG. 96 is a top plan view of the component part illustrated in FIG. 95;

FIG. 99 is an elevational view of another component part of that embodiment of the invention illustrated in FIGS. 86 and 87;

FIG. 100 is a top plan view of the component part illustrated in FIG. 99;

FIG. 105 is a perspective view of another component part of that embodiment of the invention illustrated in FIGS. 86 and 87;

FIG. 106 is another perspective view of that component part illustrated in FIG. 105 but looking at a different angle;

FIG. 107 is a left-end view of the component part illustrated in FIGS. 105 and 106;

FIG. 108 is a sectional view taken along line 108—108 of FIG. 107;

FIG. 109 is a right-end view of the component part illustrated in FIGS. 105 and 106;

DETAILED DESCRIPTION OF THE PRESENT INVENTION

Figure 1:
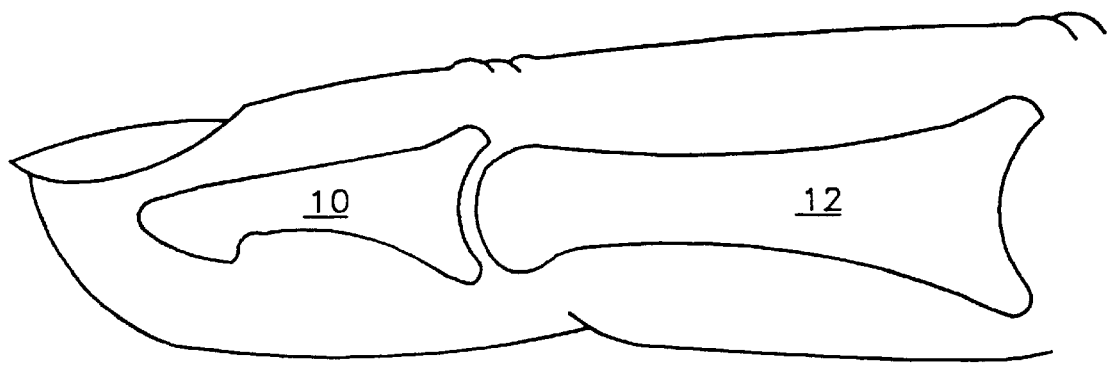
FIG. 1 is a cross section of a distal interphalangeal finger joint.

While the present invention is susceptible of embodiment in various forms, there are shown in the drawings and will hereinafter be described preferred embodiments of the invention with the understanding that the present disclosure is to be considered as setting forth exemplifications of the invention which are not intended to limit the invention to the specific embodiments illustrated.

Several exemplary embodiments of inventive arthroplasty joint assemblies will be described in detail in connection with the drawings. The different embodiments of the invention are shown as implants between adjacent elongated bones of a person's finger. It should be kept in mind, however, that the teachings and principals of the present invention are not limited to this exemplary application. As will be seen, the present invention provides a joint assembly which is simple in construction, form, and function and this joint assembly can be readily modified to particularly suit requirements of and replace articulated joints other than finger joints in a living body such as those of the toes.

Referring now to the drawings, wherein like reference numerals refer to like parts throughout the several views, in FIG. 1 there is schematically represented a distal interphalangeal finger joint comprised of two bones 10 and 12 in end-to-end relation relative to each other. The distal interphalangeal joint, shown in FIG. 1, is a model wherein the joint assembly of the present invention can be utilized to fixedly and articulately interconnect and restructure the finger joint. As will be appreciated, and as will be discussed below, the present invention is equally applicable to other situations beyond a distal interphalangeal finger joint.

Figure 2:
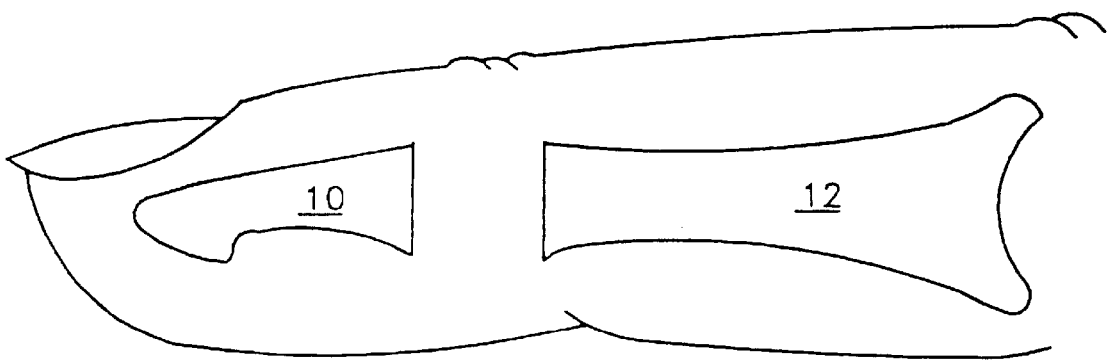
FIG. 2 is a cross-sectional view similar to FIG. 1, but showing the bones of the distal interphalangeal joint following a surgical procedure being performed thereto.
Figure 3:
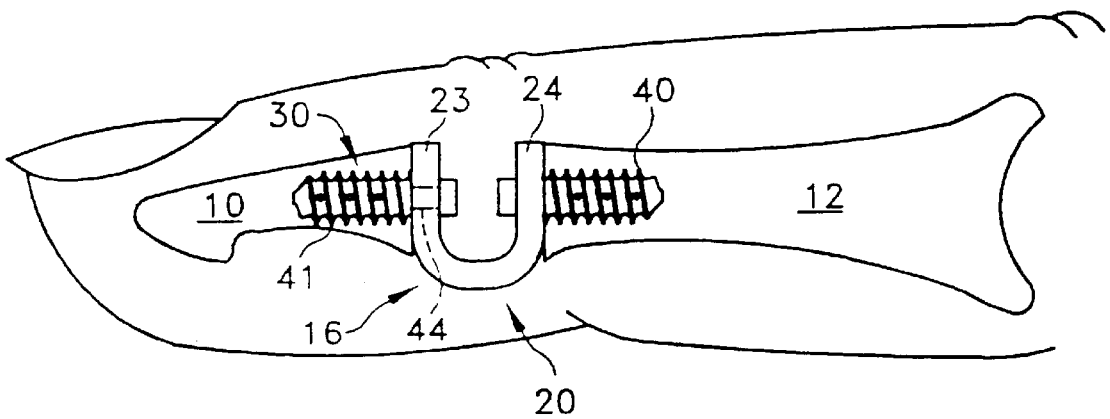
FIG. 3 is a cross-sectional view of the distal interphalangeal joint being reconstructed with the present invention.

In operation, and as shown in FIG. 2, prior to insertion of the joint assembly of the present invention therebetween, an end portion of the first bone 10 is surgically cut thus exposing the medullary cavity there within. The end portion of the second bone 12 is also surgically cut thereby exposing the medullary cavity there within. As shown in FIG. 3, an arthroplasty joint assembly 16 embodying principles of the present invention is then fixedly secured to and between the bones 10 and 12 to repair and replace the natural finger joint.

One embodiment of the arthroplasty finger joint 16 according to the present invention is schematically represented in FIGS. 4 through 8. As shown in FIGS. 4 through 8, one embodiment of the joint assembly 16 comprises a connector 20 for fixedly and articulately interconnecting joint ends of first and second screws 30 and 40, respectively, to each other.

One form of connector 20 is shown in FIGS. 9 through 13. Connector 20 is fabricated from a material that is biocompatible with the human and bone tissue and is preferably selected from a class comprised of: silicone based polymer of the type sold by Dow Corning Corporation under the tradename "Silastic". As shown, connector 20 comprises a flexible generally U-shaped member 22 having two generally parallel leg portions 23 and 24 that are spaced a predetermined distance apart and are flexibly joined to each other by a bight portion 25. Each leg 23, 24 of connector 20 defines a throughbore 26 arranged adjacent a distal end thereof. Moreover, connector 20 defines relatively smooth and parallel outer and inner surfaces 27 and 28, respectively. For purposes to be described hereinbelow, a recess 29 is formed on the inner surface 28 of the connector 20 in generally coaxially alignment with the bore 26.

In this embodiment of the invention, the first and second screws or fasteners 30 and 40, respectively, are substantially identical. Accordingly, only screw 40 will be described in detail with the understanding that screw 30 is substantially identical thereto.

As shown in FIGS. 14 through 18, each fastener or screw comprises an elongated member 41 having external threading 42 extending axially rearwardly from a generally pointed or leading end 43 thereof. The elongated member 41 is preferably fabricated from a material that is biocompatible with the human and bone tissue and is preferably selected from a class comprised of: titanium, a titanium based alloy, stainless steel or a cobalt chromium alloy. The external threading 42 extends axially lengthwise of member 41 and has a uniform pitch between leading and trailing ends thereof. The threading 42 on member 41 has a relatively coarse pitch such that a substantive holding force will be developed when the screw 40 is threadably secured within the bone substance of the respective bones.

As shown in FIGS. 14, 15 and 16, the elongated member 41 of each screw 30, 40 includes a reduced diameter portion 44. The reduced diameter portion 44 extends forwardly a predetermined axial distance from a trailing end 45 of member 41.

Member 41 defines an axial bore 46 that extends through member 41 and opens to the leading and trailing ends 43 and 45, respectively, thereof. For at least a portion of its length, bore 46 defines internal threading which is preferably of a uniform pitch along the axial length thereof.

In the illustrated form of the invention, the trailing end of bore 46 is provided with a specifically shaped counterbore portion 47 that is coaxially arranged relative to bore 46. The purpose of the counterbore portion 47 is to releasably accommodate a driving tool capable of imparting turning movements to the screw. In the illustrated embodiment, a hexagonally shaped counterbore 47 is provided but it will be appreciated that any suitably shaped tool receiving configuration could be provided at the trailing end 45 of the screw for imparting turning movements thereto.

As shown in FIG. 16, member 41 may further define a series of radially extending bores or openings 49 that are axially spaced relative to each other along the length of member 41. As shown, each bore 49 opens at one end to the throughbore 46 and opens at an opposite end to a root area of the external threading 42. The purpose of bores 49 is to direct a suitable sealant through the bore and into the bone substance once the screw 30, 40 is securely fastened within the bone.

As shown in FIG. 16, and for purposes to be described hereinbelow, member 41 of each screw or fastener 30, 40 further includes a retainer apparatus 50. As shown, the retainer apparatus 50 preferably comprises an annular insert 52 arranged axially along and in combination with the internal threading of bore 46. Insert 52 is formed from a material that is biocompatible with the human and bone tissues and is preferably chosen from a class including: nylon or ultra-high molecular weight polyethylene.

FIG. 18 shows an alternative form of a retainer apparatus 50' that can be used in combination with the member 41 of each screw or fastener 30, 40. The alternative retainer apparatus 50' comprises an insert 52' arranged axially along and in combination with the internal threading of bore 46. Insert 52' is formed from a class of materials similar to that chosen for insert 52 and described above.

Figure 4:
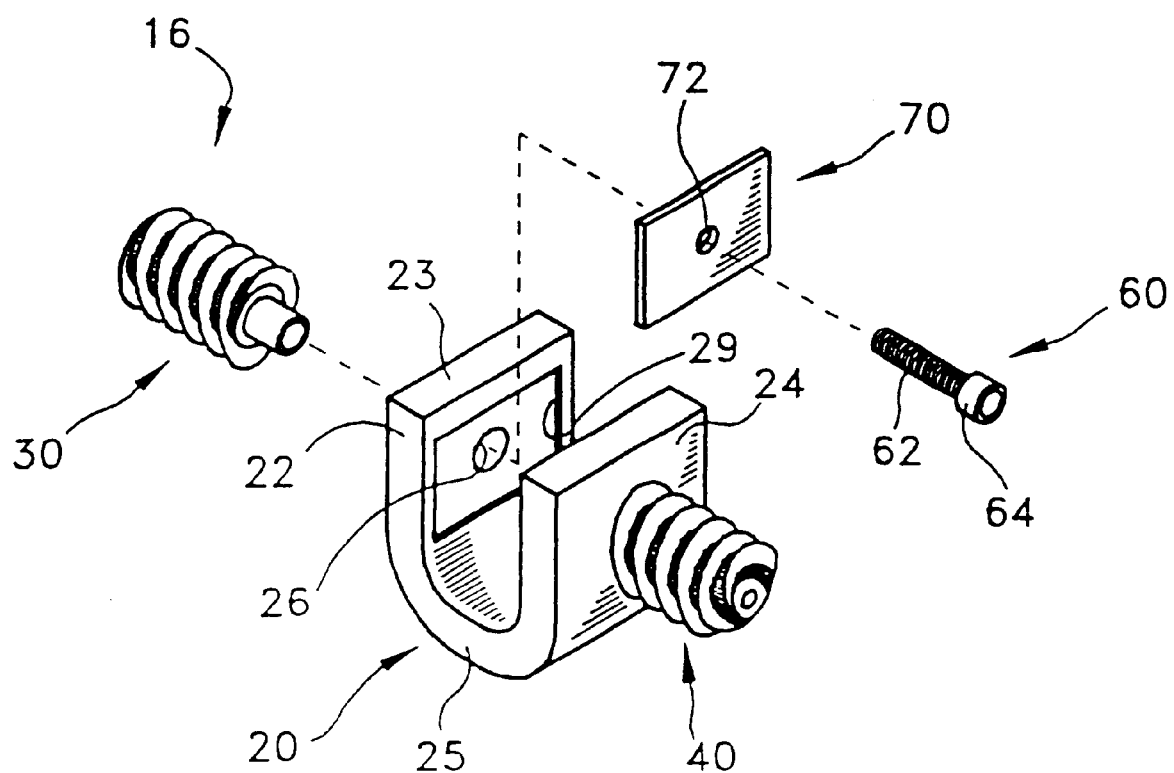
FIG. 4 is an exploded perspective view of one embodiment of the present invention.

Referring to FIGS. 4, 5 and 7, the illustrated embodiment of the joint assembly 16 further comprises a pair of fasteners 60. In this embodiment of the invention, the fasteners 60 serve to fixedly interconnect the joint end of each screw 30, 40 to a respective leg portions 23, 24 of the connector 20.

Figure 19:
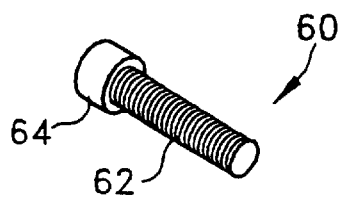
FIG. 19 is a perspective view of another component part of that embodiment of the invention illustrated in FIG. 5.
Figure 20:
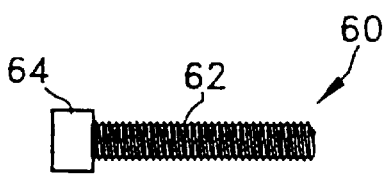
FIG. 20 is an elevational view of that component part illustrated in FIG. 19.
Figure 24:
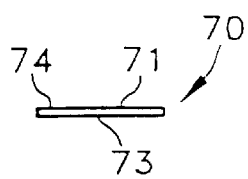
FIG. 24 is a top plan view of that component part illustrated in FIG. 23.
Figure 22:
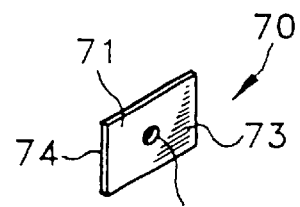
FIG. 22 is a perspective view of another component part of that embodiment of the present invention illustrated in FIG. 5.
Figure 23:
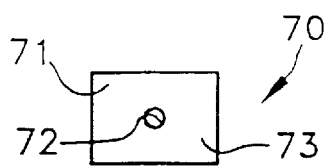
FIG. 23 is an elevational view of that component part illustrated in FIG. 22.
Figure 25:
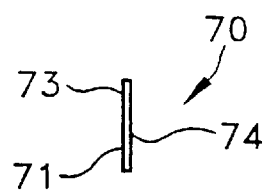
FIG. 25 is a right end view of that component part illustrated in FIG. 23.

As shown in FIGS. 19 and 20, each fastener 60 includes a threaded shank portion 62 and an enlarged head portion 64. The external threading on the shank portion 62 of fastener 60 has a pitch that corresponds to the pitch of the internal threading extending along at least a portion of the bore 46 defined by member 41 of each screw 30, 40. In the embodiment of the fastener shown, the diameter of the shank portion 62 is specifically sized to fit endwise through the bore 26 defined in each leg portion 23, 24 of the connector 20. The head portion 64 of each fastener 60 is sized to prevent passage past the inner surface 28 of the connector 20. The head portion 64 of each connector 60 is furthermore configured to releasably accommodate a driving tool capable of imparting turning movements to the fastener 60. In the illustrated embodiment, the head portion 64 of each connector 60 defines a blind socket 66 that is configured to releasably accommodate a driving tool capable of imparting turning movement to the fastener 60. In a most preferred form, the blind socket 66 of fastener 60 has a hexagonal cross-sectional configuration although other like configurations would equally suffice.

To facilitate the distribution of forces and stresses across a broad area, when the connector 20 is fastened to the screws 30 and 40, the joint assembly 16 of the present invention preferably further includes a thrust washer 70 as shown in FIGS. 22 through 25. The thrust washer 70 includes an apertured plate-like member 71 defining a generally centralized bore 72 and first and second generally parallel and planar surfaces 73 and 74. Member 71 is configured to generally correspond to the shape of recess 29 provided on the interior surface 28 of each leg portion 23, 24 of connector 20. Notably, bore 72 in washer 70 is sized to allow the threaded shank portion 62 of fastener 60 to pass endwise therethrough while preventing the head portion 64 from moving therepast. As will be appreciated, when the fastener 60 is tightened to draw the respective screw 30, 40 and respective leg portions 23, 24 of connector 20 into fixed relationship relative to each other, the head portion 64 of fastener 60 acts against the washer 70 which serves to evenly distribute forces and stresses across a broader area thereby lessening the likelihood of fatigue failure of the connector 20 in the region of the fastener 60.

Returning to FIG. 3, after opposing end regions of the bones 10 and 12 have been surgically severed, the joint assembly 16 is implanted to replace and act as the distal interphalangeal joint. To begin, a probe (not illustrated) is inserted into the exposed medullary cavity of the bone to localize a suitable longitudinal axis for insertion of a respective screw 30, 40. A recess is then drilled in the exposed medullary cavity. Screws 30, 40 similar to that illustrated in FIGS. 14 through 18 are next inserted into the bone substance with the generally pointed end 43 of the screw being initially inserted into the bone substance. A suitable tool (not shown) is used to engage the trailing end 45 of member 41 to allow the surgeon to rotate the screw such that the external threading 42 of member 41 engages with the bone substance.

As shown in FIG. 3, the surgeon rotates the screw 30, 40 until the reduced diameter trailing end 44 of member 41 projects a predetermined endwise distance beyond and away from the end region of the respective bone and extends toward the opposing end region of the other bone. Turning to FIG. 7, the reduced diameter portion 44 of member 41 of each screw 30, 40 is sized to pass endwise through the bore 26 defined toward the free end of each leg portion 23, 24 of the connector 20.

Figure 8:
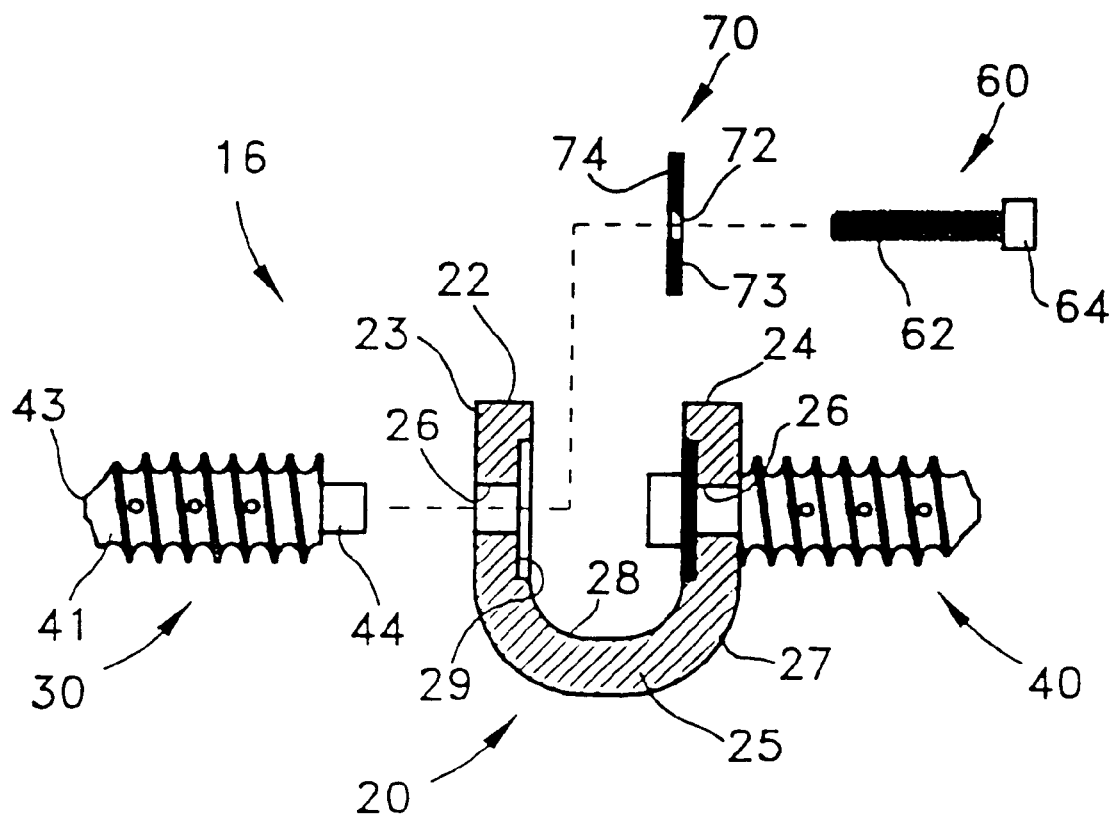
FIG. 8 is a sectional view similar to FIG. 7, but with some component parts of the joint assembly shown in disassembled relation relative to each other.
Figure 11:
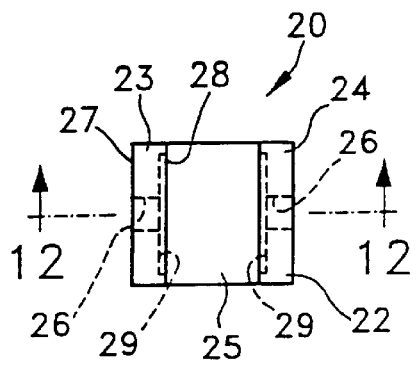
FIG. 11 is a top plan view of the component part of the invention illustrated in FIG. 10.
Figure 9:
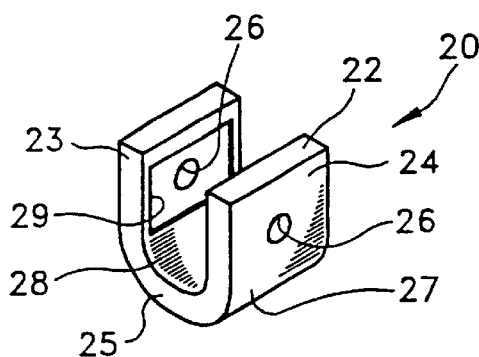
FIG. 9 is a perspective view of one of the component parts of that embodiment of the invention illustrated in FIG. 5.
Figure 10:
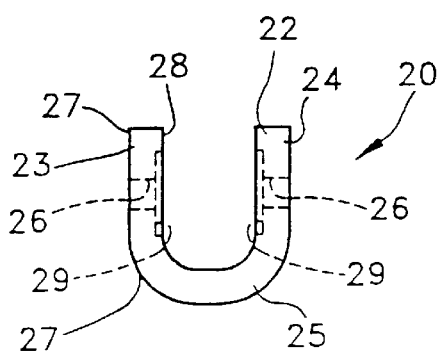
FIG. 10 is a front elevational view of that component part of the present invention illustrated in FIG. 9.
Figure 13:
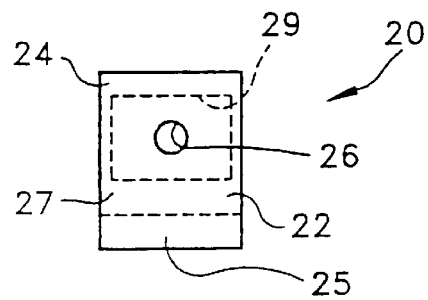
FIG. 13 is a right side elevational view of that component part illustrated in FIG. 10.
Figure 12:
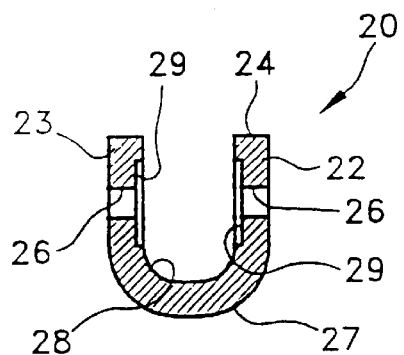
FIG. 12 is a sectional view taken along line 12—12 of FIG. 11.

Turning now to FIG. 8, and after the reduced diameter portion 44 of member 41 of screws 30, 40 is inserted endwise through the bore 26 on each leg portion 23, 24 of connector 20, the threaded shank portion 62 of fastener 60 is passed endwise through bore 72 of washer 70. The subassembly of fastener 60 and washer 70 is then fastened to the respective screw 30, 40.

Returning to FIG. 7, each fastener 60 is rotated thereby fixedly securing the leg portions of the connector 20 to the screws 30 and 40. As shown in FIG. 7, the axial length of the reduced diameter portion 44 of member 41 combined with the thickness between the planer surfaces 73, 74 (FIGS. 24 and 25) of washer 70 is equivalent to the thickness of the leg portion between the outer and inner surfaces 27 and 28, respectively, of the connector 20. Thus, the cumulative length of the reduced diameter portion 44 of member 41 and the washer 70 provides a visual indication when each leg portion 23, 24 of connector 20 is fixedly secured to the screw 30, 40.

Figure 26:
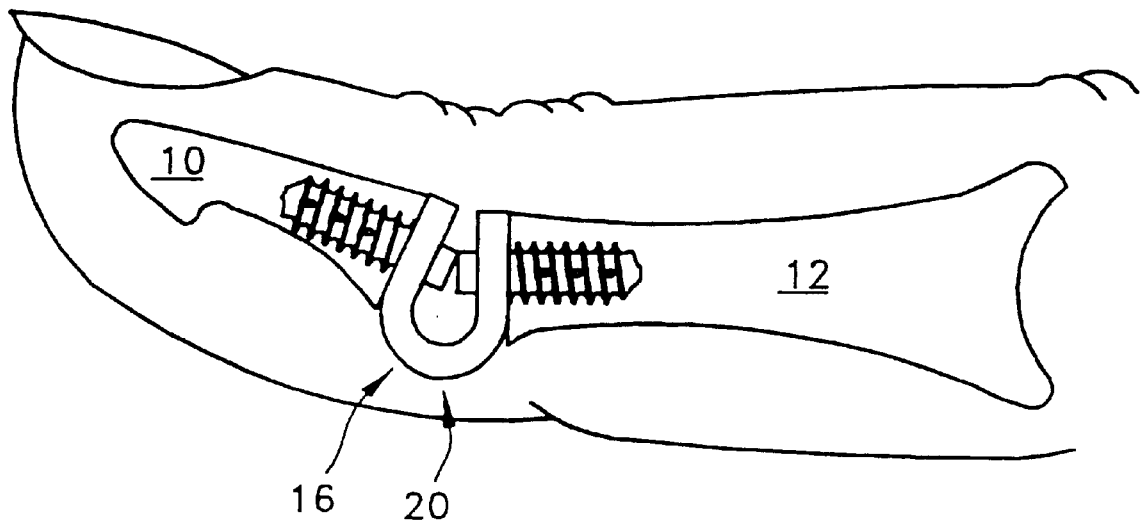
FIG. 26 is a cross-sectional view similar to FIG. 3, but showing the reconstructed joint when the finger is in an extended position.
Figure 27:
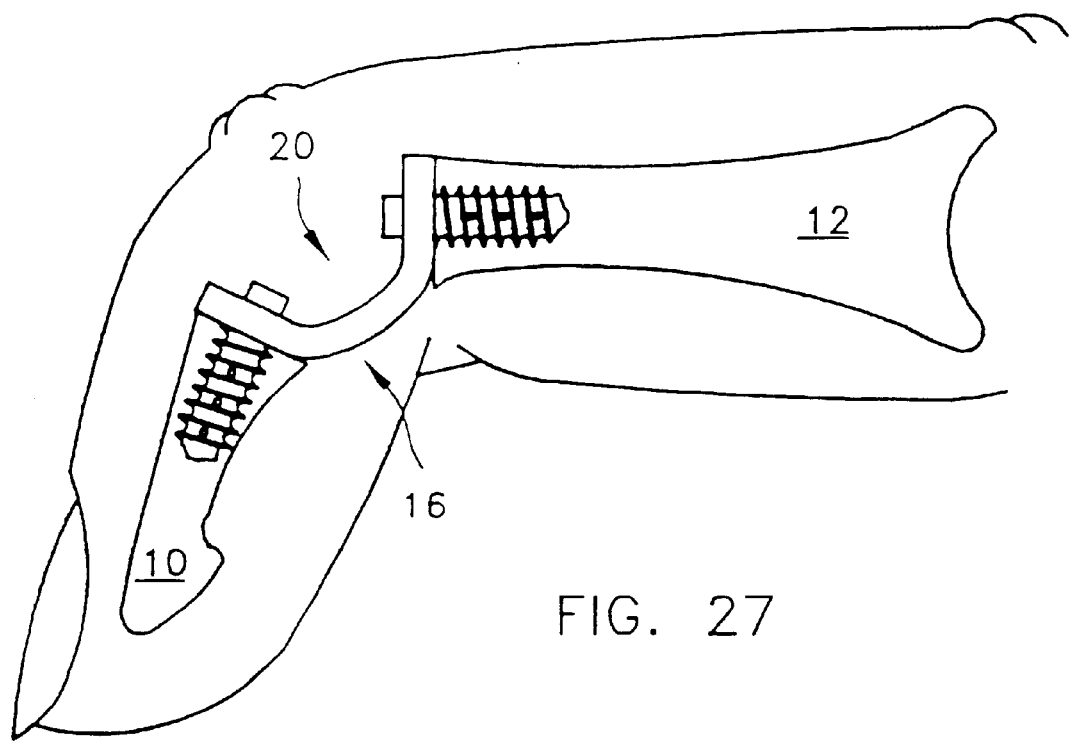
FIG. 27 is a cross-sectional view similar to FIGS. 3 and 26, but showing the reconstructed joint when the finger is in a flexed position.

Turning to FIGS. 26 and 27, the connector 20 of joint assembly 16 serves a dual purpose. First, the connector 20 of joint assembly 16 fixedly interconnects the bones 10 and 12 relative to each other. Also, the flexible connector 20 of the joint assembly 16 allows the patient's finger to bend or flex without pain and in a manner repeatedly sustaining the stresses developed while the patient bends or flexes the finger joint 16.

Figure 29:
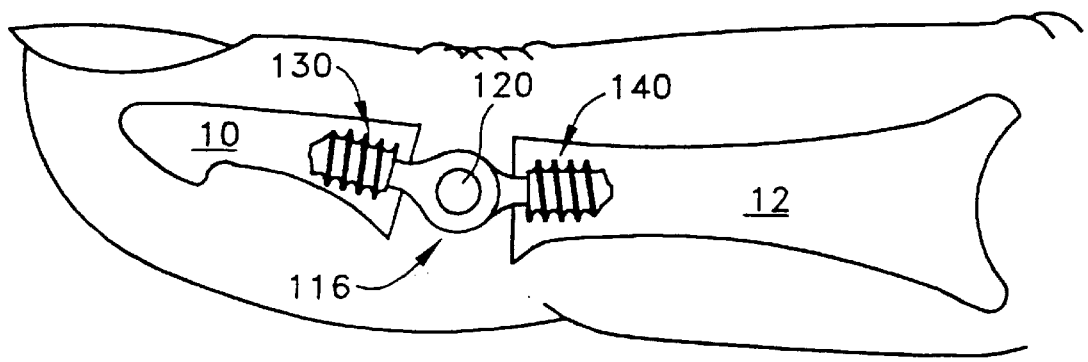
FIG. 29 is a cross-sectional view similar to FIG. 28, showing the reconstructed finger joint in an extended position.
Figure 28:
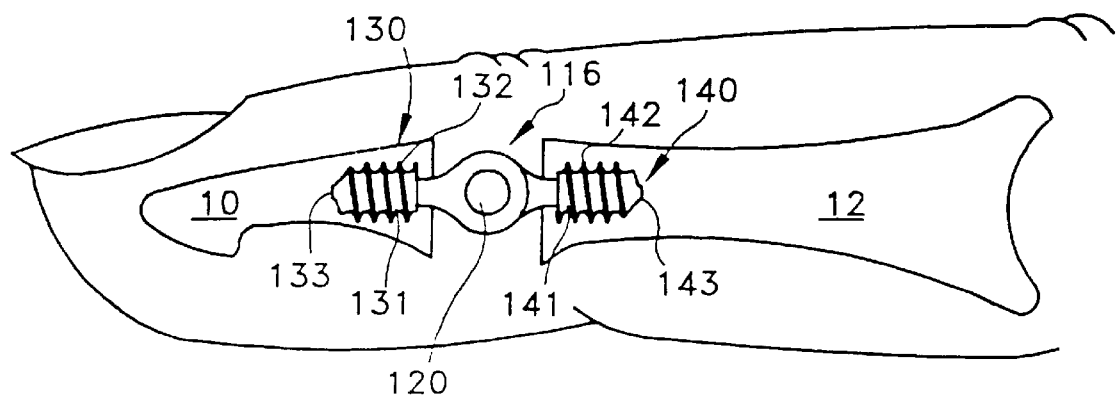
FIG. 28 is a cross-sectional view of a reconstructed finger joint in a normal position with another embodiment of the invention used to flexibly interconnect two adjacent bones.
Figure 30:
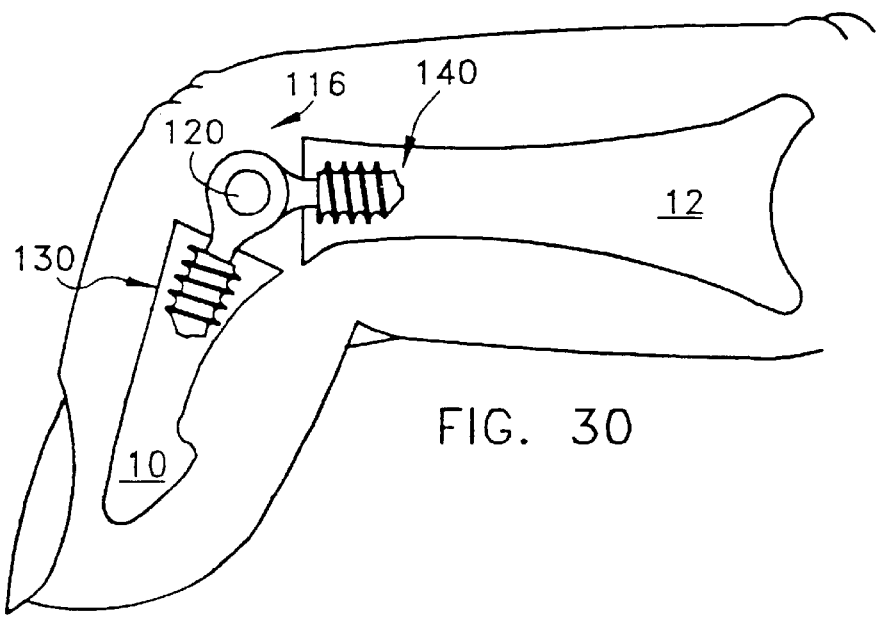
FIG. 30 is a cross-sectional view similar to FIG. 28, showing the reconstructed finger joint in a flexed position.

Another embodiment of the joint assembly according to the present invention is illustrated in FIGS. 28, 29 and 30 and is designated therein generally by reference numeral 116. The joint assembly 116 functions to fixedly and articulately secure the surgically severed bones 10 and 12 in proper relation relative to each other.

Figure 31:
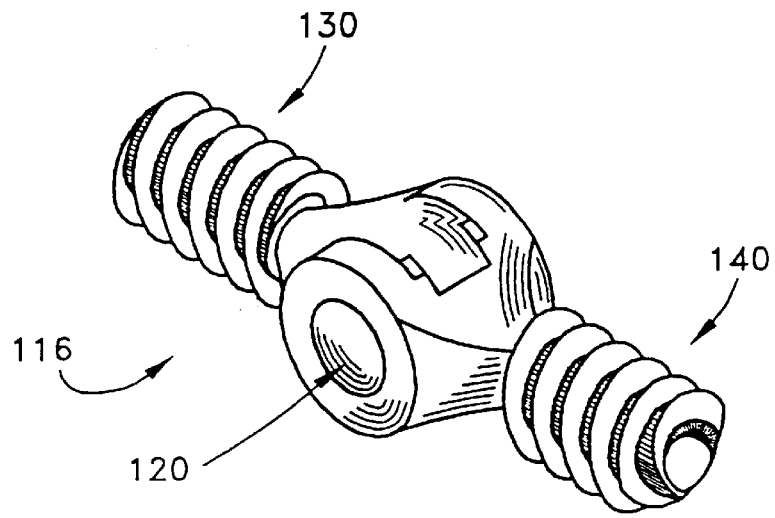
FIG. 31 is a perspective view of the embodiment of the invention illustrated in FIG. 28.
Figure 32:
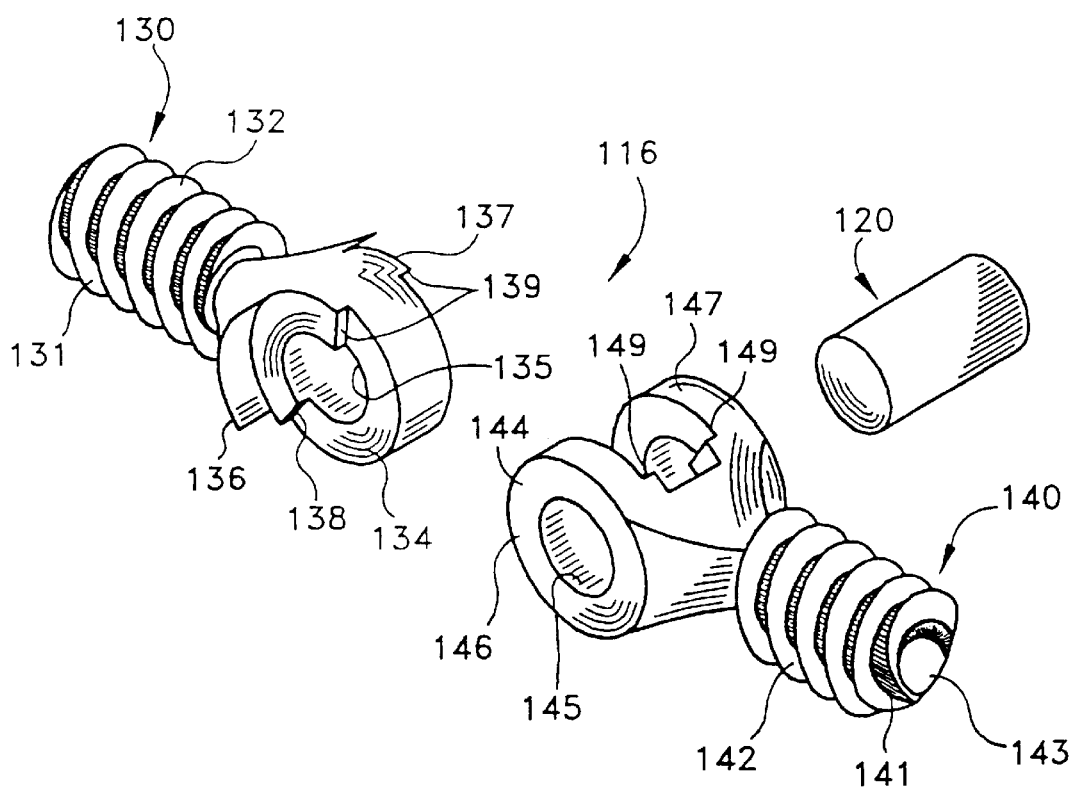
FIG. 32 is an exploded perspective view of that embodiment of the invention illustrated in FIG. 31.

As shown in FIGS. 31 and 32, this alternative embodiment of the fixation assembly 116 comprises a connector 120 for fixedly and articulately interconnecting joint ends of first and second screws 130 and 140, respectively, to each other.

Figure 34:
FIG. 34 is a top plan view of the connector illustrated in FIG. 33.
Figure 33:
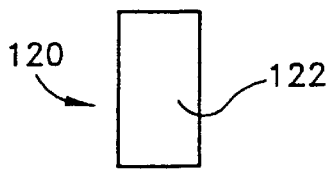
FIG. 33 is an elevational view of a connector for that embodiment of the invention illustrated in FIGS. 31 and 32.

Connector 120 of joint assembly 116 is fabricated from a material that is biocompatible with the human and bone tissue and is preferably selected from a class comprised of: ultrahigh molecular weight polyethylene or a polymer similar thereto, or nylon. As shown in FIGS. 33 and 34, connector 120 comprises a cylindrical member 122 of a predetermined length. In the preferred form of the invention, member 122 is substantially solid but it is within the spirit and scope of the present invention that the cylindrical member 122 could be formed as a cylindrical tube-like member.

Figure 36:
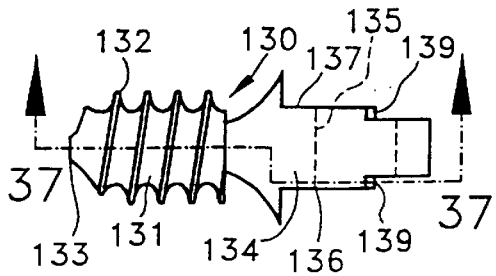
FIG. 36 is a top plan view of that component illustrated in FIG. 35.
Figure 35:
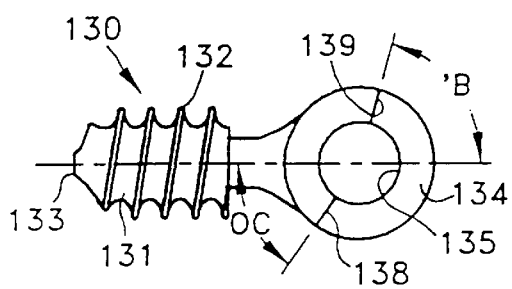
FIG. 35 is an elevational view of another component part of that embodiment of that invention schematically illustrated in FIGS. 31 and 32.
Figure 37:
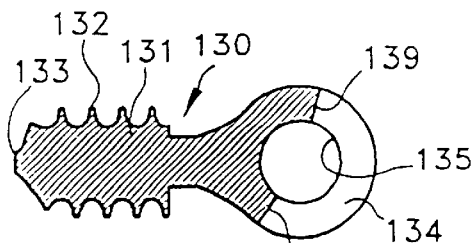
FIG. 37 is a sectional view taken along line 37—37 of FIG. 36.

As shown in FIGS. 35, 36 and 37, screw 130 comprises an elongated member 131 having external threading 132 extending axially rearwardly from a generally pointed or leading end 133 thereof. The elongated member 131 is preferably fabricated from a material that is biocompatible with the human and bone tissue and is preferably selected from a class comprised of: titanium, a titanium based alloy, stainless steel, or a cobalt chromium alloy. The external threading 132 extends axially lengthwise of member 131 and has a generally uniform pitch between leading and trailing ends thereof. The threading 132 on member 131 has a relatively coarse pitch such that a substantive holding force will be developed when the screw 130 is threadably secured within the bone substance of bone 10.

As shown, member 131 defines an eye portion 134 at the trailing end thereof. In this embodiment of the invention, the eye portion 134 of member 131 is preferably formed integrally with the remainder of member 131 and defines a cylindrical bore 135 having a closed margin defined by eye portion 134. Notably, bore 135 has a diameter which is specifically sized to establish a free or running fit relative to the connector 120 passing therethrough.

Eye portion 134 further includes two generally planar and parallel surfaces 136 and 137 preferably disposed on opposite sides of a longitudinal axis of member 131. In a most preferred form of the invention, the surfaces 136 and 137 are equally disposed relative to the longitudinal axis of member 131. Moreover, each surface 136 and 137 defines a pair of stops 138 and 139 disposed on opposite sides of the longitudinal axis of member 131. As shown in FIG. 35, stop 138 is disposed relative to the longitudinal axis of member 131 to define an included angle a therebetween. Also as shown in FIG. 35, stop 139 is disposed relative to the longitudinal axis of member 131 so as to define an included angle $\beta$ there between. In a most preferred form of the invention, the included angle measures about 60 degrees. Moreover, and in the most preferred form of the invention, the included angle $\beta$ measures about 75 to 80 degrees.

Figure 39:
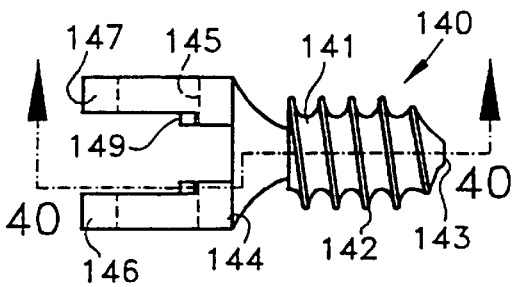
FIG. 39 is a top plan view of that component part illustrated in FIG. 38.
Figure 38:
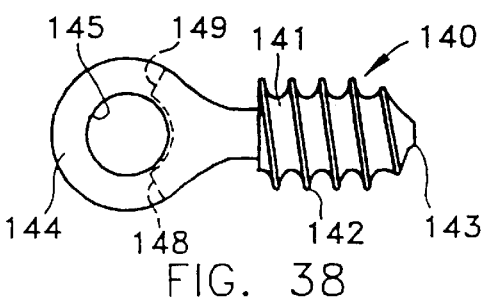
FIG. 38 is an elevational view of a component part of that embodiment of the invention illustrated in FIGS. 31 and 32.
Figure 40:
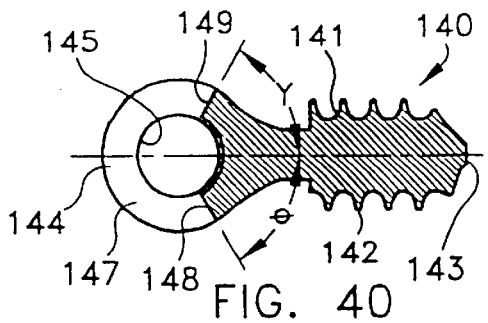
FIG. 40 is a sectional view taken along line 40—40 of FIG. 39.

As shown in FIGS. 38, 39 and 40, screw 140 comprises an elongated member 141 having external threading 142 extending axially rearwardly from a generally pointed or leading end 143 thereof. The elongated member 141 is preferably fabricated from a material that is biocompatible with the human and bone tissue and is preferably selected from a class comprised of: titanium, titanium based alloy, stainless steel, or a cobalt chromium alloy. The external threading 142 extends axially lengthwise of member 141 and has a uniform pitch between leading and trailing ends thereof. The threading 142 on member 141 has a relatively coarse pitch such that a substantive holding force will be developed when the screw 140 is threadably secured within the bone substance of bone 12.

As shown, member 141 defines an eye portion 144 at the trailing end thereof. In this embodiment of the invention, the eye portion 144 of member 141 is preferably formed integral with the remainder of member 141 and defines a cylindrical bore 145 having a closed margin defined by eye portion 144. Notably, bore 145 has a diameter that is specifically sized to accommodate the connector 120 therewithin and establish a press fit therewith.

It will be appreciated, of course, that the relationship of the members 131 and 141 relative to the connector 120 can be readily reversed without detracting or departing from the spirit and scope of the present invention. That is, the bore 145 defined by member 141 may be specifically sized to establish a free or running fit relative to the connector 120 while the bore 135 of member 131 may accommodate and establish a press fit with the connector 120. Suffice it to say, the connector 120 is maintained in position by one of the members 131, 141 while allowing the other member 131, 141 to freely rotate about the longitudinal axis of the connector 120 and for purposes of this invention it does not significantly matter which member 131, 141 turns and which member 131, 141 holds the connector 120 in position.

In the illustrated embodiment, eye portion 144 of screw 140 includes a pair of bifurcated arms 146 and 147 defined on opposite sides of the longitudinal axis of member 141. In this illustrated embodiment of the invention, and to enhance the operability of the joint assembly 116, the bifurcated arms 146 and 147 are spaced apart by a distance which is greater than the distance separating the planar surfaces 136 and 137 on the eye portion 134 of screw 130 such that a free or running fit is established between the eye portion 134 of screw 130 and the eye portion 144 of screw 140. Moreover, each bifurcated arm 146 and 147 of member 141 defines a pair of stops 148 and 149. As shown in FIG. 40, stop 148 is disposed relative to the longitudinal axis of member 141 such that an included angle θ is defined therebetween. Moreover, the stop 149 is angularly disposed relative to the longitudinal axis of member 141 such that an included angle γ is disposed therebetween. In a most preferred form of the invention, the included angle θ defined between stop 148 and the longitudinal axis of member 141 is equal to about 60 degrees. Similarly, the included angle γ defined between stop 149 and the longitudinal axis of member 141 is equal to about 60 degrees. It should be appreciated, however, that all the angles specified above are exemplary for the members 131 and 141. Ultimately, the angles defined by the screws 130 and 140 for defining or limiting angular movement of the particular joint being replaced will be determined by the individual joint requiring replacement.

Figure 41:
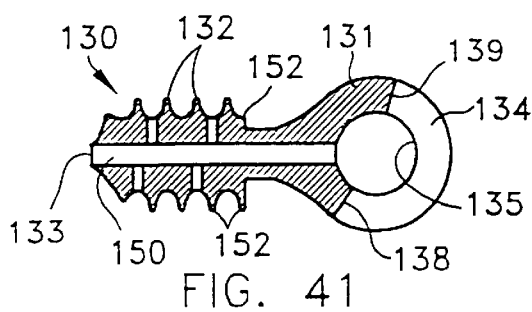
FIG. 41 is a longitudinal sectional view of an alternative embodiment of that component part illustrated in FIG. 35.

As shown in FIG. 41, member 131 may further define an elongated axial bore 150 that opens to the leading or pointed end 133 of member 131 and bore 135 of member 131. Member 131 may further define a series of radially extending bores or openings 152 that are axially spaced relative to each other along the length of member 131. As shown, each bore or opening 152 opens at one end to the throughbore 150 and opens at an opposite end to a root area of the external threading 132. The purpose of bores 150 and 152 is to allow a suitable sealant to be directed through the bores 150 and 152 and into the bone substance once the screw 30 is secured fastened within the bone. As will be appreciated, member 141 of screw 140 may be similarly configured.

Returning to FIG. 28, after opposing end regions of the bones 10 and 12 have been surgically severed or cut, the joint assembly 116 is inserted to replace and act as the distal interphalangeal joint. To begin, a probe (not illustrated) is inserted into the exposed medullary cavity of the bone to localize a suitable longitudinal axis for insertion of a respective screw 130, 140. A recess is then drilled in the exposed medullary cavity. The screw 130, similar to that illustrated in FIGS. 32, 35, 36 and 37, is next inserted into the bone substance with the generally pointed end 133 being initially inserted into the bone substance. As the screw 130 is turned, the external threading 132 of member 131 engages with the bone substance.

Screw 140, similar to that illustrated in FIGS. 32, 38, 39 and 40, is then inserted into the bone substance of bone 12 with the generally pointed end 143 being initially inserted into the bone substance. As will be appreciated, the external threading 142 of member 141 engages with the bone substance of bone 12.

As shown in FIG. 28, the surgeon rotates the screws 130 and 140 until the bores 135 and 145 of screws 130 and 140, respectively, project a predetermined endwise distance beyond and away from the end region of the respective bone and align relative to each other. Thereafter, the connector 120 is positioned through the bores 135 and 145 thereby fixedly and articulately interconnecting the screws 130 and 140 and the bones 10 and 12, respectively, to each other.

Figure 42:
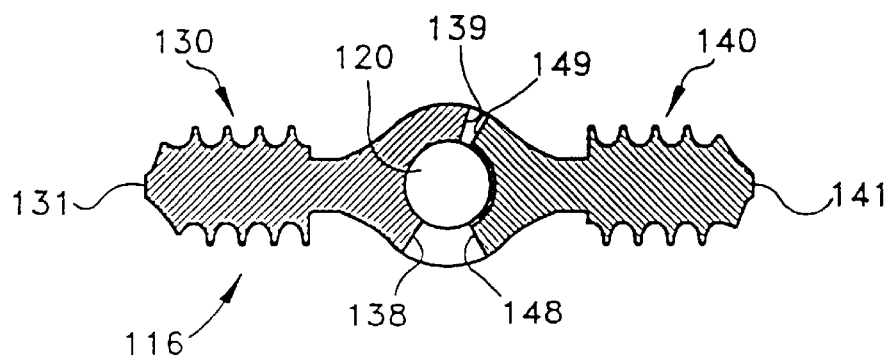
FIG. 42 is a sectional view showing the interconnected parts of that embodiment of the invention shown in FIGS. 31 and 32 in cross section and in an position similar to that which they would assume when the patient's finger is disposed as in FIG. 28.

As seen in FIG. 42, as long as the patient's finger remains in its normal position (FIG. 28), the stops 138, 139 and 148, 149 on screws 130 and 140, respectively, have no affect on the joint assembly 116. The stops 138, 139 and 148, 149 on screws 130 and 140, respectively, are angularly positioned relative to each other to limit the arcuate movement of the screws 130 and 140 and the bones attached to each 10 and 12, respectively, relative to each other.

Figure 43:
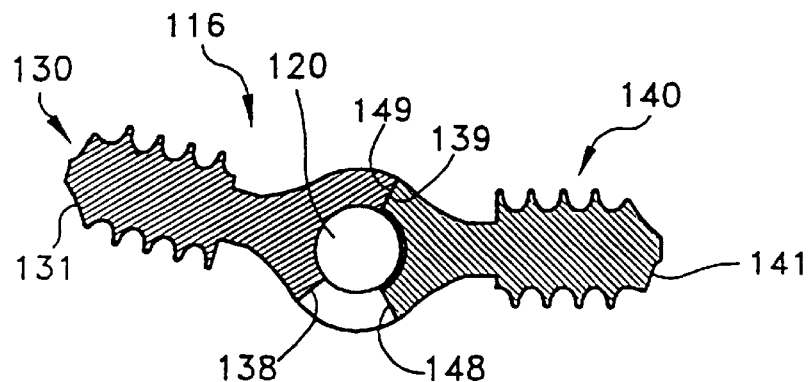
FIG. 43 is a sectional view of those component parts of an embodiment of the invention disposed angularly relative to each other as when the patient's finger is flexed, as shown in FIG. 29.

As seen in FIG. 43, when the patient flexes or bends the distal end of the digit implanted with the artificial joint assembly 116 upwardly (FIG. 29), the stops 139 and 149 on screws 130 and 140, respectively, move into an abutting relationship relative to each other. Accordingly, the joint 116 and the bones 10 and 12 attached thereto are limited by the stops 139 and 149 moving into an abutting relationship to each other. Notably, the stops 138 and 148 on screws 130 and 140, respectively, have no affect when the finger joint flexes in the direction shown in FIG. 29.

Figure 44:
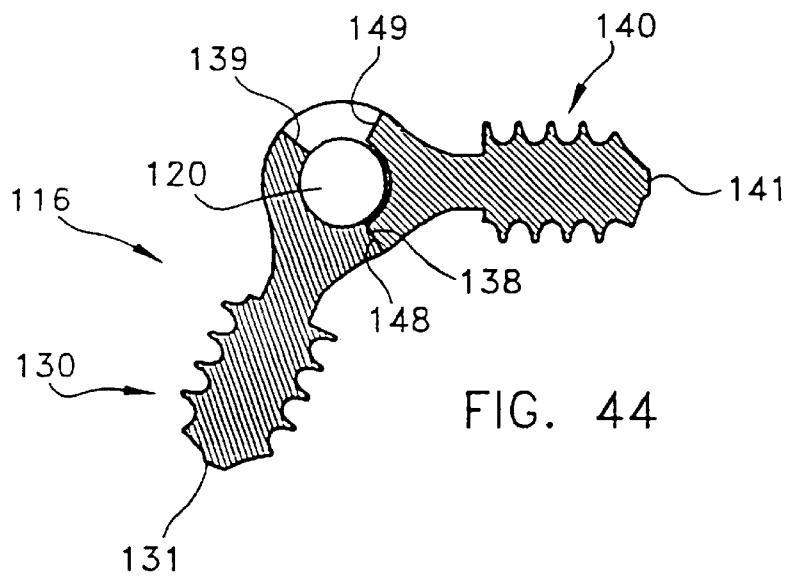
FIG. 44 is a sectional view of the interconnected component parts of the alternative embodiment of the present invention as they would angularly assume relative to each other when the patient's finger is flexed, as in FIG. 30.

As seen in FIG. 44, when the patient flexes or bends the digit implanted with the artificial joint assembly 116 as shown in FIG. 30, the stops 138 and 148 on screws 130 and 140, respectively, come into an abutting relationship relative to each other thereby limiting further movement of the finger joint and the bending of the patient's finger. Notably, when the patient bends or flexes the joint in the direction shown in FIG. 30, limit stops 139 and 149 on screws 130 and 140 have no affect on the joint assembly 116.

Figure 46:
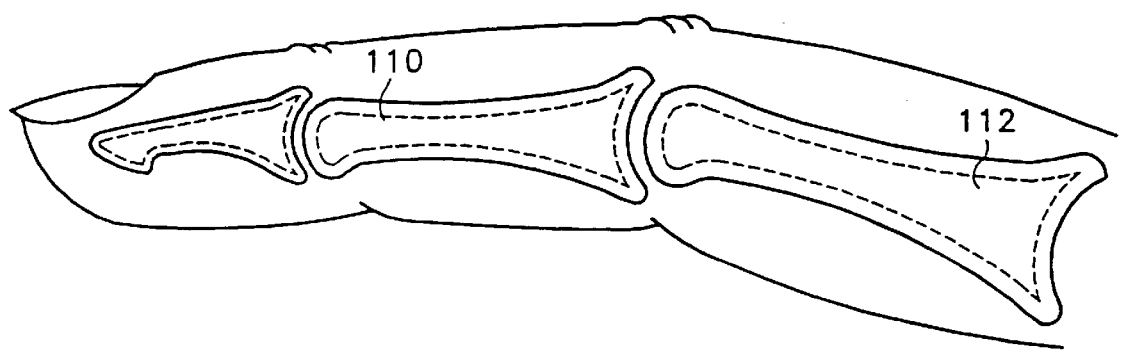
FIG. 46 is a cross section of a proximal interphalangeal joint of a patient's fingers.
Figure 47:
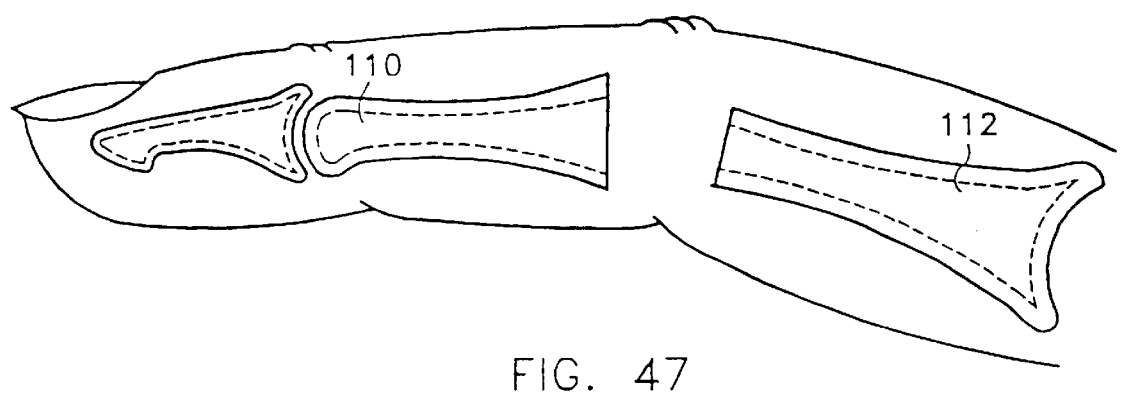
FIG. 47 shows the proximal interphalangeal joint with the opposing end regions of the bones to be interconnected following a surgical procedure being performed thereto.
Figure 45:
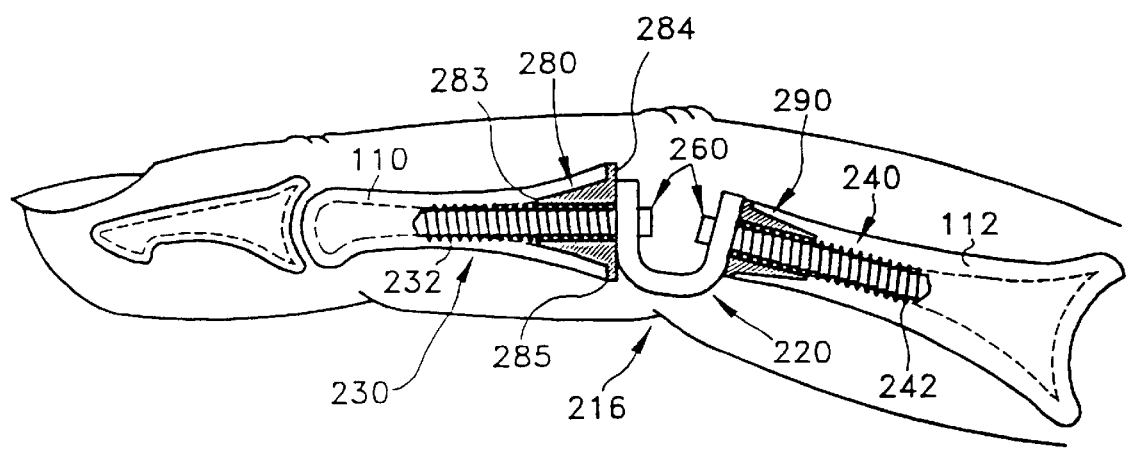
FIG. 45 is a view similar to FIG. 46, but showing an alternative form of the present invention used as a proximate interphalangeal joint.

Another embodiment of the joint assembly according to the present invention is shown in FIG. 45 as forming an artificial interphalangeal joint between bones 110 and 112. The FIG. 46 schematically illustrates the bones 110 and 112 prior to insertion of the artificial joint assembly. Again, the proximal interphalangeal finger joint, shown in FIG. 45 through 47, is a model wherein the joint assembly of the present invention can be utilized but the present invention should not be considered to be limited to finger joints. As shown in FIG. 47, prior to insertion of the joint assembly of the present invention therebetween, abutting end portions of the first and second bones 110 and 112, respectively, are surgically severed or cut thus exposing the medullary cavity therewithin.

The alternative embodiment of the joint assembly illustrated in FIG. 45 is designated generally by reference number 216. The joint assembly 216 functions to fixedly and articulately connect the surgically severed bones 110 and 112 in proper relation relative to each other. The elements of this alternative embodiment of the implantable joint assembly that are identical or functionally analogous to those components mentioned above with respect to the finger joint 16 are designated by reference numerals identical to those used above with the exception that this embodiment referenced numerals are in the 200 series.

Turning to FIG. 48, this alternative embodiment of the joint assembly 216 comprises a connector 220 for fixedly and articulately interconnecting joint ends of first and second screws 230 and 240, respectively, to each other. The connector 220 shown in FIGS. 48 and 49 is substantially similar to the connector 20 illustrated in FIGS. 9 through 13. Thus, no further detailed description need be provided thereto at this time. Suffice it to say, connector 220 includes flexibly interconnected leg portions 223 and 224 that each define a bore 226 toward a free end thereof.

In this embodiment of the invention, the first and second screws 230 and 240, respectively, are substantially identical. Moreover, and with exception to their length and possibly their diameter, each screw 230, 240 is substantially similar to screw 40 described above with reference to FIGS. 14 through 18. Thus, no further detailed description need be provided at this time. Suffice it to say, each screw 230, 240 includes an externally threaded portion 242 and a reduced diameter portion 244.

Figure 21:
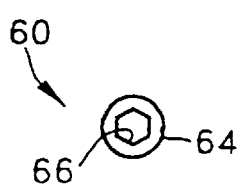
FIG. 21 is a left end view of the component part illustrated in FIG. 19.

The illustrated embodiment of the joint assembly 216 further comprises a pair of fasteners 260 for interconnecting the respective leg portion of the connector 220 to the respective screw 230, 240. Each fastener 260 of this alternative embodiment of the joint assembly is substaitially similar to the fastener 60 shown in FIGS. 19 through 21. Thus, no further description need be provided at this time.

To facilitate the distribution of forces and stresses, the joint assembly 216 further utilizes thrust washers 270. As shown, one thrust washer 270 is operably associated with each fastener 260. The thrust washer 270 is substantially similar to the washer 70 illustrated in FIGS. 22 through 25. Thus, no further description need be provided at this time.

This alternative embodiment of the joint assembly 216 further includes first and second grommets 280 and 290, respectively. Notably, and in accordance with another aspect of the present invention, the grommets 280, 290 are intended to be provided in a plurality of different sizes. As will be appreciated, the various size grommets allow the surgeon to select a grommet that is sized to fit particularly well within the specific medullary cavity of the particular patient thereby advantageously stabilizing the joint assembly 216 relative to the end regions of bones 110 and 112 that are to be articulately joined relative to each other. As will be described below, the grommets 280 and 290 are specifically designed and/or configured to promote boney ingrowth. Thus, and while each screw 230, 240 serves to initially fasten the joint assembly 216 in place, the grommets 280, 290 of the joint assembly 216, along with the boney ingrowth associated therewith, serve to securely fasten the joint assembly 216 in place for long term use.

As will be appreciated, and as mentioned, the specific sizes of the grommets 280, 290 can vary relative to each other. The intended function, purpose, and overall configuration of the grommets 280, 290 are, however, identical. Since the intended function, purpose, and overall configuration of the grommets 280, 290 are preferably identical, only grommet 280 will be discussed in detail with the understanding that the grommet 290 is substantially identical thereto.

The grommets used in combination with the joint assembly 216 is best illustrated in FIGS. 50 through 54. Each grommet 280, 290 is preferably formed from a material chosen from the class including: titanium, titanium alloy, stainless steel, a cobalt chromium alloy, ceramic, or other suitable material that promotes boney ingrowth. As shown therein, grommet 280 includes an axially elongated member 281 having a bore 282 extending between opposite end portions 283 and 284. Notably, the throughbore 282 is specially sized to fit over the external threading 232 and 242 provided axially along the length of each screw 230 and 240, respectively. As shown in FIG. 45, end portion 283 of the respective grommet is adapted to be initially inserted into the medullary cavity of the severed bone fragment and is, accordingly, of a smaller diameter than end portion 284. A stop flange 285 is preferably provided on each grommet 280, 290 to limit axial insertion or endwise movement of the grommet within the medullary cavity of the severed bone fragment.

As shown in FIG. 51, the end portion 283 of each grommet 280, 290 preferably has a generally circular cross-sectional configuration that tapers outwardly to end portion 284 having a larger and preferably rectangular cross-sectional configuration. Suffice it to say, the grommet selection is chosen by which grommet configuration most closely corresponds to or proximates the inner endosteal surface configuration of the severed bone fragment. Moreover, the outer surface of each grommet 280, 290 extending between the opposed end portions 283, 284 is preferably treated to promote boney ingrowth. That is, the outer surface configuration of each grommet 280, 290 has a burnished surface finish or a cancerous micron pore size ranging between about 100 and about 450 microns to promote bonzy ingrowth with the surrounding bone tissue.

Figure 55:
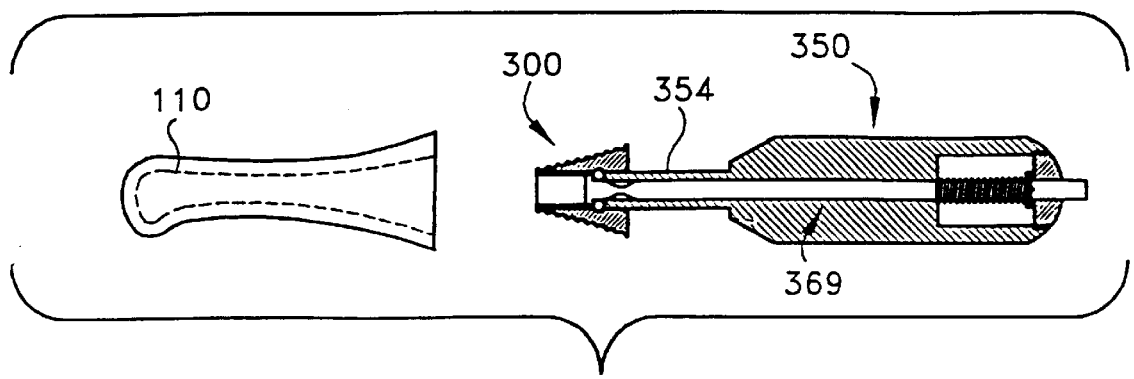
FIG. 55 is a partial sectional view showing a tool with a broach connected thereto.
Figure 56:
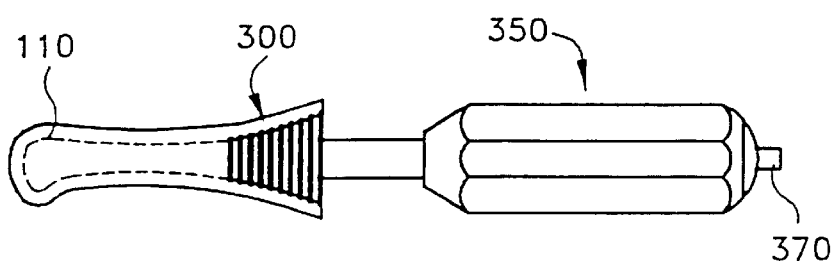
FIG. 56 is an elevational view similar to FIG. 55 showing the tool being used to insert the broach into the medullary cavity of the bone.

As mentioned above, prior to implantation of the artificial joint assembly 216, opposing end regions of the bones 110 and 112 are surgically severed to expose the medullary cavity of each bone 110, 112 (FIG. 47). As shown in FIGS. 55 and 56, the surgeon uses a broach 300 to manually shape the inner surface of each bone 110, 112. To facilitate the surgeon's use of the broach 300, a suitable tool 350 is provided. Preferably, tool 350 is capable of releasably holding the broach 300 at a distal end thereof.

FIGS. 57 through 61 illustrate the broach 300. As shown, broach 300 includes an axially tapered member 302 having a generally rectangular configuration at a proximal end 304 thereof and a generally circular configuration at a distal end 306 thereof. Suffice it to say, the outer configuration of broach member 302 closely proximates or corresponds to the shape of the inner endosteal surface of the bones 110 and 112. As is conventional, broach 300 has a plurality of closely adjacent and raised cutting edges 308 that peripherally extend about the axially tapered outer configuration thereof. That is, the cutting edges 308 proximate the contour of the outer surface of the broach 300 and, therefore, will taper from an approximately rectangular configuration toward the proximal end 304 of the broach 300 to an annular configuration toward the distal end 306 of the broach 300.

Figure 60:
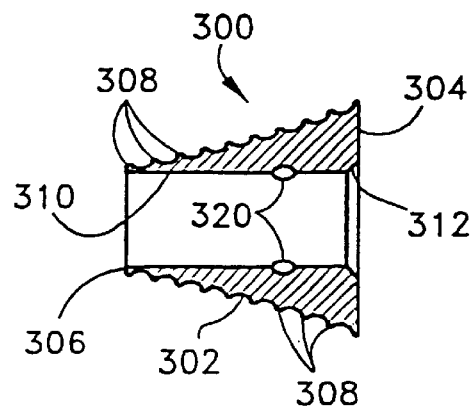
FIG. 60 is a longitudinal sectional view taken along line 60—60 of FIG. 59.
Figure 59:
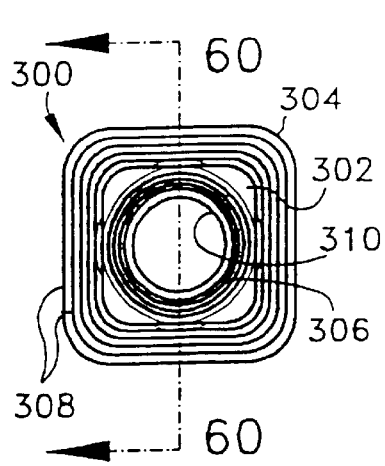
FIG. 59 is a left-end view of the broach illustrated in FIG. 58.
Figure 58:
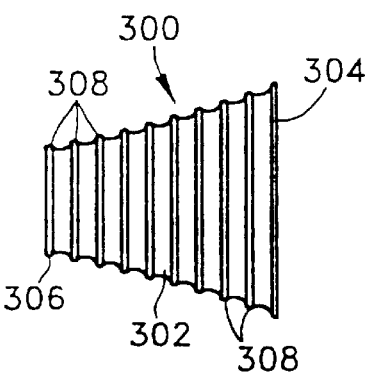
FIG. 58 is an elevational view of the broach illustrated in FIG. 57.
Figure 61:
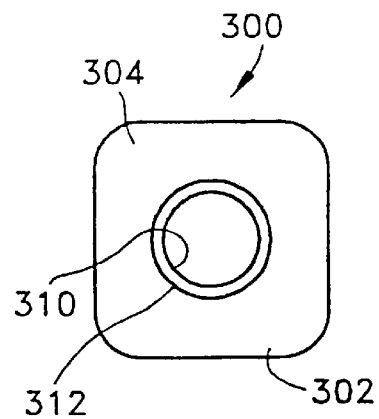
FIG. 61 is a right-end view of the broach illustrated in FIG. 58.
Figure 62:
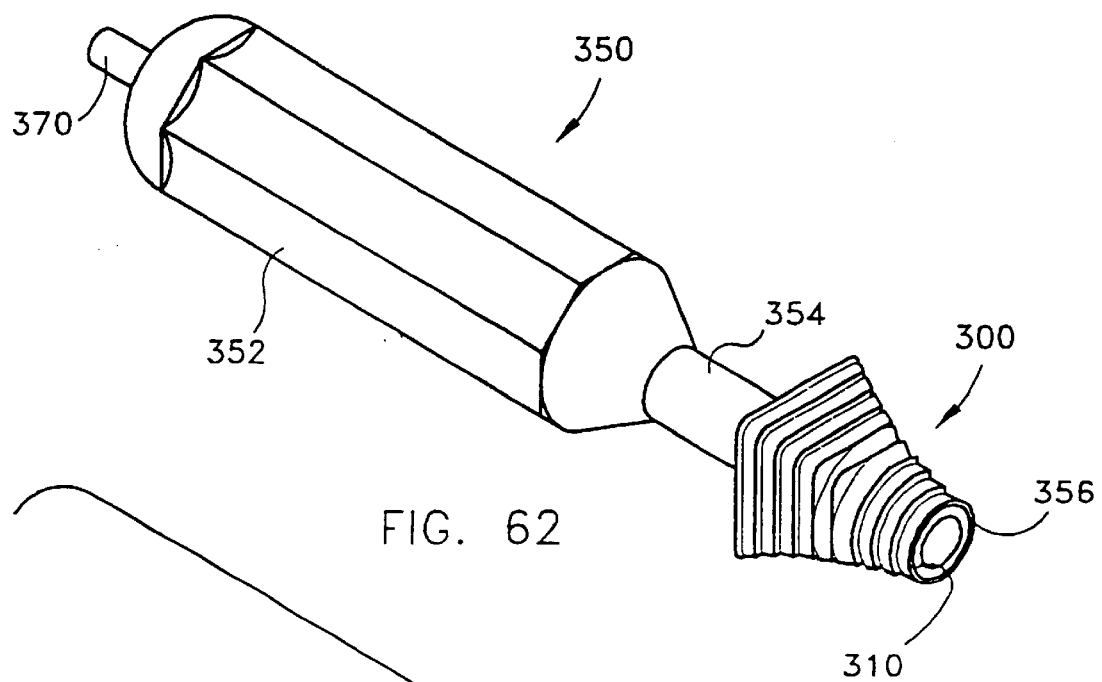
FIG. 62 is an enlarged perspective view showing a tool with a broach as illustrated in FIGS. 57 through 61.

As shown in FIGS. 57, 59, 60 and 61, broach member 302 further includes a generally coaxial bore 310 that opens to the proximal end 304 of broach 300 and preferably to the distal end 306 thereof. In a most preferred form of the invention, an annular chamfer 312 is provided in combination with an inlet end of bore 310 to guide the tool 350 into a releasable locking relationship with the broach 300. Moreover, and as shown in FIG. 60, intermediate opposite ends thereof, bore 310 defines a plurality of recesses 320 arranged circumferentially about the bore 310.

As shown in FIG. 63, the tool or instrument 350 is designed to releasably carry the broach 300 toward a distal end thereof. In its illustrated form, and although other devices may equally suffice, the tool or instrument 350 includes a handle 352 having a first tubular projection 354 extending from a forward end thereof and with a second tubular projection 356 extending forwardly from the first projection 354. Notably, the projections 354 and 356 have a substantially constant outside diameter. Moreover, the outside diameter of the projections 354 and 356 is substantially equal to the inside diameter of the bore 310 in the broach 300. The handle 352 and projections 354, 356 are each structurally joined to each other such that manual manipulation of the handle 352 will likewise effect movement of the projections 354 and 356.

As shown in FIG. 63, handle 352 and projection 354 combine to define an axially elongated substantially constant diameter bore 360. Projection 356 also defines an axially extending bore 362 that is aligned and communicates with bore 360. Bore 362 defined by u projection 356 has a larger diameter than does bore 360 and, thus, an annular shoulder 364 is defined therebetween. Moreover, a series of radially disposed apertures 366 are defined at a proximal end of projection 356. Each radial opening or aperture 366 opens to bore 362 and to the periphery of projection 356.

The tool or instrument 350 further includes a locking mechanism 369 for releasably locking the broach 300 to a distal end of the tool 350. In the illustrated embodiment, the locking mechanism 369 includes an actuator 370 preferably in the form of an axially elongated rod 371 that is slidably mounted for endwise movement within bore 360 of handle 352. Rod 371 has an enlarged end 372 at the foremost forward end thereof. As shown, the enlarged end 372 is sized to slidably move endwise within bore 362 defined by projection 356. The opposite end of rod 370 is guided by an apertured cap 374 provided at and forming an end portion of handle 352. As shown in FIG. 63, and as long as the locking mechanism 369 is conditioned to releasably hold a broach 300 at a free end of the tool 350, the free end of rod 371 projects axially beyond the end of handle 350 for engagement by the surgeon.

Figure 64:
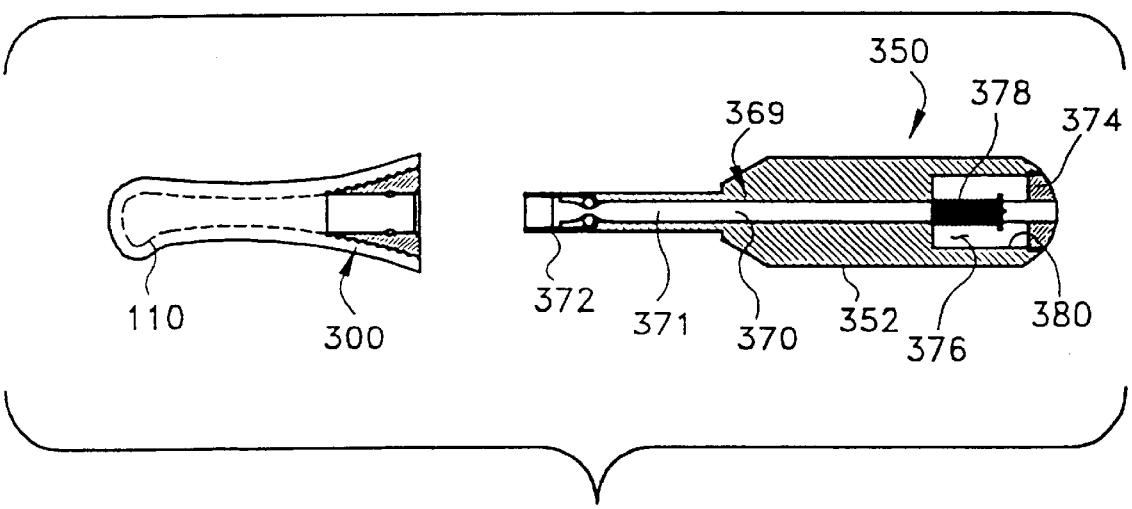
FIG. 64 is a sectional view showing the broach situated in the medullary cavity of the bone and released from the tool.
Figure 57:
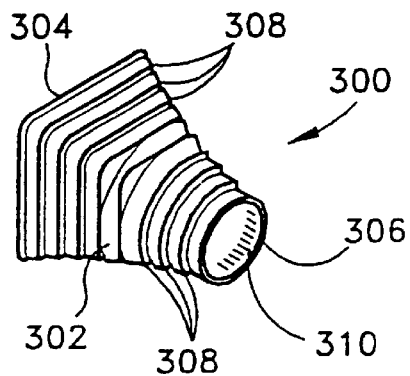
FIG. 57 is an enlarged perspective view of the broach illustrated in FIGS. 55 and 56.

As shown in FIGS. 63 and 64, intermediate opposite ends thereof, rod 371 is resiliently biased in the direction of arrows 376. Preferably, a compression spring 378 is suitably arranged within a cavity 380 defined by handle 352 and is operably coupled to and resiliently biases the rod 371 in the direction of arrows 376 with the free end of the rod 371 projecting outwardly from the handle 352. The enlarged head end 372 of rod 371 operably engages with the annular shoulder 364 to limit the axial movement of the rod 371 in the direction of arrows 376.

At its forward end and spaced axially from the enlarged head end 372, rod 371 is provided with an annular recess 384 having cam surfaces 386 and 388 extending therefrom. Notably, when rod 371 is in the locked position shown FIG. 63, the recess 384 and camming surfaces 386 and 388 are axially disposed away from the radial holes or apertures 366 defined by the projection 356.

Figure 65:
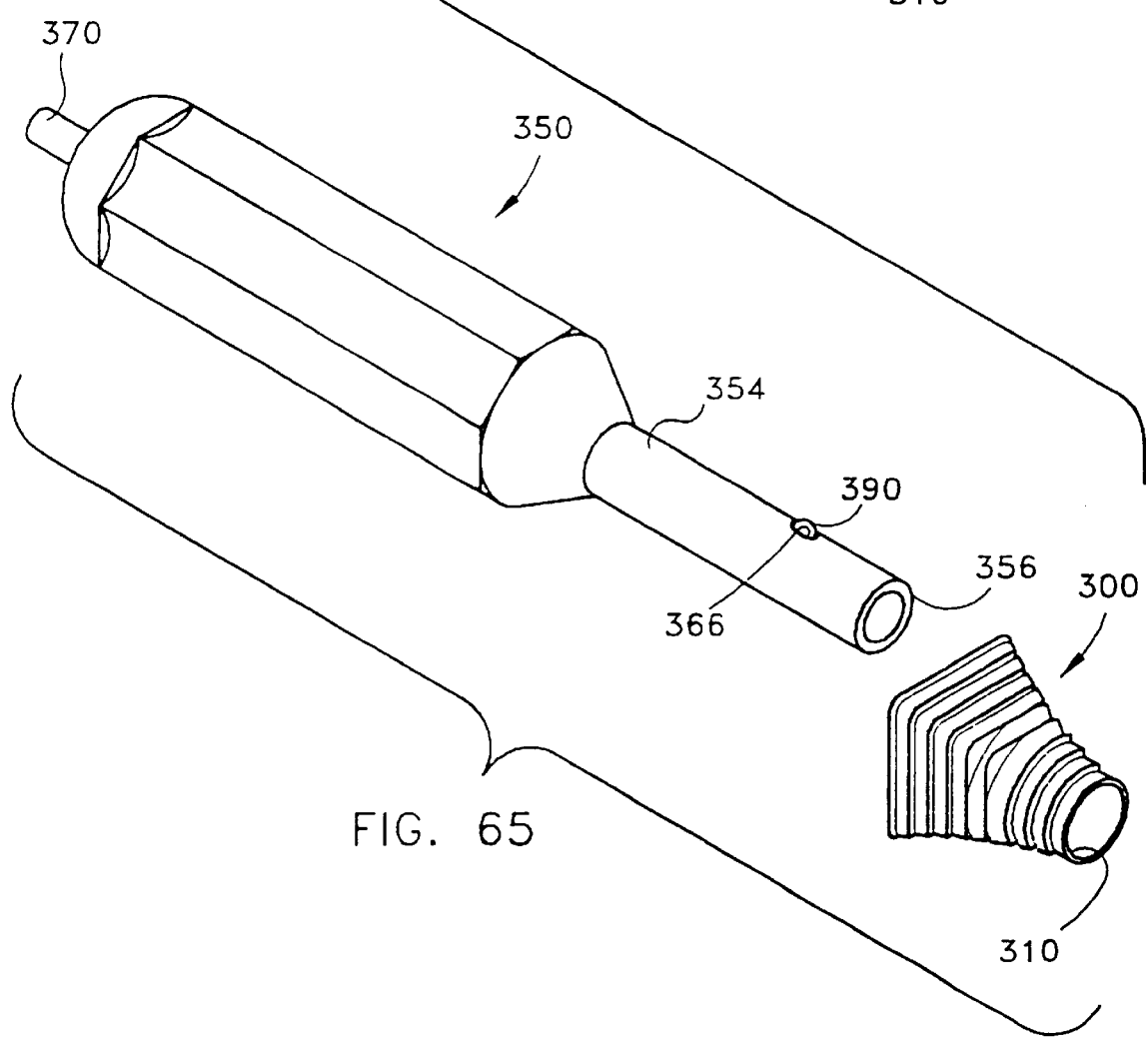
FIG. 65 is an enlarged perspective view similar to FIG. 62 showing the broach illustrated in FIGS. 57 through 61 released from the distal end of the tool.

The locking instrumentality 369 of the tool or instrument 350 further includes a plurality of spherical locking balls or detents 390 that are configured to combine with the recesses 320 defined on the interior of the bore 310 of broach 300 thereby releasably holding the broach 300 to the tool or instrument 350. As shown in FIGS. 63 and 65, the balls or detents 390 are specifically sized to extend at least partially through the apertures 366 defined by projection 356. Notably, the apertures 366 defined by projection 356 are suitably configured or staked to prevent the balls or detents 390 from becoming disassociated from the tool 350.

As long as the locking mechanism 369 is in the position shown in FIGS. 63 and 65, the exterior of the rod 371 combines with the headed end 372 to forcibly move the detents 390 radially outwardly. To allow the detents 390 to retract, thereby conditioning the locking mechanism to an unlocked position, and as shown in FIG. 66, the actuator 370 is depressed by the surgeon. That is, the free end of the rod 371 projecting beyond the handle 352 is axially moved against the action of spring 378 to align the recess 384 on rod 371 with the detents 390. The recess 384 is configured to allow the detents 390 to retract sufficiently such that the broach 300 is released from its locked association with the tool or instrument 350. As will be appreciated, when the force urging the actuator 370 against the action of spring 378 is released, the locking mechanism is automatically returned to a locked condition under the influence of spring 378 which automatically returns the rod 371 to the position shown in FIG. 63 and the camming surface 386 serves to forcibly urge the detents 390 outwardly through the apertures 366 to the position shown in FIGS. 63 and 65.

Returning to FIGS. 55 and 56, the broach 300 is shown affixed to the distal end of the tool or instrument 350 and is manually manipulated to configure or shape the inner surface of each bone 110 and 112. After the inner endosteal surface of the bones 110 and 112 has been broached, the locking mechanism 369 on handle 352 is unlocked by moving the rod 371 into the position shown in FIGS. 64 and 66 thereby allowing the tool 350 to be disconnected from the broach 300 whereby leaving the broach 300 remaining within the medullary cavity of the bone as shown in FIG. 64.

Figure 67:
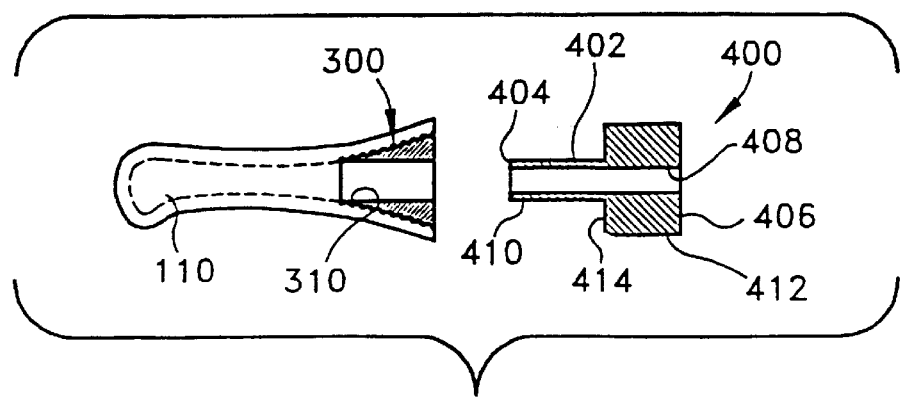
FIG. 67 is a view similar to FIG. 64 showing a drill guide adapted for insertion within the broach.
Figure 68:
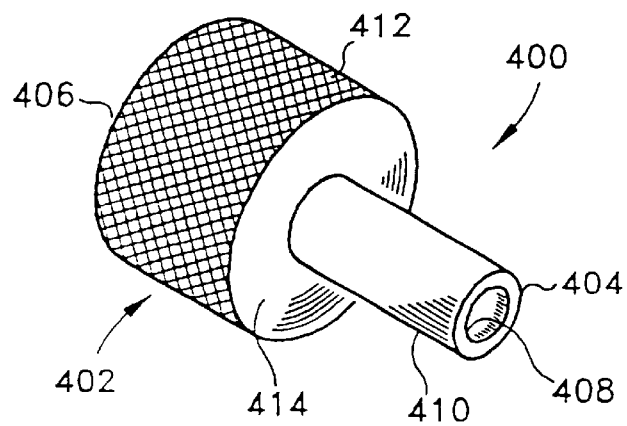
FIG. 68 is an enlarged perspective view of the drill guide illustrated in FIG. 67.
Figures 69, 70, 72:
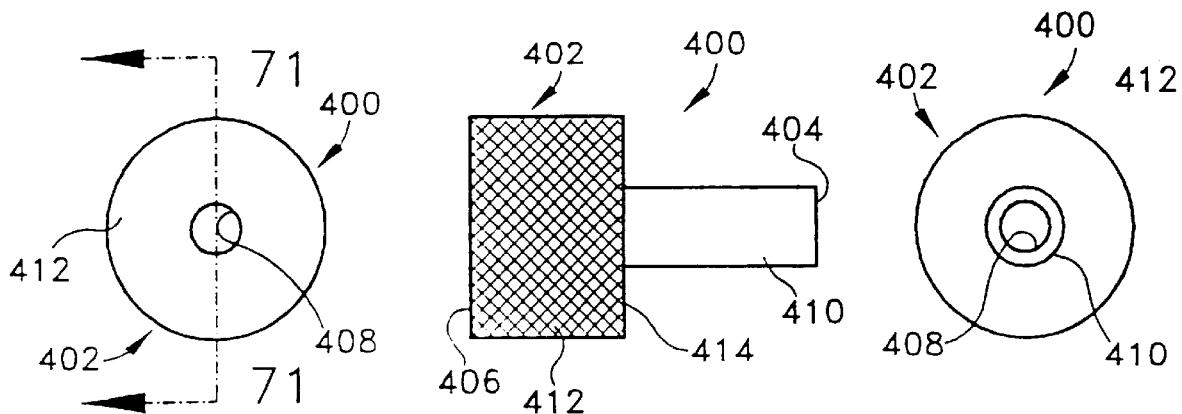
FIG. 69 is an elevational view of the drill guide illustrated in FIG. 68.
FIG. 70 is a left-end view of the drill guide illustrated in FIG. 68.
FIG. 72 is a right-end elevational view of the drill guide illustrated in FIG. 68.
Figure 71:
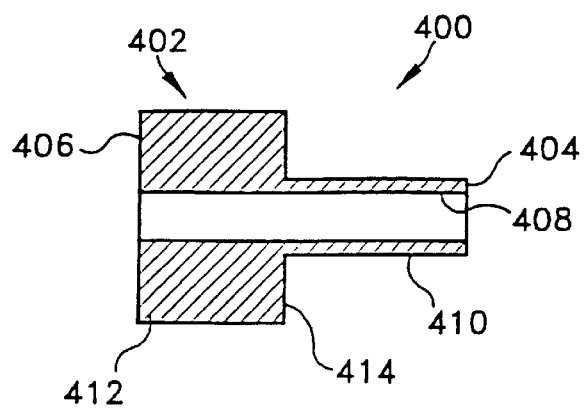
FIG. 71 is a sectional view taken along line 71—71 of FIG. 70.

Turning to FIG. 67, a drilling guide 400 is then inserted into the bore 310 of the broach 300 that is positioned at the severed end of the bone.

One form of drilling guide 400 is shown in FIGS. 68 through 72. Guide 400 preferably includes an axially elongated and hardened member 402 having a distal end 404 and a proximal end 406 with a bore 408 opening to opposite ends 404 and 406. Guide 400 is configured with a reduced diameter axially extending guide portion 410 and an enlarged handle portion 412. The guide portion 410 has an outside diameter sized to slide endwise into and be positioned within the inside diameter of bore 310 (FIG. 60) of broach 300. Handle portion 412 defines an annular shoulder 414 relative to guide portion 410.

Figure 73:
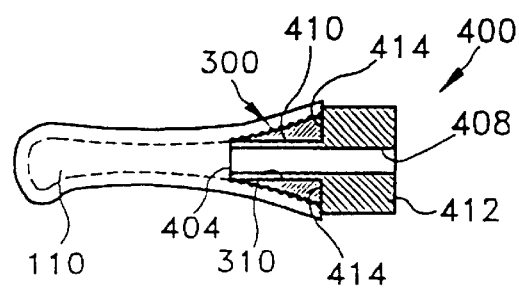
FIG. 73 is a view similar to FIG. 67 showing the drill guide arranged in place.

As shown in FIG. 73, the guide portion 410 is initially inserted into the bore 310 of broach 300. The guide portion 410 is configured to move along bore 310, until the shoulder 414 of handle 412 engages the end of broach 300.

Figure 74:
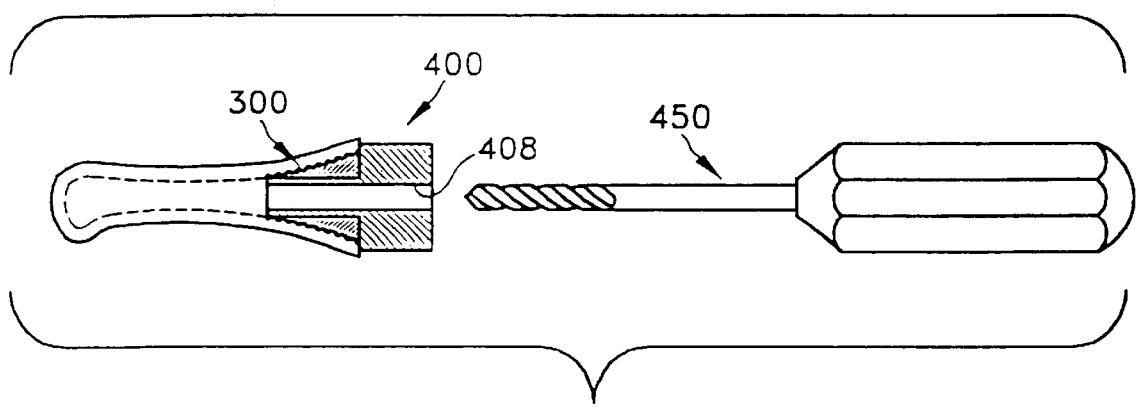
FIG. 74 is a view similar to FIG. 73 showing a drill aligned for insertion into and through the drill guide.
Figure 75:
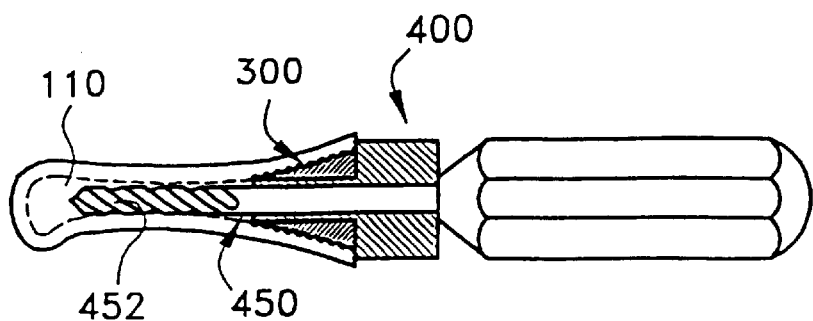
FIG. 75 shows the drill being fully inserted within the medullary cavity of the bone.

As shown in FIG. 74, a conventional drill 450 is then aligned with the throughbore 408 defined by the drill guide 400. As shown in FIG. 75, the drill 450 is operated to provide a suitably sized bore 452 in the bone substance of bone 110. After the bore 452 is provided in the bone substance of bone 110, drill 450 is removed from the guide 400 and the guide 400 is removed from the bore 310 of the broach 300.

Figure 76:
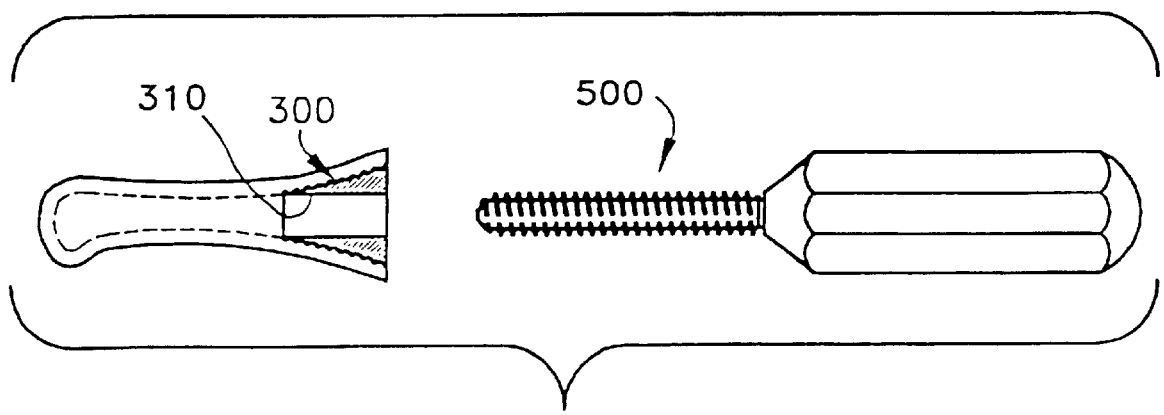
FIG. 76 is a view showing a tap being arranged for insertion through the drill guide and within the medullary cavity of the bone.
Figure 77:
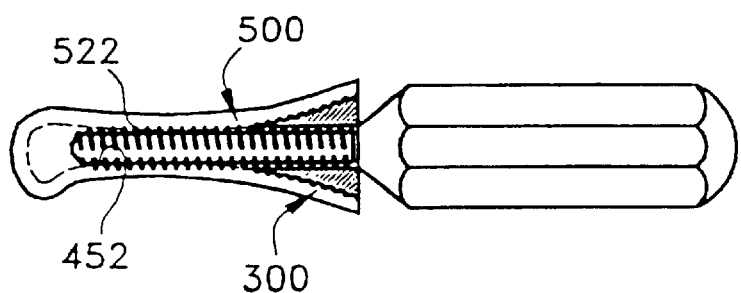
FIG. 77 is a view similar to FIG. 76, but showing the tap fully inserted through the guide and within the medullary cavity of the bone.

Next, a conventional tap 500 is passed through the internal bore 310 of the broach 300 as shown in FIG. 76. As shown in FIG. 77, the tap 500 passes into the suitably shaped and sized bore 452 provided by the drill 450 so as to provide internal threading for a substantial axial distance along the bore 452 provided by drill 450. The internal threading 522 provided by tap 500 is of like hand and corresponds to the external threading 232 and 242 provided on fasteners 230 and 240, respectively.

Figure 78:
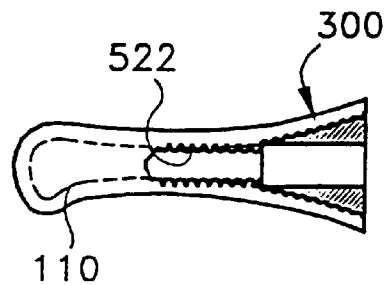
FIG. 78 is a cross-sectional view of the bone after the tap is removed from the bone.
Figure 79:
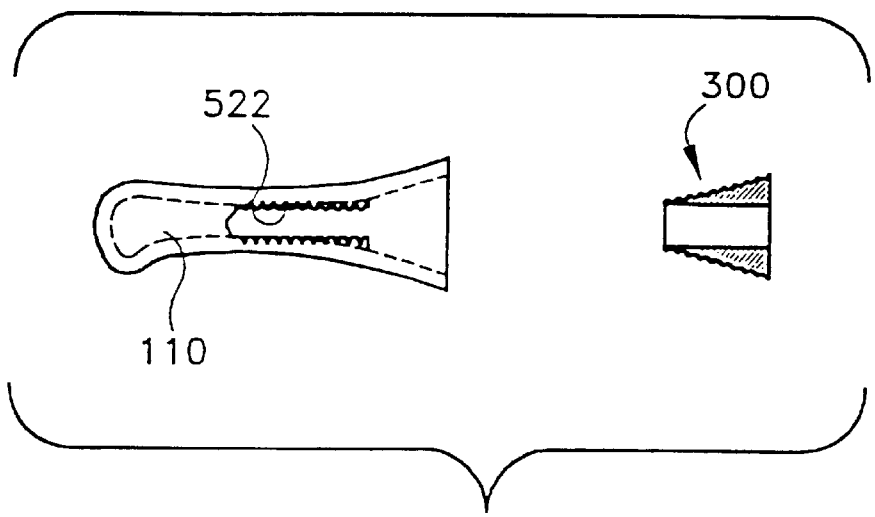
FIG. 79 is a view similar to FIG. 78, but showing the broach removed from the bone.

After the tapping operation is complete, the tap 500 is removed from the internally threaded bore 522 as shown in FIGS. 78. Thereafter, and as shown in FIG. 79, the broach 300 is removed from the bone as through suitable use of the tool 350.

Figure 80:
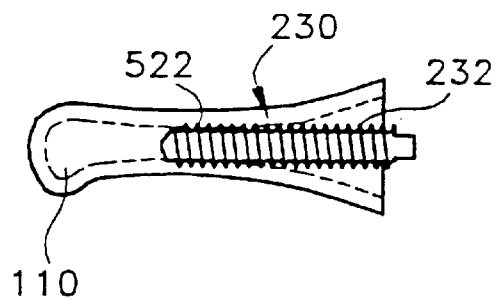
FIG. 80 shows a screw associated with one form of the joint assembly internally threaded within the medullary cavity of a bone.

Next, and as shown in FIG. 80, screw 230 of joint assembly 216 is inserted into the threaded bore 522 in the medullary cavity of the bone 110. Screw 230 is threaded into the threaded bore 522 until the joint end of screw 230 extends a predetermined distance outwardly or beyond the severed end of bone 110. Notably, the coarse pitch on the threading 232 of screw 230 cooperates with the internal threading 522 in the bone substance to establish a significant holding force between the screw 230 and the bone 110.

Figure 81:
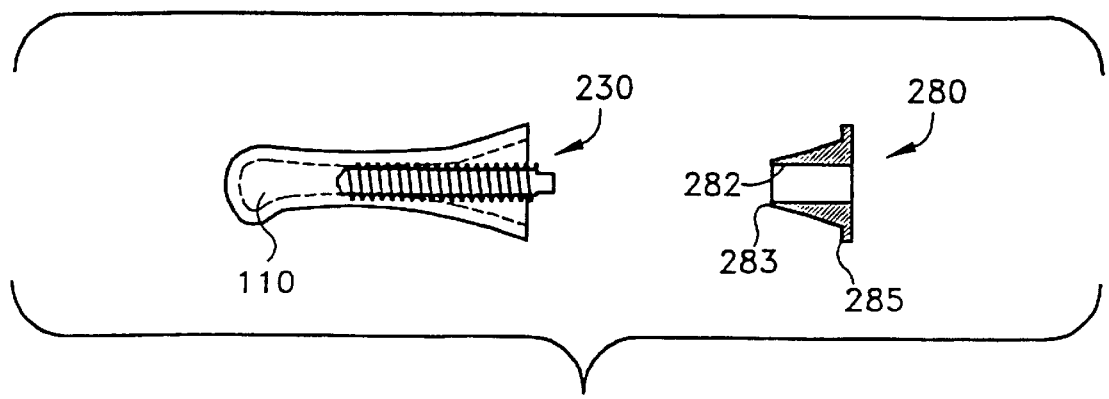
FIG. 81 is a view similar to FIG. 80, but showing a grommet illustrated in FIGS. 50 through 54 being arranged in spaced relation relative to the screws threadably arranged within the bone.
Figure 82:
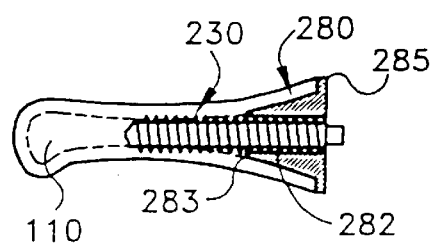
FIG. 82 is a view showing the grommet arranged in operable combination with the screw.

As shown in FIGS. 81 and 82, after screw 230 is secured within bone 110, grommet 280 is then pressed in place over the external threading on the screw 230. In the preferred embodiment of the invention, grommet 280 is pressed inwardly until the stop flange 285 contacts the severed bone surface. Notably, the outer surface configuration of the grommet 280 closely proximates or corresponds to the shaped surface of the inner endosteal surface of the bone 110.

Figure 83:
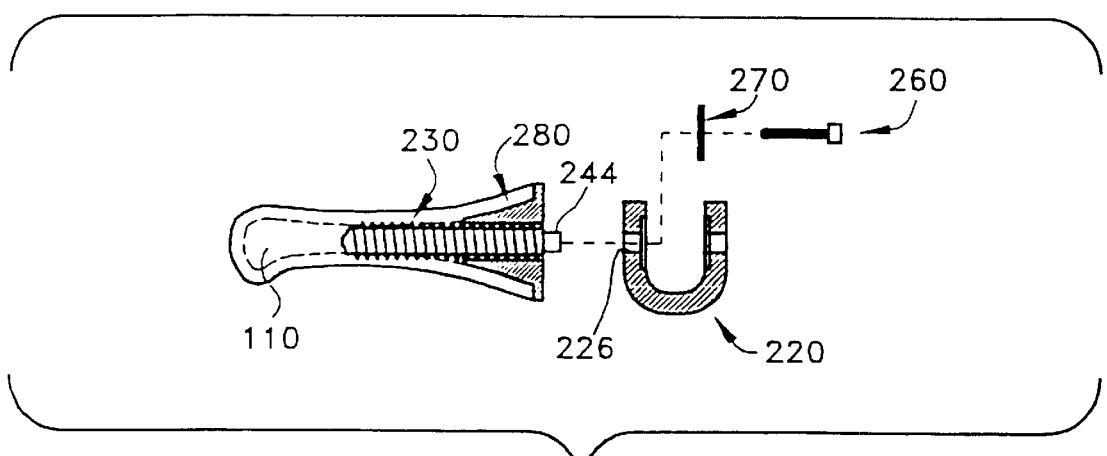
FIG. 83 is a partially assembled cross-sectional view similar to FIG. 49 showing a connector and the method of attachment to the screw.
Figure 84:
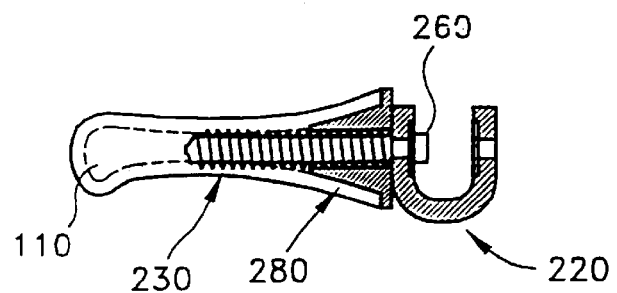
FIG. 84 is a view similar to FIG. 83 showing the connector fixedly attached to the screw.
Figure 85:
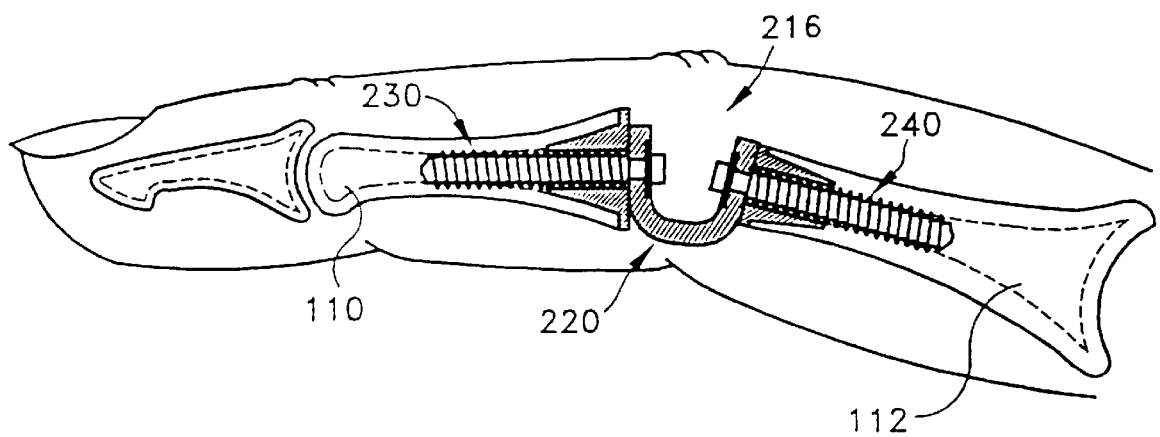
FIG. 85 is a view similar to FIG. 45.

As shown in FIG. 83, the connector 220 is thereafter fixedly secured to the joint end of the screw 230. As shown, the reduced diameter portion 244 of screw 230 passes endwise through the bore 226 defined by the connector 220. The subassembly of fastener 260 and washer 270 is then fastened to the screw 230. The fastener 260 is rotated thereby fixedly securing the leg portion of the connector 220 to the screw 230, as shown in FIG. 84. Turning to FIG. 85, the process described above is repeated with respect to bone 112. That is, the connector 220 is fixedly secured to the bone 112 such that natural proximal interphalangeal joint is replaced by the artificial joint assembly 216.

Figure 86:
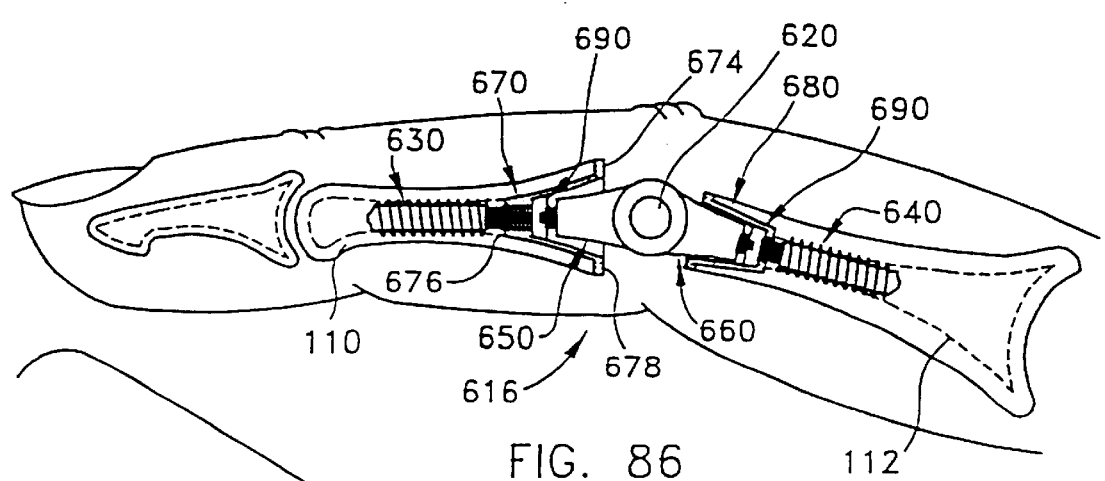
FIG. 86 is a view similar to FIG. 45 showing an alternative embodiment of the joint assembly of the present invention.
Figure 87:
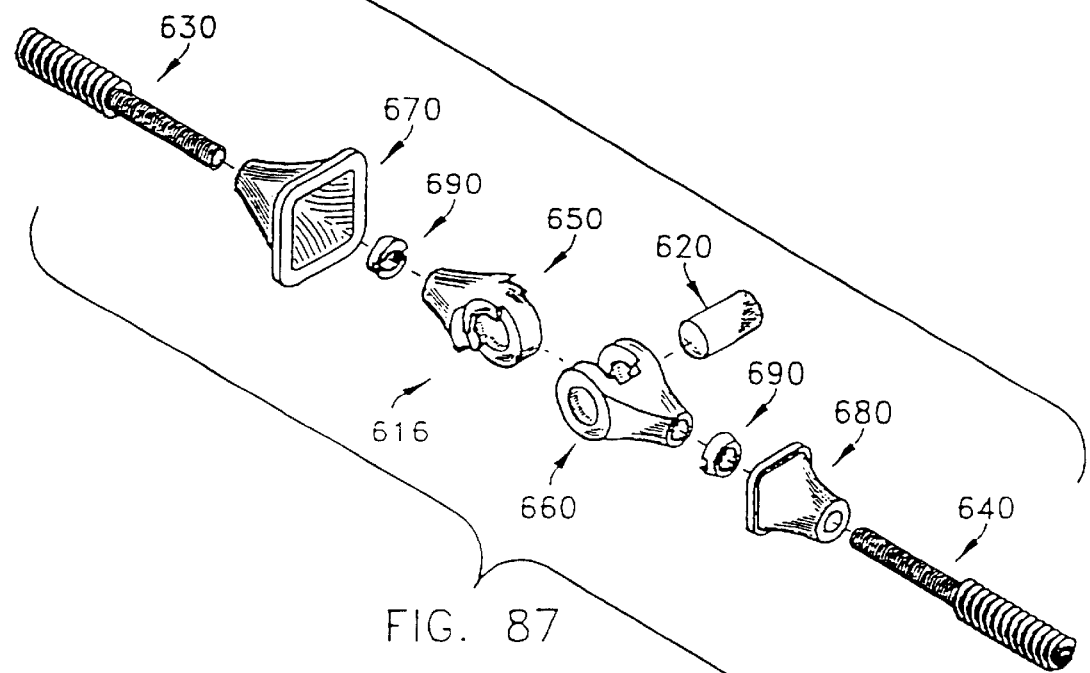
FIG. 87 is an exploded perspective view of that embodiment of the invention illustrated in FIG. 86 with component parts thereof shown in disassembled relation relative to each other.

Still another embodiment of the joint assembly according to the present invention is illustrated in FIGS. 86 and 87 and is designated generally therein by reference numeral 616. The joint assembly 616 functions to fixedly and articulately secure the surgically severed bones 110 and 112 in proper relationship relative to each other.

As shown in FIGS. 86 and 87, this alternative embodiment of the joint assembly 616 comprises a connector 620 for fixedly and articulately interconnecting joint ends of first and second screws 630 and 640, respectively, to each other.

As shown in FIGS. 88 and 89, connector 620 of joint assembly 616 is fabricated from a material that is biocompatible with the human and bone tissue and is preferably selected from a class comprised of: ultrahigh molecular weight polyethylene, ceramic, nylon or similar polymer. In the preferred embodiment, connector 620 comprises a cylindrical member 622 of a predetermined length. As shown, member 622 is substantially solid but it is within the spirit and scope of the present invention that the cylindrical member 622 could be formed as a cylindrical tube-like member.

In this embodiment of the invention, the first and second screws 630 and 640, respectively, are substantially identical. Accordingly, only screw 630 will be described in detail with the understanding that screw 640 is substantially identical thereto.

Figure 90:
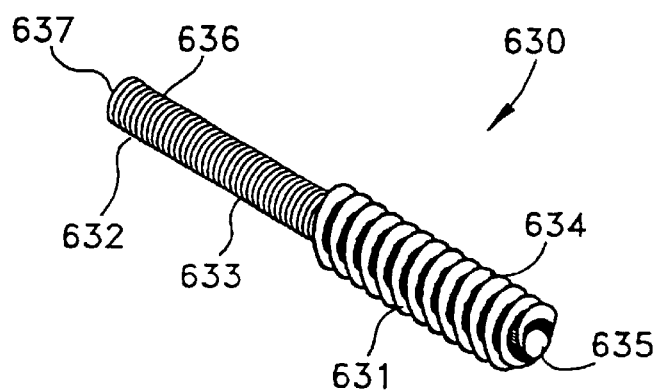
FIG. 90 is a perspective view of one component part of that embodiment of the invention illustrated in FIGS. 86 and 87.
Figure 91:
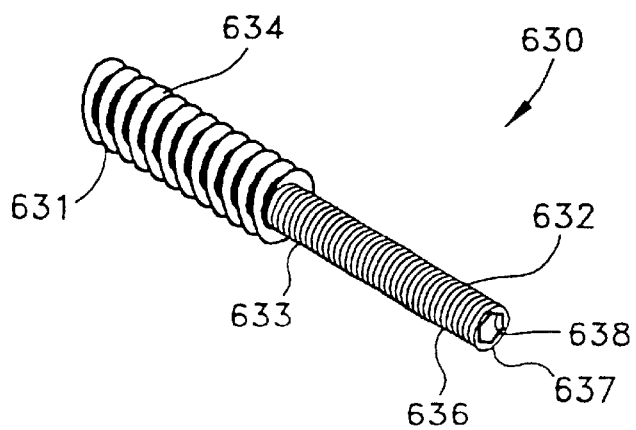
FIG. 91 is another perspective view of that component part illustrated in FIG. 90 but from a different angle.
Figures 92, 93, 94:
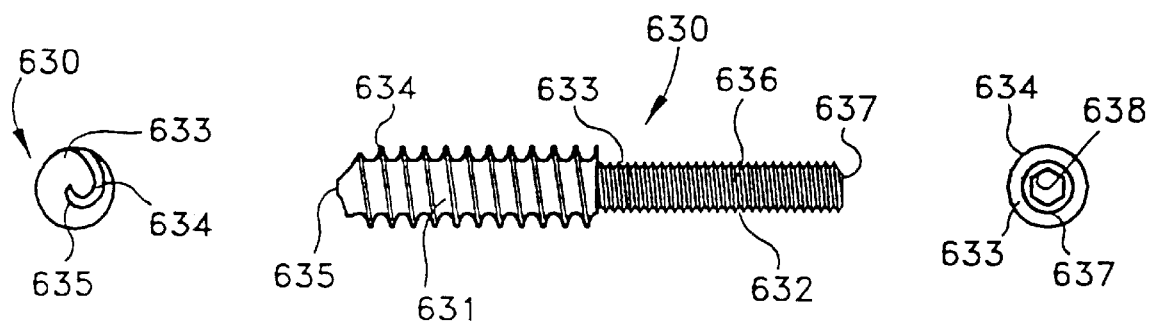
FIG. 92 is an elevational view of the component illustrated FIGS. 90 and 91.
FIG. 93 is a left end view of the component part illustrated in FIG. 92.
FIG. 94 is a right end view of the component part illustrated in FIG. 92.

As shown in FIGS. 90 through 92, each screw comprises first and second axially elongated and threaded sections 631 and 632, respectively, preferably formed from a single axially elongated member 633. The elongated member 633 is preferably fabricated from a material that is biocompatible with the human and bone tissue and is preferably from a class comprised of: titanium, a titanium based alloy, stainless steel, or a cobalt chromium based alloy.

The first section 631 of each screw 63Q, 640 includes external threading 634 extending axially lengthwise of section 631. The external threading 634 preferably has a generally uniform pitch between leading and trailing ends thereof. Moreover, the threading 634 on the first screw section 631 has a relatively coarse pitch such that a substantive holding force will be developed when the screw 630 is threadably secured within the bone substance of the respective bones. The threading 634 on screw section 631 extends axially rearwardly from a pointed end 635 (FIG. 90) defined by member 633.

The second section 632 of each screw 630, 640 likewise has external threading 636 extending forwardly from a trailing end 637 of member 633. The external threading 636 extends axially lengthwise of the second screw section 632 and has a uniform pitch. The threading 636 on the second screw section 632 has a relatively fine pitch.

As shown in FIG. 94, the trailing end 637 of screw 630 is provided with a configuration for releasably accommodating a driving tool. In a most preferred form of the invention, the trailing end 637 of screw 630 is provided with a hexagonally shaped blind bore 638 for releasably accommodating a driving tool. It should be appreciated, however, that any suitably shaped tool receiving configuration could be provided at the trailing end 637 of the screw for imparting turning movements thereto.

Returning to FIG. 87, the joint assembly 616 further includes a pair of sleeves 650 and 660 that combine with the screws 630 and 640, respectively, to fixedly and articulately interconnect the bones 110 and 112 (FIG. 86) to each other. Details concerning the sleeve 650 and 660 are provided in FIGS. 95 through 104.

Figure 97:
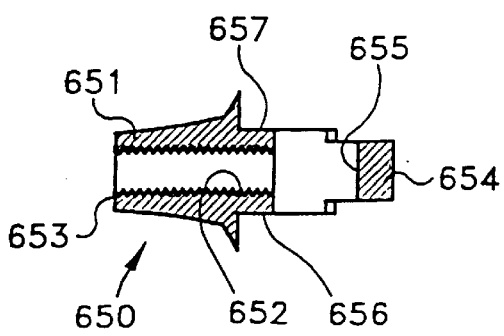
FIG. 97 is a sectional view taken along line 97—97 of FIG. 95.
Figure 98:
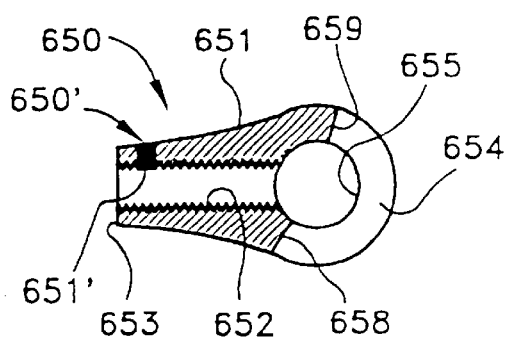
FIG. 98 is a sectional view taken along line 98—98 of FIG. 96.

As shown in FIGS. 95 through 98, sleeve 650 comprises a member 651 preferably fabricated from a material that is biocompatible with human bone tissue and is preferably selected from a class including: titanium, a titanium based alloy, stainless steel, or a cobalt chromium alloy. As shown in FIGS. 97 and 98, member 61 defines a internally threaded bore 652 which opens to an end 653 of member 651. The internal threading of bore 652 has a generally uniform pitch and is like handed with the fine pitched external threading 636 on the second section 632 of screws 630 and 640.

As shown, member 651 further defines an eye portion 654 at an opposite end of the sleeve 650. In this embodiment of the invention, the eye portion 654 of member 651 defines a cylindrical bore 655 having a closed margin defined by eye portion 654. Notably, bore 655 has a diameter that is specifically sized to establish a free or running fit relative to the connector 620 passing therethrough.

As shown in FIG. 96, eye portion 654 of member 651 further includes two generally planar and parallel surfaces 656 and 657 preferably disposed on opposite sides of the longitudinal axis of member 651. In a most preferred form of the invention, the surfaces 656 and 657 are equally disposed relative to the longitudinal axis of member 651. Moreover, each surface 656 and 657 defines a pair of stops 658 and 659. The stops 658 and 659 are disposed relative to the longitudinal axis of member 651 in a manner substantially similar to the stops 138 and 139 (FIG. 35) are disposed on member 131. Accordingly, no further description need be provided thereto.

As shown in FIG. 98, the sleeve 650 further includes a retaining apparatus 650'. The retaining apparatus preferably includes a non-metal member 651' disposed along the length of the internal threading of the bore 652 in sleeve 650. In a most preferred form of the invention, member 651' is formed from a material that is biocompatible with the bone and human tissues and is preferably selected from the class comprising: nylon or ultrahigh molecular weight polyethylene. Suffice it to say, the retaining apparatus 650' is disposed proximate the end 653 of sleeve 650 to inhibit inadvertent turning or rotation of the screw 630 and sleeve 650 relative to each other thereby maintaining the sleeve 650 in the adjusted position selected by the surgeon.

Figure 101:
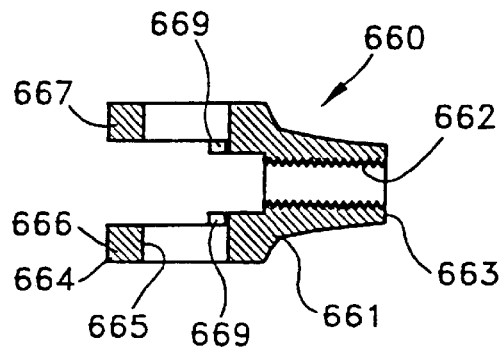
FIG. 101 is a sectional view taken along line 101—101 of FIG. 99.
Figure 102:
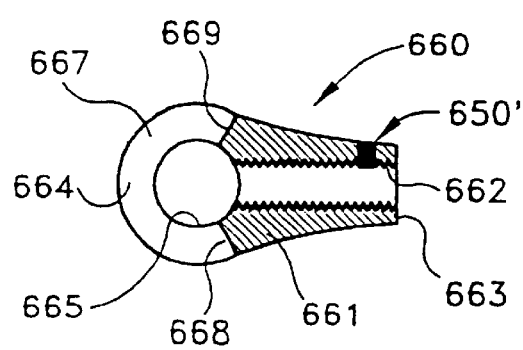
FIG. 102 is a sectional view taken along line 102—102 of FIG. 100.
Figure 104:
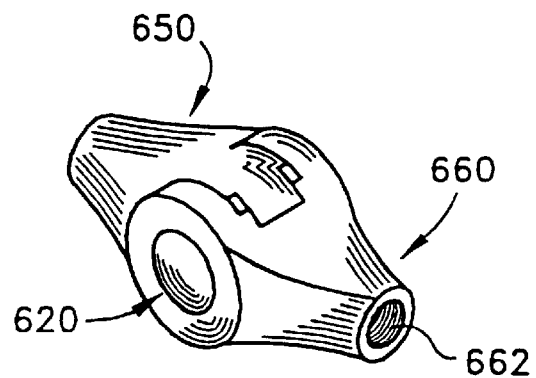
FIG. 104 is a perspective view of the component parts illustrated in FIG. 103 in assembled relation relative to each other.

As shown in FIGS. 99 through 102, sleeve 660 comprises an elongated member 661 that is preferably fabricated from a material that is biocompatible with the human and bone tissue and is preferably selected from a class including: titanium, a titanium based alloy, stainless steel or a cobalt chromium based alloy. As shown in FIGS. 101 and 102, the elongated member 661 defines a bore 662 having internal threading extending forwardly from an end 663 of member 661. Notably, the internal threading of bore 662 is like handed and corresponds to the external threading 636 provided on the second threaded section 632 of fastener 640.

As shown, member 661 defines an eye portion 664 at an end opposite end 663. In this embodiment or the invention, the eye portion 664 of member 661 defines a cylindrical bore 665 having a closed margin defined by the eye portion 664. Notably, bore 665 has a diameter that is specifically sized to accommodate the connector 620 therewithin and establish a press fit therewith.

It will be appreciated, of course, that the relationship of the members 651 and 661 relative to the connector 620 can be readily reversed from that disclosed without detracting or departing from the spirit and scope of the present invention. That is, the bore 655 defined by member 651 may be specifically sized to establish press fit relative to the connector 620 while the bore 665 of member 661 may accommodate and establish a free or running fit with the connector 120. Suffice it to say, the connector 620 is maintained in position by one of the members 651, 661 while allowing the other member 651, 661 to freely rotate about the longitudinal axis of the connector 620 and for purposes of this invention it does not significantly matter which member 651, 661 turns and which member 651, 661 holds the connector 620 in position.

In the illustrated embodiment, eye portion 664 of sleeve 660 includes a pair of bifurcated arms 666 and 667 defined on opposite sides of the longitudinal axis of member 661. In the illustrated embodiment of the invention, and to enhance the operability of the joint assembly 616, the bifurcated arms 666 and 667 are spaced apart by a distance which is greater than the distance separating the planar surfaces 656, 657 on the eye portion 654 of sleeve 650 such that a free or running fit is established between the eye portion 654 of sleeve 650 and the eye portion 664 of sleeve 660. Moreover, each bifurcated arm 666 and 667 of member 661 defines a pair of stops 668 and 669. The stops 668 and 669 are disposed relative to the longitudinal axis of member 631 in a similar manner as are stops 148 and 149 of member 141 of screw 140 discussed in detail above. Thus, no further detail need be provided thereto at this time.

As shown in FIG. 102, member 661 of sleeve 660 may further include a retaining apparatus 650'. The retaining apparatus 650' is substantially similar to that discussed above and, thus, no further detail need be provided thereto at this time.

Figure 103:
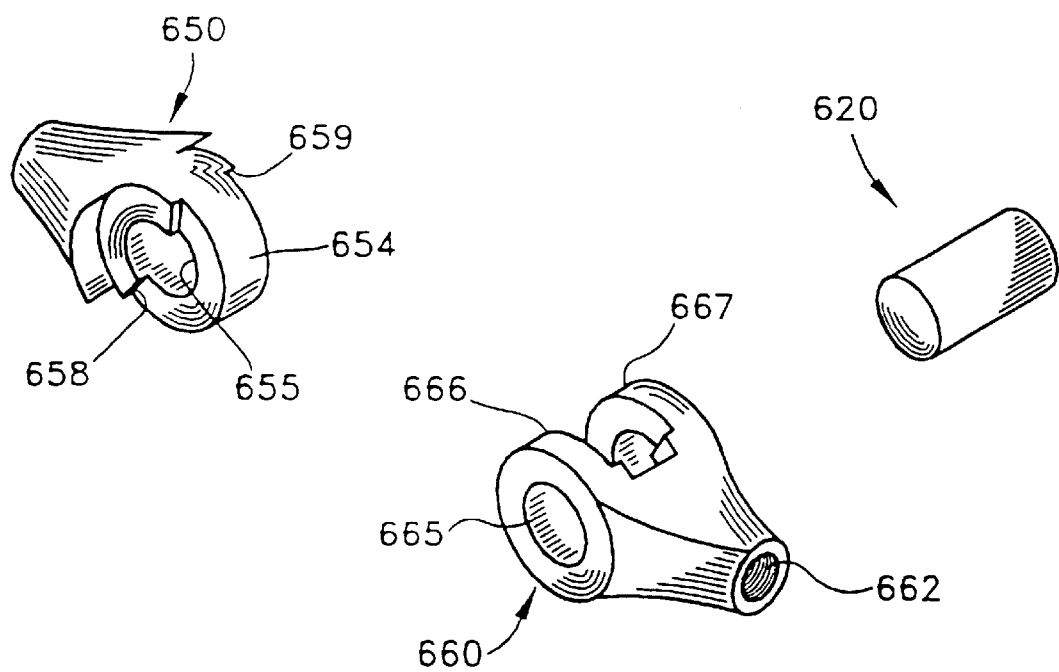
FIG. 103 is a perspective view of some of the component parts illustrated in FIGS. 86 and 87 in unassembled relation relative to each other.
Figure 110:
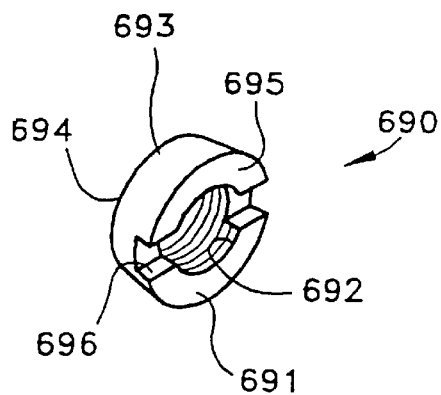
FIG. 110 is a perspective view of another component part of that embodiment of the joint assembly of the present invention illustrated in FIGS. 86 and 87.
Figure 111:
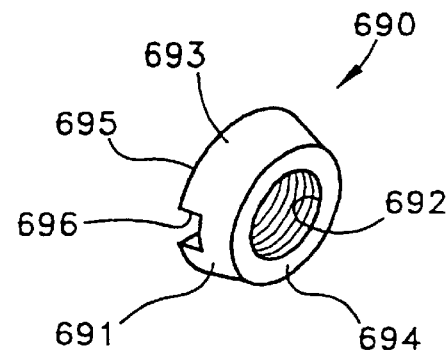
FIG. 111 is another perspective view of that component illustrated in FIG. 110.
Figure 112:
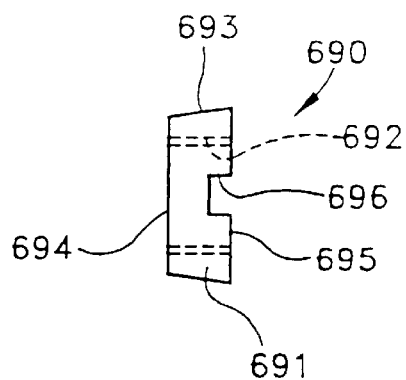
FIG. 112 is an elevational view of the component part illustrated in FIG. 110.
Figure 113:
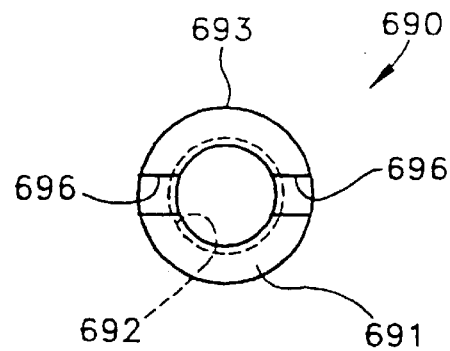
FIG. 113 is a right-end view of the component part illustrated in FIG. 110.

As shown in FIG. 103, sleeve 650 is adapted to fit between the bifurcated arms 666 and 667 of sleeve 660. Once the bore 655 in sleeve 650 is aligned with the bore 665 in sleeve 660, the connector 620 passes therethrough thereby fixedly and articulately interconnecting the sleeve 650 and 660 in the manner shown and FIG. 104.

Once again turning to FIG. 86, this alternative embodiment of the joint assembly 616 further includes first and second grommets 670 and 680. Notably, and in accordance with another aspect of the present invention, the grommets 670, 680 are intended to be provided in a plurality of different sizes. As will be appreciated, the various size grommets allow the surgeon to select a grommet that is sized to fit particularly well within the specific medullary cavity of the particular patient thereby advantageously stabilizing the joint assembly 616 relative to the end regions of bones 110 and 112 that are to be articulately joined relative to each other. As will be described below, the grommets 670 and 680 are specifically designed and/or configured to promote boney ingrowth. Thus, and while each screw 630, 640 initially fastens the joint assembly 616 in place, the grommets 670, 680 of the joint assembly 616, along with the boney ingrowth associated therewith, serve to securely fasten the joint assembly 616 in place for long term use.

As will be appreciated, and as mentioned, the specific sizes of the grommets 670, 680 can vary relative to each other. The intended function, purpose, and overall configuration of the grommets 670, 680 are, however, identical. Since the intended function, purpose, and overall configuration of the grommets 670, 680 are preferably identical, only grommet 670 will be discussed in detail with the understanding that the grommet 680 is substantially identical thereto.

The grommets used in combination with the finger joint assembly 616 is best illustrated in FIGS. 105 through 109. Each grommet 670, 680 is preferably formed from a material chosen from the class including: titanium, a titanium alloy, stainless steel, a cobalt chromium alloy ceramic or other suitable material that promotes boney ingrowth. As shown therein, each grommet 670, 680 includes an axially elongated member 671 defining a cavity 672 that opens to an end portion 674 of the grommet. A coaxial bore 675 extends inwardly and opens to the cavity 672 from an opposite end portion 676 of grommet 670. Notably, an annular shoulder 677 surrounds that portion of bore 675 that opens to the cavity 672. Moreover, the diameter of bore 675 is sized such that it is permitted to slide axially over and about the second externally threaded portion 632 of each fastener 630, 640. As shown in FIG. 86, end portion 676 has a cross-sectional configuration having a smaller diameter than that of the opposite end portion 674 to facilitate initial insertion and guidance of the respective grommet into the medullary cavity of the respective bone fragment. A stop flange 678 is preferably provided on each grommet 670, 680 to limit axial insertion or endwise movement of the respective grommet within the medullary cavity of the severed bone fragment.

As shown in FIG. 106, the outer surface configuration of member 671 has a changing and axially tapered configuration. In the illustrated embodiment, the outer surface configuration of member 671 changes from a generally rectangular configuration arranged toward that end adjacent the stop flange 678 to a generally circular configuration at the end portion 676 of each grommet. Different grommet configurations are preferably provided to the surgeon such that, and as mentioned above, during surgery, the surgeon selects that grommet configuration most closely corresponding to or proximating the inner endosteal surface configuration of the severed bone fragment. Moreover, the outer surface of each grommet 670, 680 extending between the opposed end portions 674, 676 is preferably treated to promote boney ingrowth. That is, the outer surface configuration of each grommet 670, 680 has a burnished surface finish or a cancerous micron pore size ranging between about 100 and about 450 microns to promote boney ingrowth with the surrounding bone tissue. The illustrated embodiment of the joint assembly 616 illustrated in FIG. 87 further shows that a stop 690 is arranged in operable combination with each grommet 670, 680 to stabilize the finger joint assembly 616 relative to the end regions of the bones 110 and 112.

The stop 690 is illustrated in FIGS. 110 through 113. As shown, stop 690 includes a frusto-conically shaped member 691 that is preferably formed from a material that is biocompatible with human and bone tissue and is preferably selected from a class comprised of: titanium, a titanium based alloy, stainless steel or a cobalt chromium alloy. Member 691 defines an internally threaded bore 692. The threading on bore 692 corresponds to the fine pitched external threading 636 on the second threaded portion 632 of each screw 630, 640. The outer surface 693 of member 691 preferably has an axially tapered surface between opposed ends 694 and 695, respectively, of member 691. The tapered surface configuration on the outer surface 693 of stop 690 generally corresponds to the tapered surface configuration preferably provided on the interior surface of the cavity 672 defined by grommets 670 and 680. Moreover, end 695 of member 691 is configured to releasably accommodate a driving tool. In the illustrated embodiment of the invention, end 695 of member 691 is configured with two diametrically spaced slots 696 for releasably accommodating a screwdriver or the like.

Figure 114:
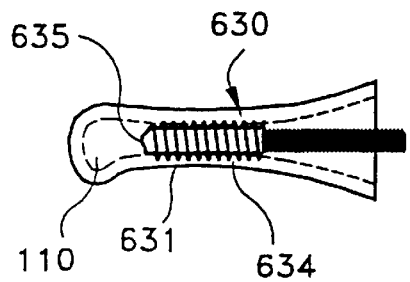
FIG. 114 is a cross-section view showing a screw associated with that embodiment of the invention illustrated in FIGS. 86 and 87 and of the type illustrated in FIGS. 90 through 94 being threadably inserted into a bone.

As will be appreciated, after the end regions of the bones 110 and 112 are severed, each bone 110 and 112 is prepared in the manner discussed in detail above. That is, a tap (not shown) is inserted into a suitably sized and drilled bore to provide internal threading in the medullary cavity of the bone 110. Thereafter, and as shown in FIG. 114, screw 630 is threadably inserted within the internally threaded bone cavity of bone 110. The pointed end 635 of the screw 630 is initially inserted and the relatively coarse pitch external threading 634 on the first section 631 of the screw 630 threadably engages with the internal threading within the bone. The coarse pitch threading, of course, inhibits the screw 630 from being pulled out of the bone and enhances its attachment to the bone.

Figure 115:
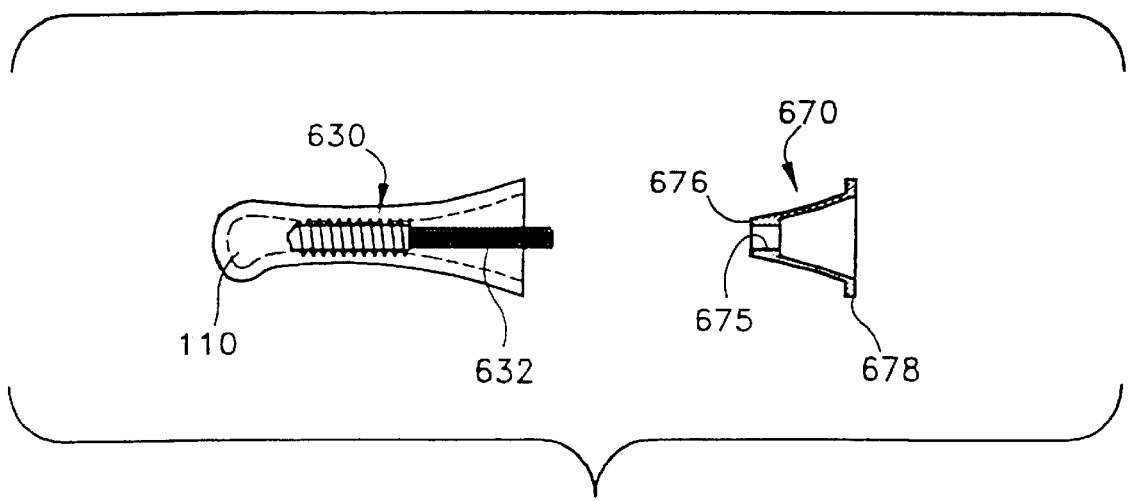
FIG. 115 is a cross-section view showing a grommet of the type illustrated in FIGS. 105 through 109 being axially aligned for insertion about the screw shown in FIG. 114.
Figure 116:
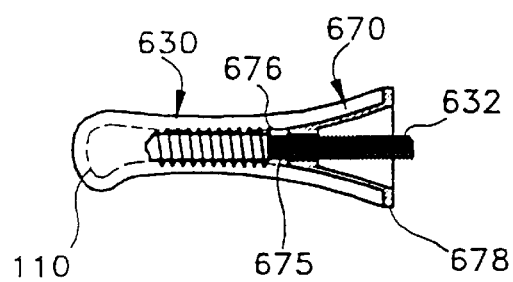
FIG. 116 is a cross-section view similar to FIG. 115 but showing the grommet arranged in operable combination with the screw.

As shown in FIGS. 115 and 116, after the screw 630 is threadably attached to the bone 110, the grommet 670 is then endwise arranged over the second externally threaded lengthwise portion 632 of screw 630. As discussed above, the bore 675 leading inwardly from the end portion 676 of grommet 670 is sized to specifically fit over the external threading of the second portion 632 of screw 630. The grommet 670 is sidably moved over the screw 630 until the flange 678 abuts against the severed end region of bone 110.

Figure 117:
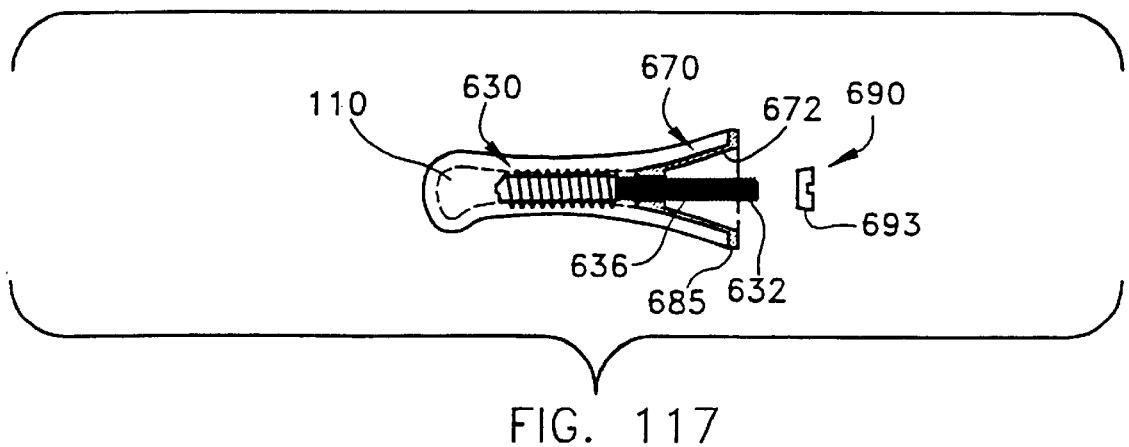
FIG. 117 is a cross-section view similar to FIG. 116 showing a securing member similar to that shown in FIGS. 110 through 113 being axially aligned with the screw.
Figure 118:
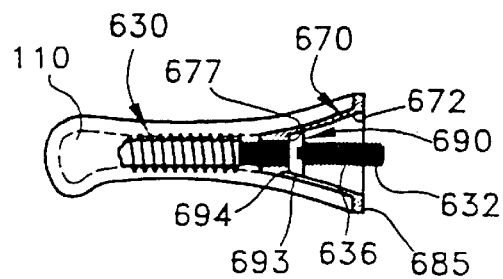
FIG. 118 is a cross-section view similar to FIG. 117, but showing the securing member arranged in operable combination with the grommet.

To further enhance the securement of the grommet 670 within the bone and as shown in FIGS. 117 and 118, stop 690 is axially threaded along the external threading 636 of the second threaded portion 632 of the screw 630. Notably, the tapered outer surface 693 cooperates with the similarly configured internal surface of cavity 672 of the grommet 670 thereby centering the grommet 670 within the medullary cavity of the severed bone. Stop 690 is threaded along the first screw 630 until end 694 engages and presses against the shoulder 677 of grommet 670. Continued rotation of the stop member 690 will forcibly urge the flange 678 into fixed relation relative to the severed end of the bone.

Figure 120:
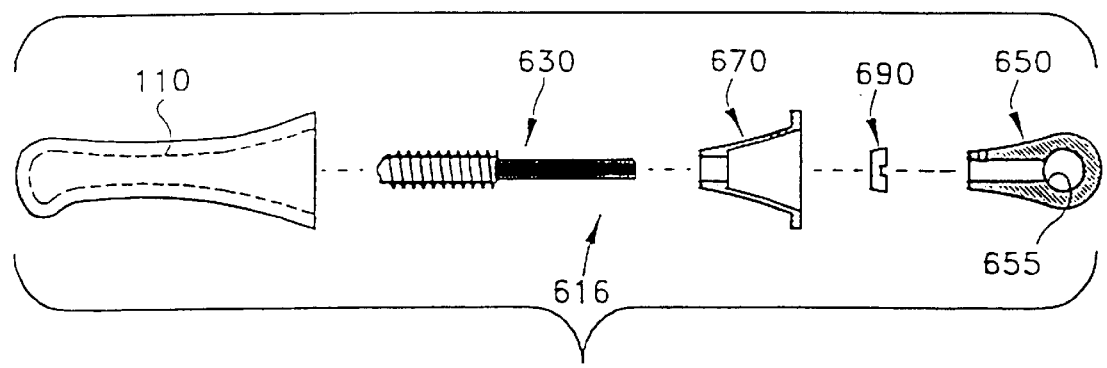
FIG. 120 is an elevational view, partly in section, showing some of the component parts of that embodiment of the present invention illustrated in FIGS. 86 and 87 in disassembled relation relative to each other.
Figure 119:
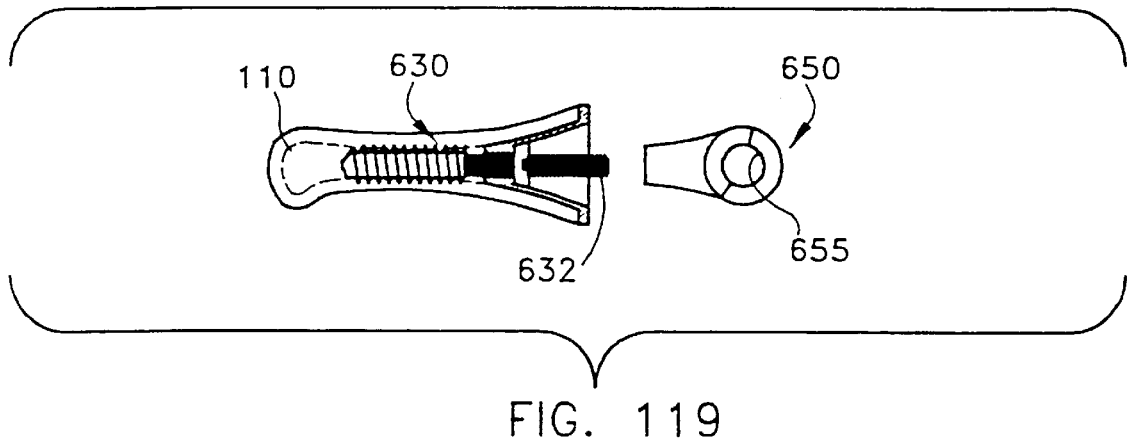
FIG. 119 is a cross-section view similar to FIG. 118, but showing the component part similar to that illustrated in FIGS. 95 through 98 being arranged for operable engagement with the component parts illustrated in FIG. 118.
Figure 121:
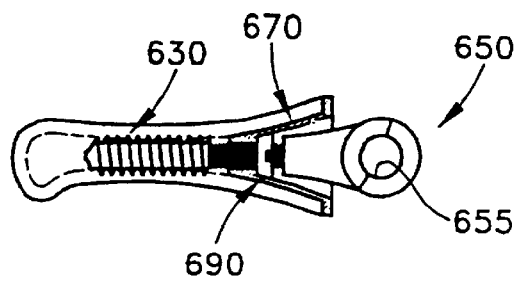
FIG. 121 is an elevational view, partly in section, showing those component parts of the present invention illustrated in FIG. 120 in assembled relation relative to each other.

Next, and as shown in FIG. 119 and 121, sleeve 650 is threaded along the externally threaded second portion 632 of fastener 630 until the bore 655 is disposed a predetermined distance from the surgically severed end of bone 110. The ordered relation of insertion of the various component parts of joint assembly 616 into the bone 10 is schematically illustrated in FIG. 120. The assembled relation of the first screw 630, grommet 670, stop member 690 and sleeve 650 is schematically illustrated in FIG. 121.

Figure 122:
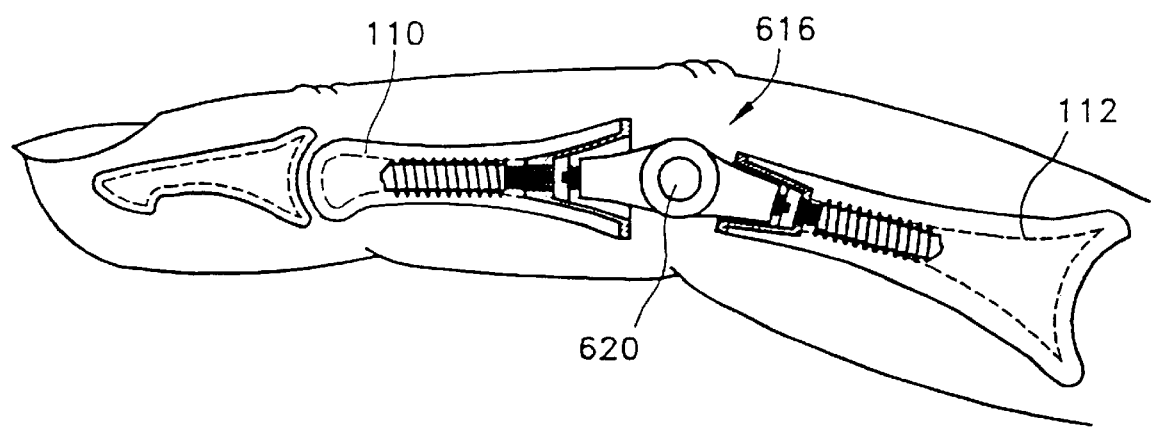
FIG. 122 is a view similar to FIG. 86.

As will be appreciated, the insertion process of the component parts of the fastener assembly 616 is repeated with respect to bone 112 and the assembled proximal interphalangeal joint is schematically illustrated in FIG. 122.

In the embodiment of the joint assembly illustrated in FIG. 28 through 30 or the embodiment illustrated in FIG. 86, and as will be appreciated from an understanding of the present invention, relative turning movement must be permitted between the component parts and the connectors 120 and 620, respectively. Accordingly, there is a possibility that the connector 120, 620 could present problems unless the proper clearance is maintained between the component parts. The embodiment of the invention illustrated ill FIGS. 123 through 125 eliminates concerns over appropriate tolerances and clearances between the component parts of the present invention intended to be maintained in operable association relative to each other under the influence of particular tolerances between the component parts.

Figure 123:
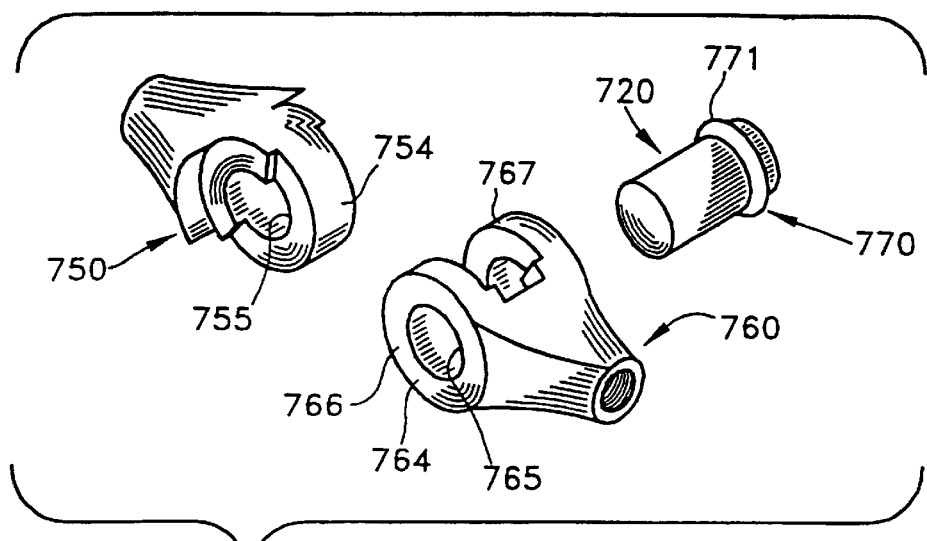
FIG. 123 is a perspective view similar to FIG. 103 partially showing an alternative embodiment of the present invention.
Figure 124:
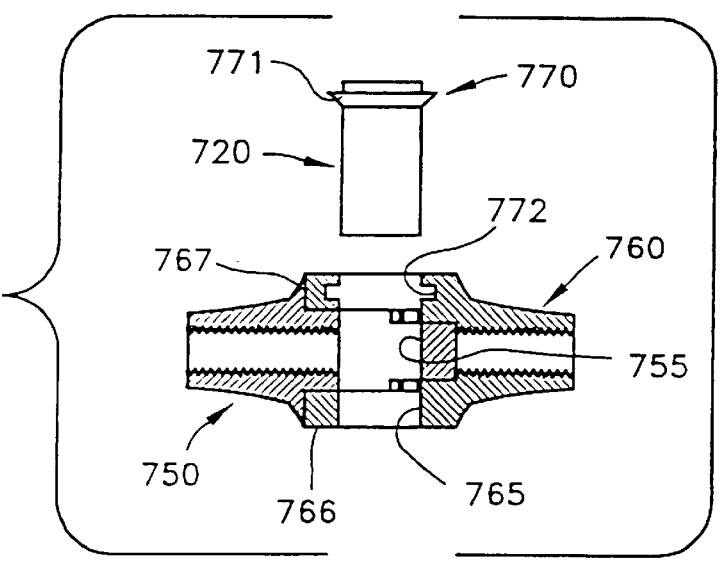
FIG. 124 is a longitudinal sectional view showing the component parts of the subassembly illustrated in FIG. 123 in partially assembled relation relative to each other.
Figure 125:
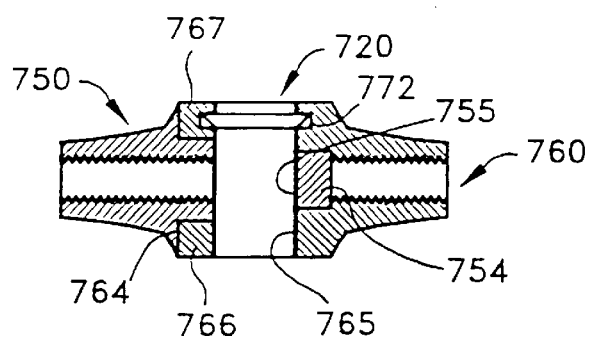
FIG. 125 is a longitudinal sectional view similar to FIG. 124 showing all the components of the subassembly in assembled relation relative to each other.

The component parts illustrated in FIGS. 123 through 125 include a connector 720 along with sleeves 750 and 760. With certain exceptions described in detail below, connector 720 is substantially similar to connector 620 illustrated in FIGS. 88 and 89 and described in detail above. Similarly, sleeve 750 is substantially similar to sleeve 650 illustrated in FIGS. 95 through 98 and described in detail above. Thus, no further description need be provided thereto at this time. Moreover, the sleeve 760 is substantially similar to sleeve 660 described in detail above and illustrated in FIGS. 99 through 102. Thus, no further detailed description need be provided thereto.

In this embodiment of the invention, a retainer apparatus 770 is provided for releasably maintaining the connector 720 in combination with sleeves 750 and 760. In this alternative embodiment of the invention, the connector 720 has an annular retaining ring 771 arranged proximate to one end thereof. Moreover, the bifurcated arm on sleeve 760 arranged adjacent that end of the connector 720 having the annular ring 771 is configured with an annular channel 772.

As shown in FIG. 125, and as described above, the eye portion 754 of sleeve 750 fits between the bifurcated arms 766 and 767 defining the eye portion 764 of sleeve 760. Sleeves 750 and 760 are adjusted until their bores 755 and 765, respectively, are in axial alignment relative to each other. Thereafter, connector 720 is axially slid through the aligned bores 755 and 765. Preferably, the annular ring 771 on connector 720 is formed from a pliable material that is biocompatible with the human and bone tissue substance wherein the joint assembly of the present invention is adapted for use. Suffice it to say, the annular ring 771 is formed from a material that allows the ring 771 to compress and subsequently snap into and combine with the annular channel 772 in a manner permitting inadvertent axial displacement of the connector 720 relative to the sleeve member 750 and 760. By this design, the connector 720 and the bores 755 and 765 of the sleeve member 750 and 760, respectively, can have looser tolerances while remaining assured that the connector 720 will remain fixed relative to the sleeve 750 and 760.

Figure 126:
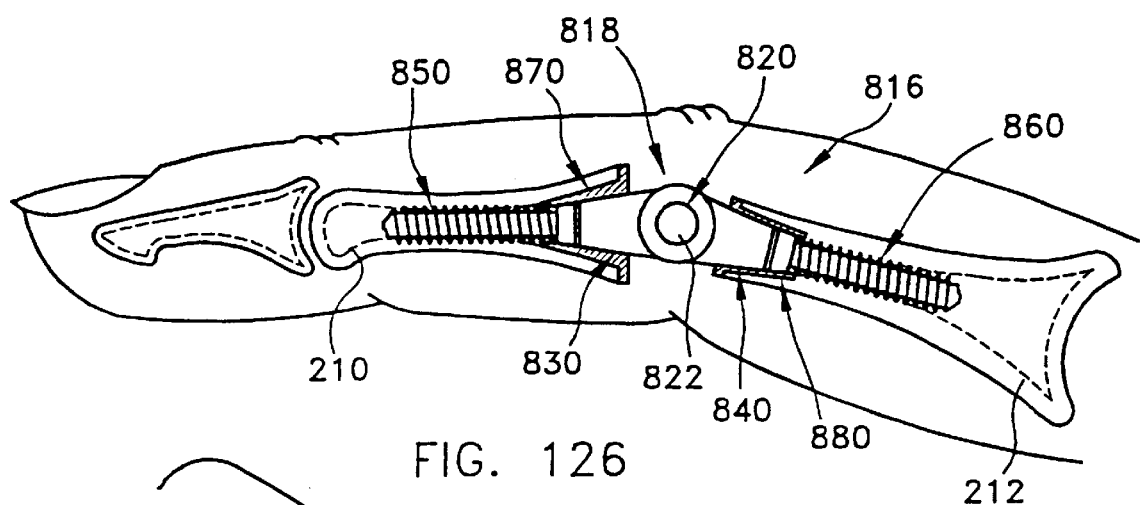
FIG. 126 is a view similar to FIG. 86 showing another alternative embodiment of the implanted joint assembly of the present invention.

Still another embodiment of an artificial joint assembly according to the present invention is illustrated in FIG. 126 and is designated generally therein by reference numeral 816. The joint assembly 816 functions to fixedly and articulately interconnect surgically severed bones 210 and 212 in proper relationship relative to each other.

Figure 127:
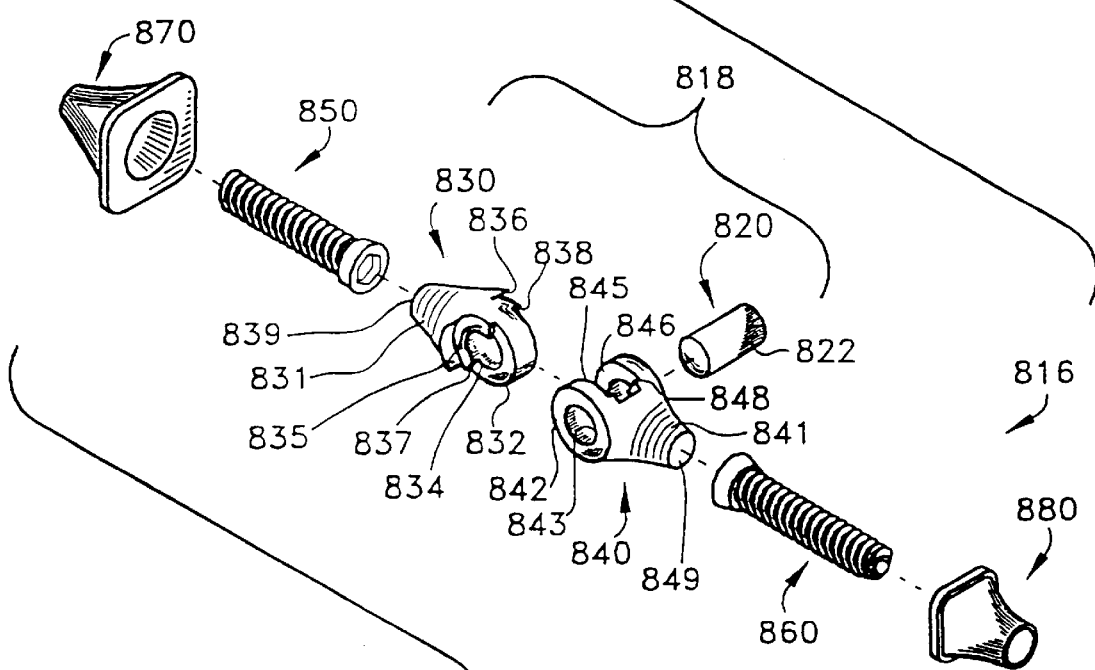
FIG. 127 is an exploded perspective view of that embodiment of the invention illustrated in FIG. 126 with component parts thereof shown in disassembled relation relative to each other.
Figure 128:
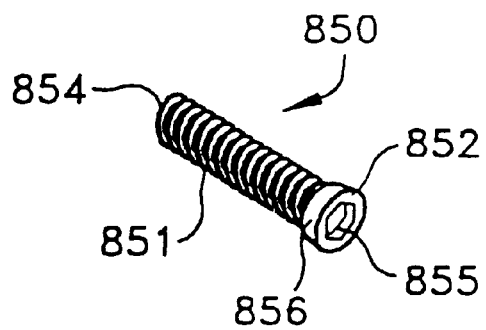
FIG. 128 is a perspective view of one component part of the embodiment illustrated in FIG. 127.
Figure 129:
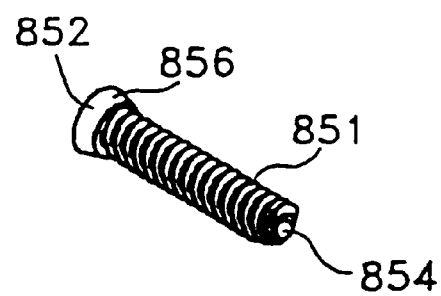
FIG. 129 is a perspective view of that component part illustrated in FIG. 128 but from a different perspective.
Figure 130:
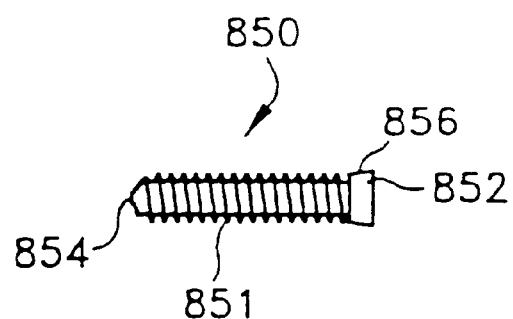
FIG. 130 is an elevational view of the component part illustrated in FIGS. 128 and 129.
Figure 131:
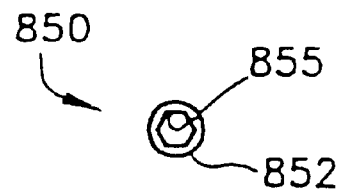
FIG. 131 is an right end view of the component part illustrated in FIG. 130.

As shown in FIGS. 126 and 127, this alternative embodiment of the joint assembly 816 comprises a connector assembly 818 operably associated with first and second grommets 870 and 880, respectively. As shown, the connector assembly 818 comprises a connector 820 for articulately interconnecting first and second sleeves 830 and 840, respectively, that are accommodated within the first and second grommets 870 and 880, respectively.

The connector 820 of connector assembly 818 is fabricated from a material that is biocompatible with the human and bone tissue and is preferably selected from a class comprised of: ultrahigh molecular weight polyethylene, ceramic, nylon or similar polymer. In the preferred embodiment, connector 820 comprises a cylindrical member 822 of a predetermined length. As shown, member 822 is substantially solid but it is within the spirit and scope of the present invention that the cylindrical member 822 could be formed as a cylindrical tube-like member.

As shown in FIG. 127, the sleeve 830 comprises an axially elongated member 831 preferably fabricated from a material that is compatible with human bone tissue and is preferably selected from the class including: titanium, a titanium alloy, stainless steel, or a cobalt chromium alloy. At one end, member 831 includes an eye portion 832 defining a cylindrical bore 834 preferably having a closed margin. The bore 834 defined by the eye portion 832 of member 831 has a diameter specifically sized to establish a free or running fit relative to the connector 820 passing endwise therethrough.

As shown in FIG. 127, eye portion 832 of member 831 further includes two generally planar and parallel surfaces 835 and 836 preferably disposed on opposite sides of the longitudinal axis of member 831. In a most preferred form of the invention, the surfaces 835 and 836 are equally disposed relative to the longitudinal axis of member 831. Moreover, each surface 835 and 836 defines a pair of stops 837 and 838. The stops 837 and 838 are disposed relative to the longitudinal axis of member 831 in a manner substantially similar to the stops 138 and 139 (FIG. 35) are disposed on member 131. Accordingly, no further description need be provided thereto.

In the illustrated embodiment, an end portion 839 of member 831 opposite from eye portion 832 has a generally circular cross-sectional configuration. The cross-sectional configuration of the end portion 839 is considerably smaller than the eye portion 832 to facilitate insertion of the sleeve 830 into grommet 870 as will be discussed below. In this embodiment of the invention, the outer surface of sleeve 830 axially extending from end portion 839 has a frusto-conical configuration between end portion 839 and the eye portion 832.

As shown in FIG. 127, sleeve 840 comprises an elongated member 841 preferably fabricated from a material that is biocompatible with the human and bone tissue and is preferably selected from a class including: titanium, a titanium based alloy, stainless steel or a cobalt chromium based alloy. At one end, member 841 includes an eye portion 842 defining a cylindrical bore 843 having a closed margin. Notably, bore 843 has a diameter that is specifically sized to accommodate the connector 820 therewithin and establish a press fit therewith.

It will be appreciated, of course, that the relationship of the members 831 and 841 relative to the connector 820 can be readily reversed from that disclosed without detracting or departing from the spirit and scope of the present invention. That is, the bore 834 defined by member 831 of sleeve 830 may be specifically sized to establish press fit relative to the connector 820 while the bore 843 of sleeve member 841 may accommodate and establish a free or running fit with the connector 120. Suffice it to say, the connector 820 is maintained in position by one of the members 831, 841 while allowing the other member 831, 841 to freely rotate about the longitudinal axis of the connector 820 and for purposes of this invention it does not significantly matter which member 831, 841 turns and which member 831, 841 holds the connector 820 in position.

In the illustrated embodiment, eye portion 842 of sleeve 840 includes a pair of bifurcated arms 845 and 846 defined on opposite sides of the longitudinal axis of member 841. In the illustrated embodiment of the invention, and to enhance the operability of the joint assembly 816, the bifurcated arms 845 and 846 are spaced apart by a distance which is greater than the distance separating the planar surfaces 835, 836 on the eye portion 832 of sleeve 830 such that a free or running fit is established between the eye portion 832 of sleeve 830 and the eye portion 842 of sleeve 840. Moreover, each bifurcated arm 845 and 846 of member 841 defines a pair of stops 847 and 848. The stops 847 and 848 are disposed relative to the longitudinal axis of member 841 in a similar manner as are stops 148 and 149 of member 141 of screw 140 discussed in detail above. Thus, no further detail need be provided thereto at this time.

In the illustrated embodiment, the other end portion 849 of sleeve member 841 has a generally circular cross-sectional configuration. The cross-sectional configuration of the end portion 849 of member 841 opposite from eye portion 842 is considerably smaller in area than the eye portion 842 to facilitate insertion of the sleeve 840 into the respective grommet as will be discussed below. In this embodiment of the invention, the outer surface of sleeve 840 axially extending from end portion 849 has a frusto-conical configuration between end portion 839 and the eye portion 832.

First and second screws 850 and 860, respectively, are used to initially fasten the grommets 870 and 880, respectively, within the medullary cavities of the respective bones. In this embodiment of the invention, the first and second screws 850 and 860, respectively, are substantially identical. Accordingly, only screw 850 will be described in detail with the understanding that screw 860 is substantially identical thereto.

As shown in FIGS. 128 through 131, each screw comprises an axially elongated and externally threaded portion 851 and an enlarged head portion 852 at one end thereof. The externally threaded portion 851 preferably has a generally uniform pitch between leading and trailing ends thereof. Moreover, the externally threaded portion 851 has a relatively coarse pitch for initially establishing a substantive holding force relative to the bone substance into which the screw is threaded. In a most preferred form, the external threading 851 on each screw extends axially rearward from a pointed end 854 that facilitates insertion of the screw into the respective bone substance.

The head portion 852 of each screw 850, 860 is configured to releasably accommodate a driving tool capable of imparting turning movement to the respective screw. In the illustrated embodiment shown in FIGS. 128 and 131, a hexagonally shaped recess 855 is preferably provided in the head portion 852 of each screw 850, 860 for releasably accommodating a driving tool capable of imparting turning movement to a respective screw. It should be appreciated, however, that other tool accommodating configurations would equally suffice. As will be appreciated, as each screw 850, 860 is turned, the external threading thereon engages with the bone substance. Moreover, the outer surface 856 of the head portion 852 of each screw 850, 860 has a frusto-conical configuration for purposes to be described hereinafter. By such design, the head portion 852 of each screw 850, 860, at that end closest to the pointed end 854, is of a first predetermined diameter that is smaller in size than the second predetermined diameter of the head portion 852 at the distal end of screw 850, 860.

As mentioned above, the joint assembly 816 further includes first and second grommets 870 and 880, respectively. Not unlike that mentioned above, the grommets 870 and 880 are intended to be provided in a plurality of various sizes. As will be appreciated, the various size of the grommets 870, 880 allow the surgeon to select a grommet that is sized to particularly fit well within the medullary cavity of the particular patient wherein a joint is being replaced thereby advantageously stabilizing the joint assembly relative to the end regions of the bones 210 and 212 that are to be articulately joined to each other. Moreover, and like those mentioned above, the grommets 870 and 880 are specifically designed and/or configured to promote boney ingrowth. Thus, and while each screw 850, 860 serves to initially fasten the joint assembly 816 in place, the grommets 870 and 880, along with their boney ingrowth relative to the bone substance, serve to positively maintain the joint assembly 816 in place for long term usage.

As will be appreciated, and as mentioned above, the specific sizes of the grommets 870, 880 can vary relative to each other. The intended function, purpose, and overall configuration of the grommets 870, 880 are, however, preferably identical to each other. Accordingly, only a detailed description of grommet 870 will be provided with the understanding that grommet 880 is substantially similar thereto.

An exemplary embodiment of the grommets used as part of joint assembly 816 is illustrated in FIGS. 132 through 136. Each grommet of the joint assembly 816 is preferably formed from a material chosen from the class including: titanium, a titanium alloy, stainless steel, or a cobalt chromium alloy. As shown, each grommet of joint assembly 816 includes an axially elongated member 871 that defines a cavity 872 that opens to end 873 of the grommet. Preferably, a coaxial bore 874 extends axially inward and opens to cavity 872 from an opposite end 875 of the grommet.

Notably, the interior surface of the cavity 872 has a frusto-conical configuration that closely proximates the frusto-conical configuration of the outer surface 856 of the head portion 852 of each screw 850, 860. Moreover, the interior surface configuration of the cavity 872 closely proximates the outer frusto-conical surface configuration on the respective sleeve 830, 840 adapted to be fitted therewithin. It is also important to note that the smallest diameter portion of the cavity 872 has a diameter smaller than the first predetermined diameter of the head portion 852 of each screw 850, 860 thereby preventing the respective screw from passing endwise therethrough when the artificial joint assembly 816 is implanted within the living body of the patient. In this regard, the diameter of the coaxial bore 874 is sized such that it permits the threaded portion 851 of the respective screw 850, 860 to axially slide or pass endwise through the respective grommet to be fastened within bone substance while the head portion 852 of the respective screw 850, 860 remains in operable combination with the grommet.

Figure 137:
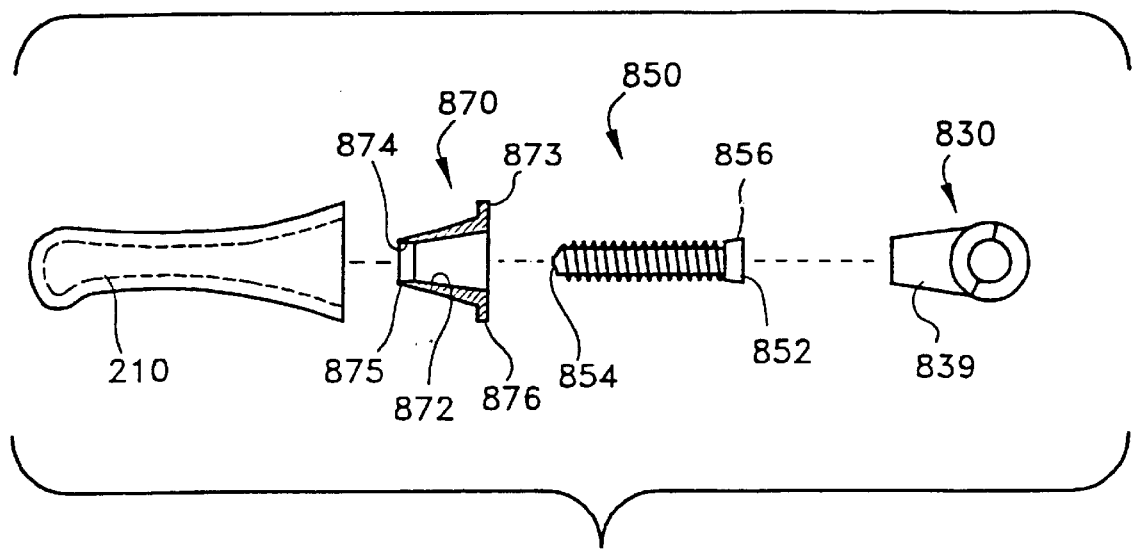
FIG. 137 shows some of the component parts illustrated in FIG. 127, partly in section, in disassembled relationship relative to each other.

In operation, opposing end regions of the bones 210 and 212 are surgically severed to expose the medullary cavity of each bone 210, 212. As shown in FIG. 137, grommet 870 is then inserted into the exposed cavity. The end portion 875 of each grommet is adapted to be initially inserted into the medullary cavity of the surgically severed bone and is, accordingly, a smaller diameter than end portion 873. A stop flange 876 is preferably provided at the end portion 873 of each grommet to limit axial insertion or endwise movement of the grommet within the medullary cavity of the surgically severed bone.

Figure 132:
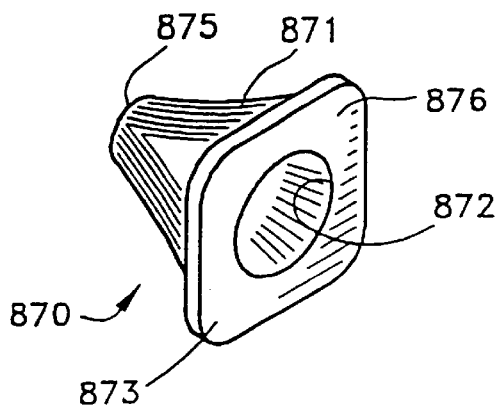
FIG. 132 is a perspective view of an alternative form of grommet used in combination with that embodiment of the invention illustrated in FIGS. 126 and 127.
Figure 133:
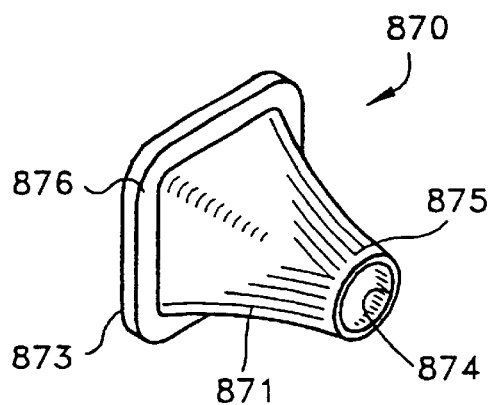
FIG. 133 is a perspective view of that component part illustrated in FIG. 132 but from a different perspective.
Figure 134:
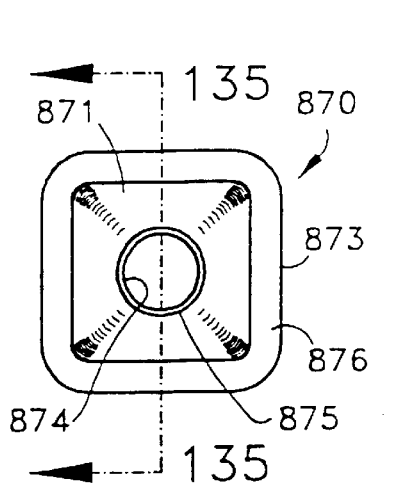
FIG. 134 is an end view of the component part illustrated in FIG. 133.
Figure 135:
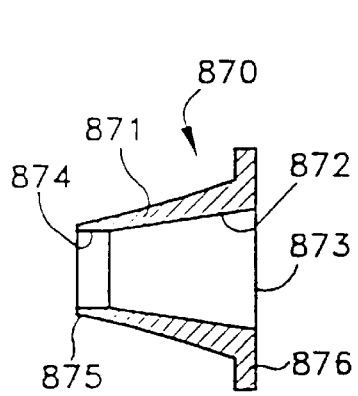
FIG. 135 is a sectional view taken along line 135—135 of FIG. 134.
Figure 136:
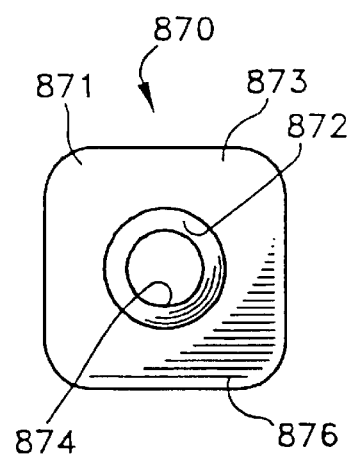
FIG. 136 is an end view of the component part illustrated in FIG. 132.

As shown in FIGS. 132 through 133, the end portion 875 of each grommet 870, 880 preferably has a generally circular cross-sectional configuration that tapers outwardly to end region 873 having a larger and preferably rectangular cross-sectional configuration. Suffice it to say, the grommet selection is chosen by which grommet configuration most closely corresponds to or proximates the inner endosteal surface configuration of the severed bone.

The outer surface of each grommet 870, 880 extending between opposed end portions 873 and 875 is preferably treated to promote boney ingrowth. That is, the outer surface of each grommet 870, 880 preferably has a burnished surface finish or a cancellous micron pore size ranging between about 100 and about 450 microns to promote boney ingrowth between the surrounding bone tissue and the respective grommet.

Returning to FIG. 137, following insertion of the grommet 870 into the medullary cavity, the pointed end 854 of screw 850 is inserted into and through cavity 872 and bore 874 of grommet 870 such that it can be fastened into the bone substance of bone 210. Notably, the tapered outer surface 856 of the head portion 852 of screw 850 cooperates with the internal surface of cavity 872 on grommet 870 to further draw and enhance securement of the grommet 870 into the medullary cavity of bone 210. It is important to note that the head portion 852 of screw 850 and the cavity 872 of grommet 870 are sized relative to each other to prevent the head portion 852 of the screw 850 from passing endwise through the bore 874 of grommet 870. Preferably, the grommet 870 is drawn into the medullary cavity until the stop flange 876 abuts with the exposed end region of the surgically severed bone 210 thereby adding stability to the joint assembly 816.

Figure 139:
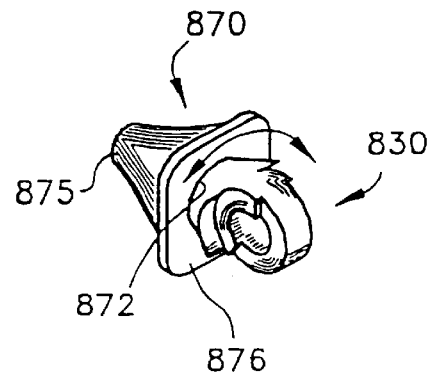
FIG. 139 is a perspective view similar to FIG. 138 showing the component [arts in assembled relation relative to each other.
Figure 138:
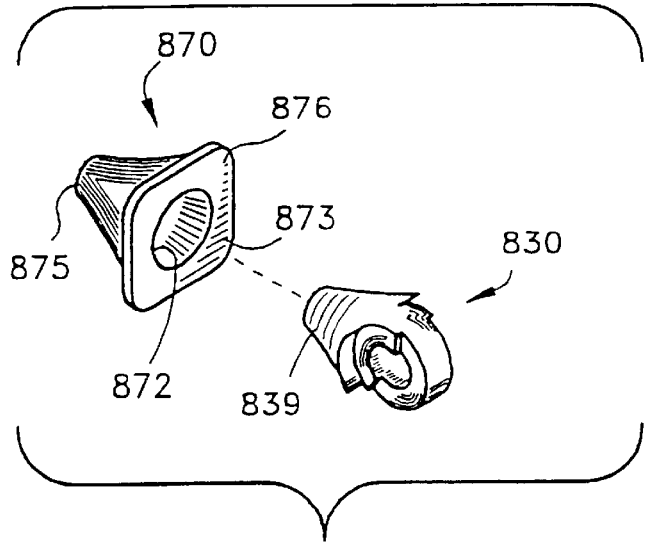
FIG. 138 is a perspective view showing the grommet illustrated in FIGS. 132 through 136 in disassembled relation relative to a sleeve.

Thereafter, and as shown in FIGS. 137 and 138, sleeve 830 is axially inserted into operable combination with the grommet 870. More specifically, the smaller end portion 839 of sleeve 830 is initially inserted into cavity 872 of sleeve 870. The taper on the outer surface of sleeve 830 combines and cooperates with the taper on the internal surface of cavity 872 of sleeve 870. Accordingly, sleeve 830 is free to move axially or rotatably (FIG. 139) within the socket 872 of grommet 870. The ability of the sleeve 830 to rotate and move axially relative to the grommet 870 means that the connector assembly 818 allows greater variability in preventing fractures of a finger from traction forces applied thereto that typically result from a fall while allowing the implanted joint assembly 816 to remain firmly ingrown with the human body. Alternatively, the taper on the outer surface of sleeve 830 combines and cooperates with the taper on the internal surface of cavity 872 of sleeve 870 in a manner establishing a conventional Morse taper connection therebetween.

The above described implant procedure is repeated with respect to bone 212. Notably, the ability of the sleeves 830, 840 to axially move relative to the grommets 870, 880, respectively, furthermore promotes the ability of the surgeon to join opposed end regions of the prosthetic assembly 816 relative to each other.

The unique advantages yielded by a joint assembly having grommets and sleeves that are maintained in the above-described operable association can be accomplished through other component configurations while not detracting or departing from the spirit and scope of the invention. In this regard, another exemplary form of sleeve and grommet configuration that yields the advantages described above is schematically illustrated in FIGS. 140 and 141. The components of this alternative embodiment of grommet and sleeve that are identical or functionally analogous to those components of sleeve 830, 840 and grommets 870, 880 are designated by reference numerals identical to those used to describe sleeve 830 and grommets 870 with the exception that this embodiment uses reference numerals in the 900 series.

Figure 140:
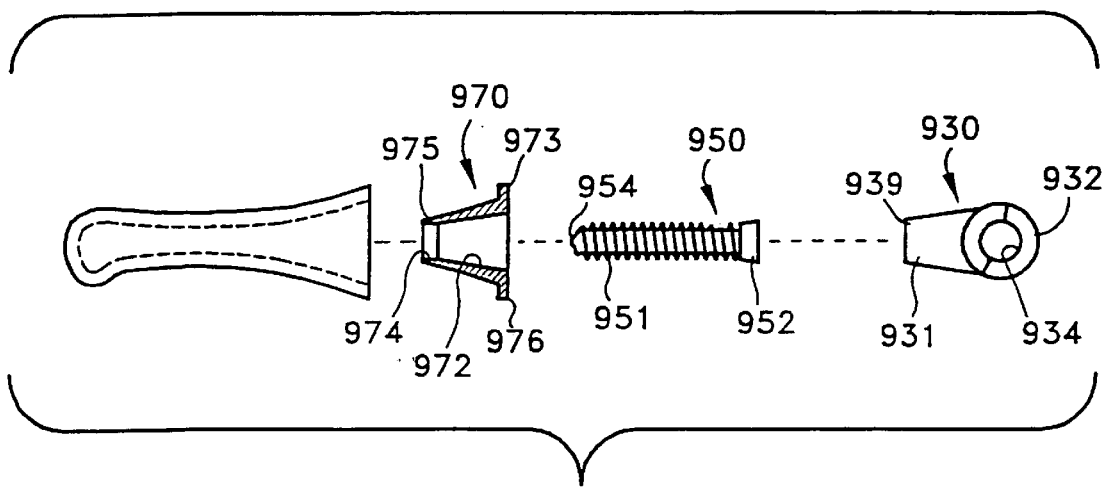
FIG. 140 is a view similar to FIG. 137 but showing an alternative form of grommet and sleeve combination forming part of the present invention.
Figure 147:
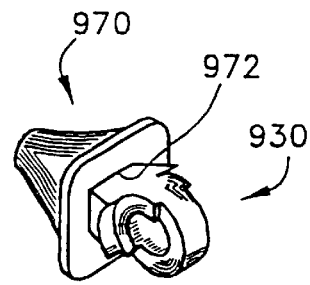
FIG. 147 is a perspective view similar to FIG. 141 but showing the component parts in assembled relation relative to each other.
Figure 141:
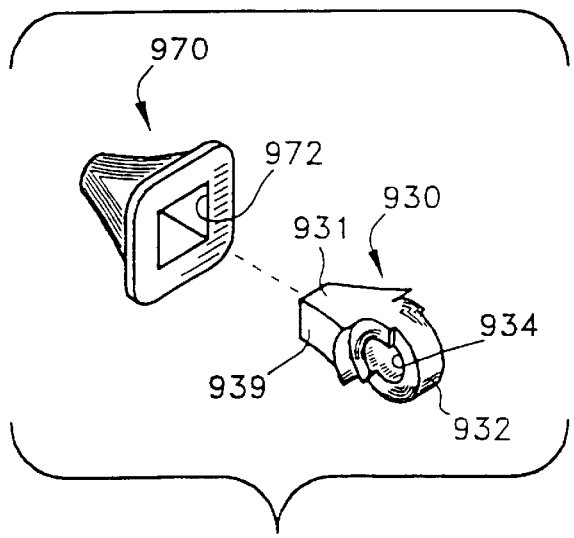
FIG. 141 is a perspective view of an alternative sleeve and grommet combination.
Figure 142:
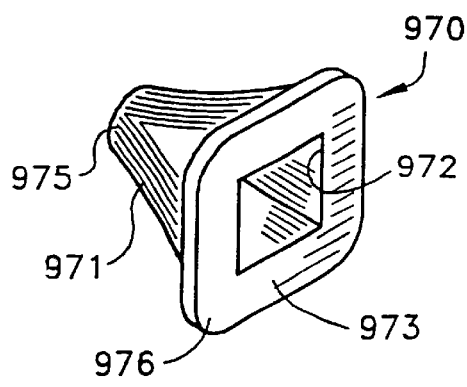
FIG. 142 is a perspective view of the grommet illustrated in FIG. 141.
Figure 143:
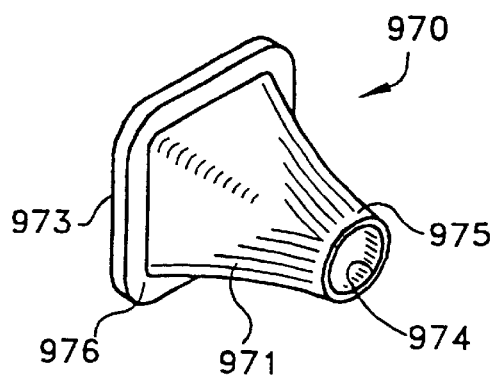
FIG. 143 is another perspective view of the grommet illustrated in FIG. 141 but from a different perspective.
Figure 144:
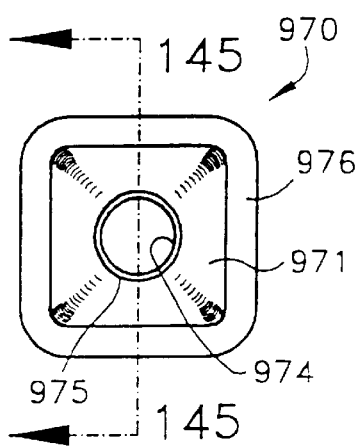
FIG. 144 is an end view of the alternative grommet illustrated in FIGS. 141 and 142.
Figure 145:
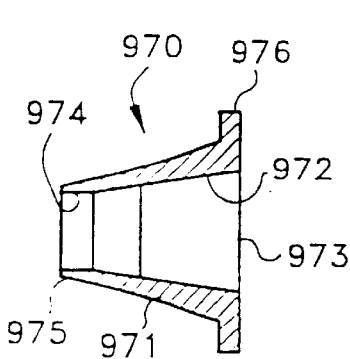
FIG. 145 is a sectional view taken along line 145—145 of FIG. 144.

Each sleeve of the implanted joint assembly can alternatively be configured as shown in FIGS. 140 and 141. Each sleeve 930 comprises an axially elongated member 931 preferably fabricated from a material that is compatible with human bone tissue and is preferably selected from the class including: titanium, a titanium alloy, stainless steel, or a cobalt chromium alloy. At one end, member 931 includes an eye portion 932 defining a cylindrical bore 934 preferably having a closed margin. The eye portion 932 of sleeve 930 is identical to the eye portion 832 of sleeve 830 and thus no further detail need be provided at this time for a complete understanding of the sleeve 930.

In this alternative embodiment of the sleeve, the other end portion 939 of member 931 has a generally rectangular cross-sectional configuration. The cross-sectional configuration of the end portion 939 of member 931 opposite from eye portion 932 is considerably smaller than the eye portion 932 to promote insertion of the sleeve 930 into a grommet 970 as will be discussed below. In this alternative embodiment of the sleeve for the implant joint assembly, the outer surface configuration has a steadily increasing rectangular cross-sectional shape between end portion 939 and the eye portion 932.

It should be appreciated that the other sleeve for this alternatively configured arthroplasty joint assembly is similarly shaped. That is, the other sleeve has a eye portion that is identical to the eye portion 842 of sleeve 840 discussed above. Moreover, the end portion of the other sleeve of the joint assembly has a configuration similar to that discussed above with respect to sleeve 930. Accordingly, no further description need be provided for a complete understanding of this alternative sleeve structure.

As will be appreciated, the alternative embodiment of grommet 970 has a configuration that compliments the alternative structure of the sleeve 930. As shown in FIGS. 142 through 146, the alternative grommet 970 is preferably formed from a material chosen from the class including: titanium, a titanium alloy, stainless steel, or a cobalt chromium alloy. As shown, each grommet includes an axially elongated hollow member 971 that defines a cavity 972 that opens to end 973 of the grommet. Preferably, a coaxial bore 974 extends axially inward and opens to cavity 972 from an opposite end 975 of the grommet. A stop flange 976 is preferably provided on the grommet 970 for limiting its axial insertion within the medullary cavity and to stabilize the joint assembly following implantation within the human body.

Notably, cavity 972 has a increasing rectangular cross-sectional configuration that closely proximates the cross-sectional outer surface configuration on the respective sleeve 930 adapted to be fitted therewithin. Returning to FIG. 140, a screw 950 (similar to screw 850 discussed in detail above) is adapted to cooperate with the grommet 970 to hold the illustrated portion of the implanted joint assembly in place. It is important to note that the smallest portion of the cavity 972 has an area that is smaller than the first predetermined diameter of the head portion 952 of the screw 950 adapted to pass endwise therethrough thereby preventing the respective screw 950 from passing endwise therethrough when the artificial joint assembly is implanted within the living body of the patient. In this regard, the diameter of the coaxial bore 974 is sized such that it permits the threaded portion 951 of the respective screw 950 to axially slide or pass endwise through the respective grommet to be fastened within bone substance while the head portion 952 of the respective screw 950 remains in operable combination with the grommet 970.

Not unlike the grommets 870, 880 mentioned above, the alternatively shaped grommets 970 are intended to be provided in a plurality of various sizes. As will be appreciated, the various size of the grommets 970 allow the surgeon to select a grommet that is sized to particularly fit well within the medullary cavity of the particular patient wherein a joint is being replaced thereby advantageously stabilizing the joint assembly relative to the end regions of the bones that are to be articulately joined to each other. Moreover, and like those mentioned above, the grommets 970 are specifically designed and/or configured to promote boney ingrowth. Thus, and while each screw associated with the grommet 970 serves to initially fasten the joint assembly in place, the grommets 970, along with their boney ingrowth relative to the bone substance, serve to positively maintain the surgically implanted joint assembly in place for long term usage.

As will be appreciated, the specific size of the grommet 970 can vary. The intended function, purpose, and overall configuration of the alternative grommets 970 used in this alternative embodiment of joint assembly are, however, preferably identical to each other. Accordingly, the above detailed description of grommet 970 will suffice for an understanding that alternative grommet designs can be used without detracting or departing from the spirit and scope of the present invention.

As shown in FIG. 140, the end portion 975 of the grommet 970 is adapted to be initially inserted into the medullary cavity of the severed bone and, accordingly, has a reduced cross-sectional area. Preferably, each grommet 970 is provided with a flanged configuration 976 arranged toward a trailing end thereof for limiting axial insertion of the grommet within the medullary cavity of the severed bone.

The end portion 975 of grommet 970 preferably has a generally circular cross-sectional configuration that tapers outwardly to end region 973 having a larger and preferably rectangular cross-sectional configuration. Suffice it to say, the grommet selection is chosen by which grommet configuration most closely corresponds to or proximates the inner endosteal surface configuration of the severed bone.

The outer surface of grommet 970, extending between opposed end portions 973 and 975, is preferably treated to promote boney ingrowth. That is, the outer surface of grommet 970 preferably has a burnished surface finish or a cancellous micron pore size ranging between about 100 and about 450 microns to promote boney ingrowth between the surrounding bone tissue and the respective grommet.

Following insertion of the grommet 970 into the medullary cavity, the pointed end 954 of the fastening screw 950 is inserted into and through cavity 972 and bore 974 of grommet 970 such that it can be fastened into the bone substance. Notably, the head portion 952 of the screw cooperates with the internal surface of cavity 972 on grommet 970 to further draw and enhance securement of the grommet 970 into the medullary cavity of the severed bone. Preferably, the grommet 970 is drawn into the medullary cavity until the stop flange 976 abuts with the exposed end region of the surgically severed bone thereby adding stability to the joint assembly.

Figure 146:
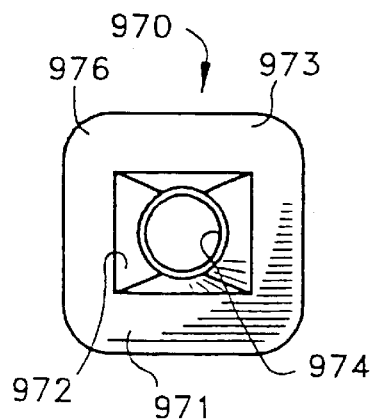
FIG. 146 is another end view of the alternative grommet shown in FIGS. 142 and 143.

Thereafter, and as shown in FIGS. 140 and 141, sleeve 930 is axially inserted into operable combination with the grommet 970. More specifically, the smaller end portion 939 of sleeve 930 is initially inserted into cavity 972 of sleeve 970. As shown in FIG. 146, the rectangular taper on the outer surface of sleeve 930 combines and cooperates with the rectangular taper on the internal surface of cavity 972 of sleeve 970. Accordingly, sleeve 930 is free to move axially within the socket 972 of grommet 970. The ability of the sleeve 930 to move axially relative to the grommet 970 means that the implanted joint assembly allows greater variability in preventing fractures of a human digit from traction forces applied thereto that typically result from a fall while allowing the implanted joint assembly to remain firmly ingrown with the human body.

It should also be appreciated that different combinations of components can be used to form the artificial joint assembly. That is, a grommet 870 and sleeve 830 may be preferably inserted into one bone while grommet 970 and sleeve 930 may be inserted into the other bone. Connector 820 is used to articulately interconnect the free ends of sleeves 830 and 930 to each other thereby defining the implanted artificial joint.

Regardless of the particular joint assembly embodiment used, the joint assemblies described above readily permit natural small joints, that fail, to be replaced with an artificial joint assembly comprised of mechanical components that are not susceptible to arthritis, and other debilitating diseases. In one form of the invention, the bone screws are fixedly attached to the connector thereby eliminating separation problems between the various mechanical components of the joint assembly. Alternatively, a connector assembly is operably connected to the bone screws in a manner preventing fractures of a human digit from traction forces applied thereto. In still another embodiment of the invention, the connector assembly that articulately interconnects the bones is permitted to rotate about an axis extending generally normal to the axis of the bone screws to further dissipate the likelihood of damage to the bones resulting from the patient inadvertently falling and imparting unusual motions to the implanted mechanical joint assembly of the present invention. Another important aspect of the present invention relates to a mechanical joint assembly having grommets that are configured and designed specifically to promote honey ingrowth. As will be appreciated, the ability of tile surgeon to select that particular grommet shape that most closely corresponds to the endosteal shape of the cavity in which it is inserted coupled with the ability of the grommet to fixedly secure to the bone tissue through boney ingrowth will advantageously serve to maintain the artificial joint assembly in place regardless of the resorption of bone that frequently occurs around a bone screw.

From the foregoing, it will be observed that numerous modifications and variations can be effected without departing from the true spirit and scope of the novel concept of the present invention. It will be appreciated that the present disclosure is intended as an exemplification of the invention, and is not intended to limit the invention to the specific embodiment illustrated. The disclosure is intended to cover by the appended claims all such modifications as fall within the scope of the claims.

What is claimed is:

1. A joint assembly for interconnecting first and second opposed end regions of adjacent first and second bones of a person, said joint assembly comprising:

a first axially elongated member defining a bore extending along a longitudinal axis of said first member and having external threading extending lengthwise from a first end of the first member wherein, when in an operative position, at least a portion of said first member is anchored in the first bone such that a joint end of said first member projects a distance away from the end region of the first bone and extends toward the second bone;

a second axially elongated member defining a bore extending along a longitudinal axis of said second member and having external threading extending lengthwise from a first end of said second member wherein, when in an operative position, at least a portion of said second member is anchored in the second bone such that a joint end of said second member projects a distance away from the end region of the second bone and extends towards the first bone;

a connector, wherein said connector comprises a generally U-shaped member having a first leg portion defining an aperture therethrough and a second leg portion defining an aperture therethrough, said first and second leg portions joined to each other by a bight portion extending therebetween, said first leg portion attached to said joint end of said first axially elongated member and said second leg portion attached to said joint end of said second axially elongated member; and first and second fasteners, said first fastener extending through said aperture defined by said first leg portion of said connector and into said bore of said first member and said second fastener extending through said aperture defined by said second leg portion of said connector and into said bore of said second member.

2. The joint assembly of claim 1 wherein said first and second axially elongated members define a radially extending bore, said radially extending bore intersecting said longitudinal bore and opening to an outer surface of said members.

3. The joint assembly of claim 1 wherein said first leg portion and said second leg portion define a recess, said recess located on an inner surface of said leg portions and further comprising first and second thrust washers, said first thrust washer disposed on said first fastener and received within said recess of said first leg portion and said second thrust washer disposed on said second fastener and received within said recess of said second leg portion.

4. The joint assembly of claim 1 further comprising first and second retainers, said first retainer disposed around at least a portion of said longitudinal bore of said first axially elongated member and said second retainer disposed around at least a portion of said longitudinal bore of said second axially elongated member.

5. The joint assembly of claim 1 wherein said longitudinal bores defined by said first and second axially elongated members include threading and wherein said first and second fasteners include a head portion and a threaded shank portion, said first fastener threaded shank portion threadedly received within said first axially elongated member longitudinal bore and said second fastener threaded shank portion threadedly received within said second axially elongated member longitudinal bore.

6. The joint assembly of claim 5 further comprising a driving tool wherein said driving tool, when in an operative position, is able to be releasably accommodated within said head portions of said first and second fasteners.

7. The joint assembly of claim 1 wherein said first and second axially elongated members include a reduced diameter portion disposed at said joint ends of said first and second members.

8. The joint assembly of claim 1 wherein said longitudinal bores defined by said first and second axially elongated members include a first threaded portion of a first diameter disposed at said first end of said axially elongated member and a second unthreaded portion of a second diameter disposed at said joint end of said axially elongated member, said second diameter greater than said first diameter.

9. A joint assembly for interconnecting first and second opposed end regions of adjacent first and second bones of a person, said joint assembly comprising:

a first axially elongated member defining an elongated axis and having external threading extending endwise from a first end thereof and adapted for anchoring said first member in the medullary cavity of the first bone, said first member defining a coaxial bore that opens to a second end of said first member, said bore having internal threading extending along at least a lengthwise portion thereof;

a second axially elongated member defining an elongated axis and having external threading extending endwise from a first end thereof and adapted for anchoring said second member in the medullary cavity of the second bone, said second member defining a coaxial bore that opens to a second end of said second member, said bore having internal threading extending along at least a lengthwise portion thereof;

a generally U-shaped connector interposed between and attached to said second ends of said first and second members, said connector having generally parallel inner and outer surfaces and defining opposed first and second leg portions, said first and second leg portions including a free end and a joined end, wherein said joined ends are joined to each other by a flexible bight portion, and wherein said first and second leg portions define an aperture proximate to said free end thereof; and first and second fasteners, said first and second fasteners including a head portion and a shank portion, wherein said shank portion has external threading corresponding to the internal threading of said first and second members, and wherein said shank portion of said first fastener is received through said aperture defined by said first leg portion and within said coaxial bore defined by said first member and said shank portion of said second fastener is received through said aperture defined by said second leg portion and within said coaxial bore defined by said second member.

10. The joint assembly of claim 9 further comprising first and second thrust washers, said first thrust washer disposed on said shank portion of said first fastener and said second thrust washer disposed on said shank portion of said second fastener.

11. The joint assembly of claim 10 wherein said inner surface of said connector defines first and second recesses, said first and second recesses receiving within them said first and second thrust washers, respectively.

12. The joint assembly of claim 9 wherein said first and second members define a throughbore extending radially from said coaxial bore to said exterior threading.

13. The joint assembly of claim 9 wherein said first and second members include a retainer, said retainer positioned around at least a portion of said coaxial bore.

14. The joint assembly of claim 9 wherein said first and second members include a retainer, said retainer positioned within said coaxial bore.

15. A joint assembly kit, comprising:

a plurality of screws, wherein each screw defines a bore extending along a longitudinal axis thereof and has external threading extending lengthwise from a first end to a second end thereof, and wherein, in an operative position, said first end of a first one of said screws is anchored in a first bone such that said second end of said first one of said screws extends toward a second adjacent bone, and wherein, in the operative position, said first end of a second one of said screws is anchored in the second bone such that said second end of said second one of said screws extends toward the first bone;

a plurality of connectors, wherein each of said connectors comprises a generally U-shaped member having a first leg portion defining an aperture therethrough and a second leg portion defining an aperture therethrough, said first and second leg portions joined to each other by a bight portion extending therebetween; and a plurality of fasteners for interconnecting said first and second leg portions of connectors to said second ends of said screws, wherein, in an operative position, a first one of said fasteners extends through said aperture defined by said first leg portion of one of said connectors and into said bore of said first one of said screws and wherein a second one of said fasteners extends through said aperture defined by said second leg portion of said one of said connectors and into said bore of said second one of said screws.

16. A method for interconnecting first and second opposed end regions of adjacent first and second bones of a person, comprising the steps of:

threading a first screw in the first bone, said first screw defining a bore extending along a longitudinal axis of said first screw;

threading a second screw in the second bone, said second screw defining a bore extending along a longitudinal axis of said second screw; and interconnecting said first screw to said second screw by securing a U-shaped member to said first and second screws, said U-shaped member including a first leg portion defining an aperture therethrough, a second leg portion defining an aperture therethrough, and a flexible bight portion extending therebetween, said first leg portion and said second leg portion disposed in a generally parallel relationship with one another, wherein said first leg portion is secured to said first screw and said second leg portion is secured to said second screw by first and second fasteners, respectively, said first fastener extending through said aperture defined by said first leg portion and into said bore of said first screw and said second fastener extending through said aperture defined by said second leg portion and into said bore of said second screw.

17. The method of claim 16 wherein each of said first and second screws further define a radially extending bore opening to said longitudinal bore and further comprising the step of providing an adhesive material through said radially extending bores of said first and second screws and to the first and second bones, respectively, to securely bond said screws to the respective bones.

18. The method of claim 16 further comprising the step of distributing a first interconnection force resultant from connection of said U-shaped member to said first screw onto a first thrust washer and distributing a second interconnection force resultant from connection of said U-shaped member to said second screw onto a second thrust washer.

* * * * *

UNITED STATES PATENT AND TRADEMARK OFFICE
CERTIFICATE OF CORRECTION

PATENT NO. : 6,475,242 B1
DATED : November 5, 2002
INVENTOR(S) : Dale G. Bramlet It is certified that error appears in the above-identified patent and that said Letters Patent is hereby corrected as shown below:

Column 8,
Line 66, change "[arts" to -- parts --;

Column 13,
Line 32, change "a" to -- α --;

Column 15,
Line 11, change "affect" to -- effect --;
Line 25, change "affect" to -- effect --;

Column 17,
Line 13, change "proximates" to -- approximates --;
Line 19, change "cancerous" to -- cancellous --;
Line 20, change "bonzy" to -- boney --;

Column 18,
Line 9, delete "u";

Column 20,
Line 62, change "63Q" to -- 630 --;

Column 23,
Line 25, change "is" to -- are --;
Line 63, change "cancerous" to -- cancellous --;

Column 25,
Line 13, change "ill" to -- in --;

Column 32,
Line 53, change "honey" to -- boney --;

UNITED STATES PATENT AND TRADEMARK OFFICE
CERTIFICATE OF CORRECTION

PATENT NO.   : 6,475,242 B1
DATED        : November 5, 2002
INVENTOR(S)  : Dale G. Bramlet It is certified that error appears in the above-identified patent and that said Letters Patent is hereby corrected as shown below:

<u>Column 32 cont'd,</u>
Line 54, change "tile" to -- the --.

Signed and Sealed this

Second Day of September, 2003

JAMES E. ROGAN
*Director of the United States Patent and Trademark Office*